US012673111B2

(12) United States Patent
Dubowchik et al.

(10) Patent No.: US 12,673,111 B2
(45) Date of Patent: Jul. 7, 2026

(54) BIFUNCTIONAL DEGRADERS OF GALACTOSE-DEFICIENT IMMUNOGLOBULINS

(71) Applicant: Biohaven Therapeutics Ltd., New Haven, CT (US)

(72) Inventors: Gene M. Dubowchik, Killingworth, CT (US); Ada Vaill, Salem, CT (US); Reese M. Caldwell, Cambridge, MA (US); Brian M. Linhares, Bedford, MA (US); David K. Leahy, Marblehead, MA (US); James Bryson, Asheville, NC (US); Lawrence R. Marcin, Bethany, CT (US)

(73) Assignee: Biohaven Therapeutics Ltd., Tortola (VG)

( * ) Notice: Subject to any disclaimer, the term of this patent is extended or adjusted under 35 U.S.C. 154(b) by 0 days.

(21) Appl. No.: 19/060,384

(22) Filed: Feb. 21, 2025

(65) Prior Publication Data

US 2025/0228957 A1 Jul. 17, 2025

Related U.S. Application Data

(63) Continuation of application No. PCT/US2024/026733, filed on Apr. 29, 2024.

(60) Provisional application No. 63/499,231, filed on Apr. 29, 2023, provisional application No. 63/504,877, filed on May 30, 2023, provisional application No. 63/604,935, filed on Dec. 1, 2023, provisional application No. 63/623,279, filed on Jan. 21, 2024, provisional application No. 63/567,174, filed on Mar. 19, 2024.

(51) Int. Cl.
*A61K 47/68* (2017.01)
*A61K 31/7008* (2006.01)
*C07K 16/28* (2006.01)

(52) U.S. Cl.
CPC ...... *A61K 47/6807* (2017.08); *A61K 31/7008* (2013.01); *C07K 16/283* (2013.01)

(58) Field of Classification Search
None
See application file for complete search history.

(56) References Cited

U.S. PATENT DOCUMENTS

| | | | |
|---|---|---|---|
| 7,083,784 | B2 | 8/2006 | Dall'Acqua et al. |
| 7,658,921 | B2 | 2/2010 | Dall'Acqua et al. |
| 8,088,376 | B2 | 1/2012 | Chamberlain et al. |
| 8,969,526 | B2 | 3/2015 | Baehner et al. |
| 9,562,100 | B2 | 2/2017 | Dall'Acqua et al. |
| 2009/0317381 | A1 | 12/2009 | Plaut et al. |
| 2020/0190165 | A1 | 6/2020 | Yamada et al. |
| 2022/0275106 | A1 | 9/2022 | Chen et al. |
| 2024/0309114 | A1* | 9/2024 | Dubowchik ......... A61K 47/549 |

FOREIGN PATENT DOCUMENTS

| | | | | |
|---|---|---|---|---|
| EP | 1355919 | B1 | 11/2010 | |
| JP | 2010-285419 | A | 12/2010 | |
| WO | 2002060919 | A2 | 8/2002 | |
| WO | 2011081189 | A1 | 7/2011 | |
| WO | 2012017021 | A2 | 2/2012 | |
| WO | 2015064348 | A1 | 5/2015 | |
| WO | 2019023501 | A1 | 1/2019 | |
| WO | WO-2019199634 | A1 * | 10/2019 | A61K 47/549 |
| WO | 2022192478 | A1 | 9/2022 | |

OTHER PUBLICATIONS

Lloyd et al., Protein Engineering, Design & Selection 22:159-168 (Year: 2009).*
Edwards et al.., J Mol Biol 334(1): 103-118 (Year: 2003).*
Poosarla et al., Biotechn. Bioeng., 114(6): 1331-1342 (Year: 2017).*
Strop et al.,m Chemistry and Biology 20: 161-167 (Year: 2013).*
Nejadmoghaddam et al., Avicenna Journal of Medical Biotechnology 2(1): 3-23 (Year: 2019).*
International Search Report dated Sep. 9, 2024 issued for the corresponding application PCT/US2024/026733 (5 pages).
Written Opinion dated Sep. 9, 2024 issued for the corresponding application PCT/US2024/026733 (10 pages).
Yasutake et al. "Novel lectin-independent approach to detect galactose-deficient IgA1 in IgA nephropathy" Nephrol Dial Transplant, (2015) 30: 1315-1321.
Lai et al. "IgA nephropathy" Nat Rev Dis Primers, Feb. 11, 2016:2:16001.
Yamasaki et al. "Galactose-deficient IgA1-specific antibody recognizes GalNAc•modified unique epitope on hinge region of IgA1" Monoclonal Antibodies in Immunodiagnosis and Immunotherapy, 2018, 37(6), 252-256.
Barratt et al."Randomized phase II JANUS study of atacicept in patients with IgA nephropathy and persistent proteinuria" Kidney Int. Rep. 7(8), 1831-1841 (2022).
Caianiello et al."Bifunctional small molecules that mediate the degradation of extracellular proteins" Nature Chemical Biology 17(9), 947-953 (2021).
IBL-America "Novel ELISA (using KM55) specifically detects Gd-IgA1 #27600 Gd-IgA1 (Galactose-deficient IgA1)" Pamphlet 2.
Ishiko et al. "Utility of glomerular Gd-IgA1 staining for indistinguishable cases of IgA nephropathy or Alport syndrome" Clin Exp Nephrol., 25(7), 779-787 (Jul. 2021).

(Continued)

*Primary Examiner* — Phuong Huynh

(57) ABSTRACT

A composition of matter including a deglycosylated IgA-binding moiety, a cellular receptor-binding moiety that binds to hepatocytes or other degrading cells through asialoglycoprotein receptors (ASGPR) on the surface of hepatocytes or other degrading cells in a patient or subject, and optionally, a linker moiety connecting deglycosylated IgA-binding moiety and the cellular receptor-binding moiety, wherein the composition of matter is useful for removing galactose-deficient IgA1 in a patient or subject.

14 Claims, 17 Drawing Sheets

Specification includes a Sequence Listing.

(56) References Cited

OTHER PUBLICATIONS

Knoppova et al. "Pathogenesis of IgA nephropathy: Current understanding and implications for development of disease-specific treatment" J. Clin. Med., 10(19), 4501 (2021).
Kuroyanagi et al. "Galactose-deficient IgA1 is involved in IgA deposition in renal grafts biopsied one hour after kidney transplantation" Intern. Med. (Oct. 26, 2022).
Lai et al. "IgA nephropathy" Nature Rev. Dis. Primers, 2, 16001 (2016).
Martin-Penagos et al. "Measurement of galactosyl-deficient IgA1 by the monoclonal antibody Km55 contributes to predicting patients with IgA nephropathy with high risk of long-term progression" Nefrologia, 41(3), 311-320 (May-Jun. 2021).
Moldoveanu et al. "Patients with IgA nephropathy have increased serum galactose-deficient IgA1 levels" Kidney International, 71(11), 1148-54 (2007).
Neufeld et al. "Galactose-deficient IgA1 (GD-IgA1) in skin and serum from patients with skin-limited and systemic IgA Vasculitis" J. Am. Acad. Dermatol. (Mar. 19, 2019).
Nihei et al. "Current understanding of IgA antibodies in the pathogenesis of IgA nephropathy" Front. Immunol., 14, 1165394 (2023).
Nishioka et al. "Glomerulonephritis with severe nephrotic syndrome induced by immune complexes composed of galactose-deficient IgA1 in primary Sjogren's syndrome: A case report" BMC Nephrol., 22(1), 108 (Mar. 25, 2021).
Rajasekaran et al. "IgA nephropathy: An interesting autoimmune kidney disease" Am. J. Med. Sci., 361(2), 176-194 (2021).
Suzuki et al. "Aberrantly glycosylated IgA1 in IgA nephropathy patients is recognized by IgG antibodies with restricted heterogeneity" J. Clin. Invest., 119(6), 1668-1677 (2009).
Suzuki et al. "IgA nephropathy and IgA vasculitis with nephritis have a shared feature involving galactose-deficient IgA1-oriented pathogenesis" Kidney Int. Mar. 2018, 93(3):700-705.
Suzuki "Biomarkers for IgA nephropathy based on multi-hit pathogenesis" Clinical Exp. Nephrol., 23(1), 26-31 (Jan. 2019).
Yamasaki et al. "Galactose-deficient IgA1-specific antibody recognizes GalNAc-changed unique epitope on hinge region of IgA1" Monoclonal Antibody Immunodiagn. Immunother., 37(6), 252-256 (Dec. 2018).
Yasutake et al. "Novel lectin-independent approach to detect galactose-deficient IgA1 in IgA nephropathy" Nephrol Dial Transplant, 30, 1315-1321 (2015).
Zhang et al. "Clinical significance of galactose-deficient IgA1 by Km55 in patients with IgA nephropathy" Kidney Blood Pressure Res., 44, 1196-1206 (2019).
Zhang et al. "Km55 monoclonal antibody staining in IgA-dominant infection-related glomerulonephritis" Nephron, 145(3), 225-237 (2021).

* cited by examiner

| | $EC_{50}$ |
|---|---|
| Galactose defiecient IgA | 0.84 |
| Total IgA | 33 |

Compound I

Compound I

TABLE 1
R-Groups for MATE reagents and bifunctional MoDE final components

| | |
|---|---|
| MATO1A |  |

TABLE 1
R-Groups for MATE reagents and bifunctional MoDE final components

| | |
|---|---|
| MAT01B |  |

TABLE 1
R-Groups for MATE reagents and bifunctional MoDE final components

| | |
|---|---|
| MATOIC |  |

| TABLE 1<br>R-Groups for MATE reagents and bifunctional MoDE final components | |
|---|---|
| MATOID |  |

TABLE 1
R-Groups for MATE reagents and bifunctional MoDE final components

| | |
|---|---|
| MAT01E |  |
| MAT01F |  |

TABLE 1
R-Groups for MATE reagents and bifunctional MoDE final components

| | |
|---|---|
| MATOIG |  |

TABLE 1
R-Groups for MATE reagents and bifunctional MoDE final components

| | |
|---|---|
| MAT01H |  |
| MAT01I |  |
| MAT01J |  |
| MAT01K |  |

SEQUENCE LISTING

```
Sequence total quantity: 18
SEQ ID NO: 1            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
SEQUENCE: 1
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 2            moltype = AA  length = 219
FEATURE                 Location/Qualifiers
source                  1..219
                        mol_type = protein
                        organism = Rattus norvegicus
REGION                  24..38
                        note = CDR1 is KSSQSLVHTDGKTYLH
REGION                  54..61
                        note = CDR2 is QVSNLGS
REGION                  94..102
                        note = CD3 is VQATHFPLT
SEQUENCE: 2
DVVLTQTPPP LSVAIGQSVS ISCKSSQSLV HTDGKTYLHW LLQSPGQSPK LLIYQVSNLG  60
SGVPDRFSGT GSQKDFTLKI SRVEAEDLGV YYCVQATHFP LTFGIGTKLE LQRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 3            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
SEQUENCE: 3
ELQLQESGPG LVKPSQSLSL TCSVTGYSIR SNYWGWIRKF PGNKMEWMGY ITYSGGTYYN  60
```

```
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 4            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
VARIANT                 329
                        note = LALA/PA = L234A/L235/P329A
SEQUENCE: 4
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALAAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 5            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
VARIANT                 329
                        note = LALA/PA = L234A/L235/P329A
VARIANT                 428
                        note = LS = M428L/N434S
VARIANT                 434
                        note = LS = M428L/N434S
SEQUENCE: 5
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALAAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPGK                                       446

SEQ ID NO: 6            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
VARIANT                 329
                        note = LALA/PA = L234A/L235/P329A
VARIANT                 252
                        note = YTE = M252Y/S254T/T256E
```

-continued

```
VARIANT                 254
                        note = YTE = M252Y/S254T/T256E
VARIANT                 256
                        note = YTE = M252Y/S254T/T256E
SEQUENCE: 6
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALAAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 7            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
VARIANT                 428
                        note = LS = M428L/N434S
VARIANT                 434
                        note = LS = M428L/N434S
SEQUENCE: 7
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVLHEA LHSHYTQKSL SLSPGK                                     446

SEQ ID NO: 8            moltype = AA  length = 446
FEATURE                 Location/Qualifiers
source                  1..446
                        mol_type = protein
                        organism = Rattus norvegicus
REGION                  31..36
                        note = CDR1 is SNYWG
REGION                  49..65
                        note = CDR2 is YITYSGGTYYNPSLKS
REGION                  98..104
                        note = CDR3 is WGDWYFDF
VARIANT                 234..235
                        note = LALA = L234A/L235A
VARIANT                 252
                        note = M252Y/S254T/T256E
VARIANT                 254
                        note = M252Y/S254T/T256E
VARIANT                 256
                        note = M252Y/S254T/T256E
SEQUENCE: 8
ELQLQESGPG LVKPSQSLSL TCSVTGYSIR SNYWGWIRKF PGNKMEWMGY ITYSGGTYYN  60
PSLKSRISIT RDTSKNQFFL QLTSVTTEDT ATYYCTRWGD WYFDFWGPGT KVTVSPASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 9            moltype = AA  length = 5
FEATURE                 Location/Qualifiers
source                  1..5
                        mol_type = protein
                        organism = Rattus norvegicus
SEQUENCE: 9
SNYWG                                                            5

SEQ ID NO: 10           moltype = AA  length = 16
```

-continued

```
FEATURE                Location/Qualifiers
source                 1..16
                       mol_type = protein
                       organism = Rattus norvegicus
SEQUENCE: 10
YITYSGGTYY NPSLKS                                                   16

SEQ ID NO: 11          moltype = AA  length = 8
FEATURE                Location/Qualifiers
source                 1..8
                       mol_type = protein
                       organism = Rattus norvegicus
SEQUENCE: 11
WGDWYFDF                                                            8

SEQ ID NO: 12          moltype = AA  length = 16
FEATURE                Location/Qualifiers
source                 1..16
                       mol_type = protein
                       organism = Rattus norvegicus
SEQUENCE: 12
KSSQSLVHTD GKTYLH                                                   16

SEQ ID NO: 13          moltype = AA  length = 7
FEATURE                Location/Qualifiers
source                 1..7
                       mol_type = protein
                       organism = Rattus norvegicus
SEQUENCE: 13
QVSNLGS                                                             7

SEQ ID NO: 14          moltype = AA  length = 9
FEATURE                Location/Qualifiers
source                 1..9
                       mol_type = protein
                       organism = Rattus norvegicus
SEQUENCE: 14
VQATHFPLT                                                           9

SEQ ID NO: 15          moltype = AA  length = 5
FEATURE                Location/Qualifiers
source                 1..5
                       mol_type = protein
                       organism = synthetic construct
SEQUENCE: 15
LPETG                                                               5

SEQ ID NO: 16          moltype = AA  length = 330
FEATURE                Location/Qualifiers
source                 1..330
                       mol_type = protein
                       organism = Homo sapiens
SEQUENCE: 16
ASTKGPSVFP LAPSSKSTSG GTAALGCLVK DYFPBPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWINGK EYKCRVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEATHNHYT QKSLSLSPGK                                    330

SEQ ID NO: 17          moltype = AA  length = 326
FEATURE                Location/Qualifiers
source                 1..326
                       mol_type = protein
                       organism = Homo sapiens
SEQUENCE: 17
ASTKGPSVFP LAPCSRSTSE STAALGCLVK DYFPBPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REBQFNSTFR  180
VVSVLTVLHQ DWLNGKEYKC KVSNKGLPAP IEKTISKTKG OPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA THNHYTQKSL SLSPGK                                        326

SEQ ID NO: 18          moltype = AA  length = 327
FEATURE                Location/Qualifiers
source                 1..327
                       mol_type = protein
                       organism = Homo sapiens
SEQUENCE: 18
```

-continued

```
ASTKGPSVFP LAPCSRSTSE STAALGCLVK DYFPBPVTVS WNSGALTSGV HTFPAVLQSS  60
GLYSLSSVVT VPSSSLGTKT YTCNVDHKPS NTKVDKRVES KTGPPCPSCP APEFLGGPSV 120
FLFPPKPKDT LMISRTPEVT CVVVDVSQED PEVQFNWYVD GVEVHNAKTK PREEQFNSTY 180
RVVSVLTVLH QDWINGKEYK CKVSNKGLPS SIEKTISKAK GOPREPQVYT LPPSQEEMTK 240
NQVSLTCLVK GFYPSDIAVE WESNGQPENN YKTTPPVLDS DGSFFLYSRL TVDKSRWQEG 300
NVFSCSVMHE ATHNHYTQKS LSLSLGK                                    327
```

BIFUNCTIONAL DEGRADERS OF GALACTOSE-DEFICIENT IMMUNOGLOBULINS

CROSS-REFERENCE TO RELATED APPLICATIONS

This application is a continuation of International Application No. PCT/US2024/026733, filed Apr. 29, 2024, which claims priority to U.S. Provisional Patent Application No. 63/499,231 filed Apr. 29, 2023, U.S. Provisional Patent Application No. 63/504,877 filed May 30, 2023, U.S. Provisional Patent Application No. 63/604,935 filed Dec. 1, 2023, U.S. Provisional Patent Application No. 63/623,279 filed Jan. 21, 2024, and U.S. Provisional Patent Application No. 63/567,174 filed Mar. 19, 2024, and all the benefits accruing therefrom under 35 U.S.C. § 119, the contents of which applications are incorporated herein in their entireties by reference.

SEQUENCE LISTING

The instant application contains a Sequence Listing which has been submitted electronically in XML file format and is hereby incorporated by reference in its entirety. Said XML copy, created on Mar. 28, 2025, is named 30116-US-CON_SL.xml and is 37,183 bytes in size.

FIELD OF THE INVENTION

The present invention relates to bifunctional molecules that contain a circulating protein-binding moiety linked through a linker group to a cellular receptor-binding moiety. Specifically, the present invention relates to bifunctional molecules containing a circulating protein-binding moiety that binds to galactose-deficient immunoglobulins.

BACKGROUND OF THE INVENTION

IgA nephropathy (IgAN) is a heterogeneous autoimmune disease characterized by (1) increased levels of circulating galactose-deficient IgA1 (Gd-IgA1) antibodies, (2) production of galactose-deficient IgA1-specific IgG antibodies, and (3) formation of circulating nephritogenic immune complexes composed of galactose-deficient IgA1 antibodies and a galactose-deficient IgA1-specific IgG antibodies. These immune complexes accumulate and are deposited in the glomerular mesangium and induce the mesangioproliferative glomerulonephritis characteristic of IgAN, a cause of kidney injury. Overproduction of galactose-deficient IgA1 and the formation of Gd-IgA1-IgG immune complexes are key drivers of this 4-hit pathogenic cascade. See Lai et al., Nature Rev. Dis. Primers, 2,16001 (2016). IgG is enriched for galactose-deficient IgA1-specific antibodies in renal immunodeposits of IgA neuropathy patients.

Serum levels of galactose-deficient IgA1 autoantigen and the corresponding autoantibodies were each found to correlate with IgAN severity and progression. Suzuki et al., J. Clin. Invest., 119(6), 1668-1677 (2009), which is incorporated herein in its entirety by reference.

Moldoveanu et al. provided in vivo evidence for the nephritogenic role of the IgG autoantibodies in IgAN. Moldoveanu et al., J. Autoimmun., 118, 102593 (2021). Immune complexes formed from galactose-deficient IgA and human IgG autoantibody injected intravenously into mice produced glomerular injury. The histopathological changes in the injured tissues were characteristic of IgAN. Exploratory kidney-transcriptome profiling indicated these immune complexes changed the gene expression of multiple pathways, consistent with the changes seen in kidney biopsies of patients with IgAN.

IgAN is the most common form of primary glomerulonephritis in the world and currently has no treatment. There remains a need for new medicines capable of treating or slowing down the progression of the disease.

SUMMARY OF THE INVENTION

The invention is directed to bifunctional molecules (agents) capable of binding and degrading galactose-deficient IgA1 (Gd-IgA1) immunoglobulins.

In one embodiment, the invention provides a composition of matter (an agent) comprising:

- a galactose-deficient IgA1 binding moiety,
- a cellular receptor-binding moiety that can bind to hepatocytes or other degrading cells through asialoglycoprotein receptors (ASGPR) of hepatocytes or other cell receptors on the surface degrading cells, e.g., in a patient or subject, and
- a linker moiety connecting the galactose-deficient IgA1 binding moiety and the cellular receptor-binding moiety, wherein the linker moiety can be a single peptide bond or a larger linker moiety.

In another embodiment, the binding moiety that can bind to a galactose-deficient IgA1 is an anti-human rat Km55 antibody, a Km55 variant, or an antigen-binding fragment thereof.

In another embodiment, the binding moiety that can bind to a galactose-deficient IgA1 is a polypeptide having complementary determining regions (CDRs) of the Km55 antibody. In a particular embodiment, the complementary determining regions include six CDRs according to the Kabat numbering scheme having the structures of SEQ ID NO: 9, SEQ ID NO: 10, SEQ ID NO: 11, SEQ ID NO: 12, SEQ ID NO: 13, and SEQ ID NO: 14.

In some embodiments, the invention provides a composition of matter (an agent) having a structure of:

$$R^{CN}—(Xaa)y—R^{CC},$$

[AGN101]

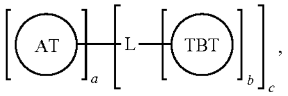

[AGN102]

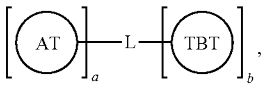

[AGN103]

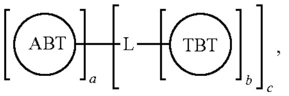

or

[AGN104]

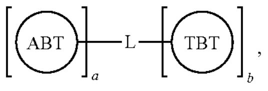

or a salt thereof.

In some embodiments, the invention provides a composition of matter (an agent) of formula AGN105:

[AGN105]

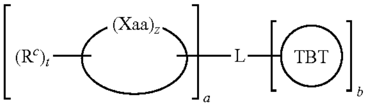

or a salt thereof, wherein the composition of matter has additional elements described in this specification.

In some embodiments, the invention provides a composition of matter comprising the formula AGN106:

[AGN106]

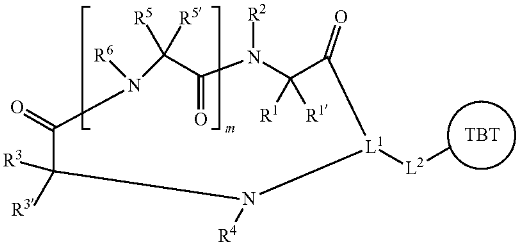

or a salt thereof, wherein the composition of matter has additional elements described in this specification.

In another embodiment, the cellular receptor-binding moiety comprises an ASGPR binding group according to the chemical structure:

[TBT101]

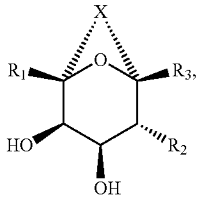

or

[TBT102]

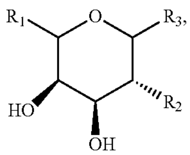

, wherein the cellular receptor-binding moiety has additional elements described in this specification.

In another embodiment, the invention provides a method of making a bifunctional composition of matter (agent) capable of binding and degrading galactose-deficient IgA1 (Gd-IgA1) immunoglobulins.

In another embodiment, the invention provides a method of removing galactose-deficient IgA1 in a patient or subject in need thereof by administering the agent to the patient or subject.

In another embodiment, the invention provides a method of making the composition of matter (agent).

In another embodiment, the invention provides a method of treating a disease state or condition associated with the upregulation of galactose-deficient IgA1 in a patient or subject in need by administering an effective amount of the agent to the patient or subject.

In another embodiment, the invention provides a composition including the agent and at least one additional agent comprising a moiety capable of binding to the antibody that forms the antibody moiety of the first compound.

In another embodiment, the invention provides a composition including the agent and at least one pharmaceutically acceptable excipient.

In one aspect, the composition of matter (agent) binds to galactose-deficient IgA but spares most non-defective IgA in the patient or subject. Lowering levels of circulatory galactose-deficient IgA1 and IgG: galactose-deficient IgA1 immune complexes can decrease mesangial deposition and improve kidney function.

In one aspect, the composition of matter (agent) has a balanced strength of binding (balanced binding) to the liver receptor by the TBT moiety as compared with the binding to the degalactosylated IgA antibody by the ABT moiety.

Several objects, features, aspects, and advantages of the invention will become more apparent from the following detailed description of embodiments of the invention, along with the drawings.

BRIEF DESCRIPTION OF THE DRAWINGS

For illustration, some embodiments of the invention are shown in the drawings described below. Like numerals in the drawings indicate like elements throughout. The invention is not limited to the precise arrangements, dimensions, and instruments shown.

DETAILED DESCRIPTION OF THE INVENTION

The following detailed description is provided to aid persons having ordinary skill in the biomedical art. Exemplary embodiments are described. These embodiments are only exemplary. This disclosure is not limited thereto but is defined by the scope of the appended claims. Persons having ordinary skill in the biomedical art may modify and vary the embodiments described without departing from the spirit or scope of this disclosure.

Industrial Applicability

The invention provides a medically useful composition of matter (agent) for treating or slowing down the progression of IgA nephropathy (IgAN).

Galactose-deficient IgA1 has attracted interest as a critical effector molecule in the pathogenesis and progression of IgA nephropathy (IgAN). Several O-link glycan-modified regions exist in the heavy chain hinge region of the human IgA1 molecule. See SEQ ID NO. 83. Galactose-deficient IgA1 circulates in the bloodstream of patients with the pathological condition of IgAN. The deposition of galactose-deficient IgA1 in glomeruli is involved in IgAN (multi-hit hypothesis of Gd-IgA1).

Figure 15:
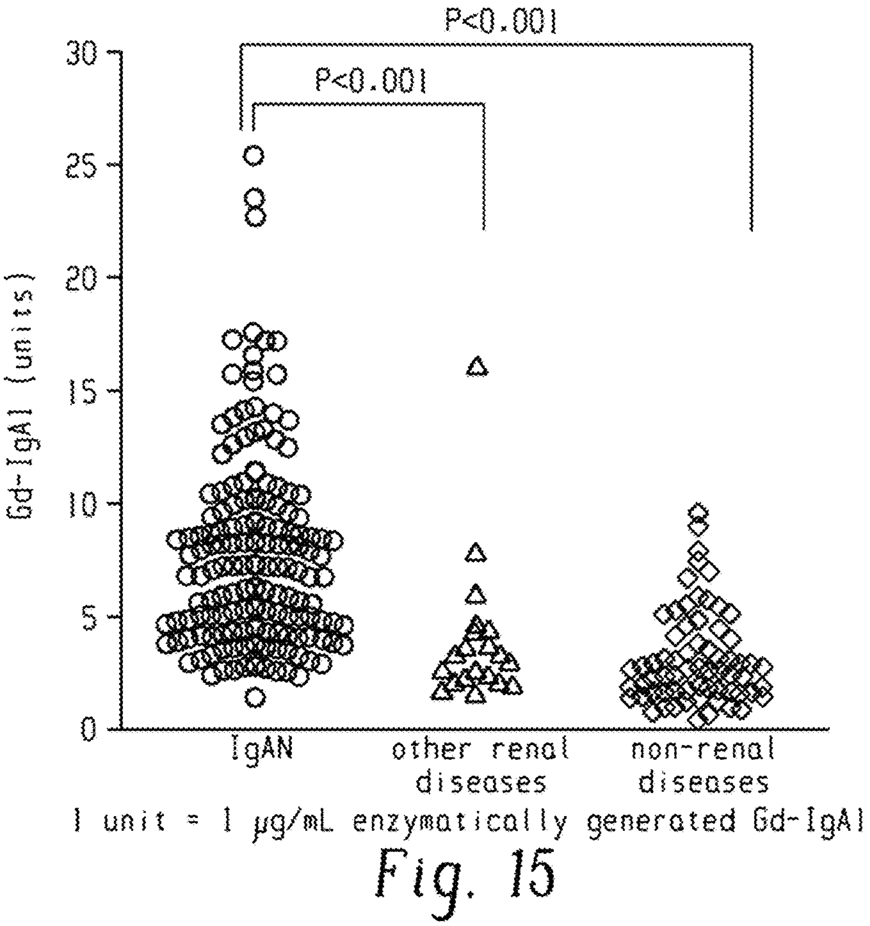
FIG. 15 is a chart from IBL-America, #27600, Pamphlet 2, showing Galactose-deficient IgA1 in serum. An ELISA assay using Km55 antibody specifically detects galactose-deficient IgA1.

The levels of galactose-deficient IGA in IgAN are significantly elevated compared with those of healthy subjects or patients with renal disease other than IgAN. The measuring system using *Helix aspersa* snail lectin (HAA) has been used in research studies and diagnostic procedures. A commercially available ELISA assay kit using the Km55 antibody has also been used in research studies and diagnostic procedures. See IBL-America, Minneapolis, MN, USA, 55432, Catalog Number: 10777. See also IBL-America, Code 27600 galactose-deficient IgA1 assay. An IHC protocol is provided with the assay kit. The Km55 antibody can detect galactose-deficient IgA1 in tissue by immunohistochemistry (IHC) technique differently from the feature of HAA lectin. Galactose-deficient IgA1 specifically exists in the glomeruli of patients with IgAN, as determined in research studies using this antibody. A drawing of one result of an assay using the assay kit is shown in FIG. 15.

Lowering levels of circulatory galactose-deficient IgA1 and IgG: galactose-deficient IgA1 immune complexes can decrease mesangial deposition and improve kidney function. Reduction of circulatory galactose-deficient IgA1 has been achieved using clinical-stage immunomodulatory BLyS/APRIL inhibitors, with potential improvements in proteinuria and kidney function. Barratt et al., Kidney Int. Rep., 7(8), 1831-1841 (2022). Selective protein degradation of circulatory galactose-deficient IgA1 and its complexes can stabilize or reverse the progression of IgAN without broad immunosuppression.

By contrast, the bifunctional composition of matter (agent) selectively binds to a galactose-deficient IgA1 in circulation to form a protein complex that binds a cellular receptor. The protein complex is endocytosed and degraded. Galactose-deficient IgA1 is eliminated from circulation by hepatocytes, macrophages, or another cell type, resulting in a lowered level of the galactose-deficient IgA1, potentially attenuating the IgAN symptoms. Galactose-deficient IgA1 may be eliminated, resulting in substantially reduced symptoms or even a cure or elimination of IgAN.

Non-glycosylated proteins, e.g., immunoglobulins, are not known to be natural targets for the ASGPR on hepatocytes and other degrading cells. The invention provides a bifunctional agent for degrading circulating galactose-deficient IgA1 that takes advantage of ASGPR as an entryway for proteins into the endosomal-lysosomal degradation pathway.

Proper protein synthesis, secretion, and turnover are necessary for maintaining homeostasis. Newly synthesized proteins targeted for secretion are first trafficked to the endoplasmic reticulum, where they are post-translationally modified with N-linked glycan chains terminating in sialic acids. N-acetyl-galactosamine is an endogenous ligand. As proteins age, terminal sialic acid residues are removed by circulating endogenous glycosidases. This natural protein aging process unmasks galactose and N-acetylgalactose (GalNAc) residues, which bind the asialoglycoprotein receptor (ASGPR) on the surface of hepatocytes. ASGPR is a C-type lectin that removes aged circulating proteins with exposed GalNAc residues from circulation by trafficking them to lysosomes. Multiple galactose or GalNAc residues displayed on the protein surface are necessary for high-affinity binding to and subsequent endocytosis by ASGPR. Avidity is gained with the incorporation of di-dentate or tri-dentate ligands.

After these proteins are endocytosed, they are released from the ASGPR through depletion of calcium from the endosome and changes in binding site amino acid protonation due to decreased pH; the ASGPR is recycled back to the hepatocyte surface. Endocytosed proteins are trafficked to late endosomes, which are fused with lysosomes. Lysosomal proteases then degrade endocytosed proteins, permanently removing them from circulation. See Caianiello et al., Nature Chemical Biology, 17(9), 947-953 (2021)

There is a need in the biomedical art for better treatments of IgAN nephropathy to replace or supplement the use of immunosuppressive agents for treating the symptoms of IgAN. See Agenix, Cochrane Database Syst Rev. 2020, 2020(3) CD003965 (Mar. 12, 2020).

The invention advantageously provides a therapeutic that has some or all of these features:

High aqueous solubility that supports intravenous or subcutaneous delivery (>100 mg/mL).

Good chemical stability in aqueous solutions at room temperature (t>days or weeks).

High stability in human plasma ($t_{1/2}$>120 minutes).

Rapid in vivo clearance driven by liver uptake and ASGPR pathway ($t_{1/2}$~30 minutes).

Degradation to innocuous metabolites in the liver.

Definitions

For convenience, the meaning of some terms and phrases used in the specification, examples, and appended claims are listed below. Unless stated otherwise or implicit from context, these terms and phrases shall have the meanings below. These definitions aid in describing particular embodiments but are not intended to limit the claimed invention.

As used in this application, except as otherwise expressly provided herein, each of these terms shall have the meaning set forth below. Additional definitions are set forth throughout the application. Where a term is not specifically defined, that term is given a biomedical art-recognized meaning, applying that term in context to its use in describing the invention.

The articles "a" and "an" have the plain meaning of one or more than one, i.e., at least one, of the grammatical object of the article unless the context indicates otherwise. For example, "an element" means one element or more than one element.

The term "ABT" has the biomedical art-recognized meaning of an antigen-binding moiety. In some embodiments of this specification, the ABT binds to galactose-deficient IgA1. In one embodiment, the ABT has a linker attachment point that does not diminish binding affinity.

The term "active Ingredient" has the United States Food & Drug Administration-provided meaning of any component that provides pharmacological activity or other direct effect in the diagnosis, cure, mitigation, treatment, or prevention of disease, or to affect the structure or any function of a human body or an animal body.

The term "ADCC" has the biomedical art-recognized meaning of antibody-dependent cell-mediated cytotoxicity, which is a mechanism of cell-mediated immune defense whereby an effector cell of the immune system kills a target cell whose membrane-surface antigens have been bound by specific antibodies.

The term "ADCP" has the biomedical art-recognized meaning of antibody-dependent cell-mediated phagocytosis, an immunological mechanism of elimination in which tumor cells are targeted with antibodies to promote their clearance from the body by phagocytic immune cells.

The term "agent" has the biomedical art-recognized meaning of a composition of matter useful for performing a function. The specification describes several useful biomedical functions.

The term "alleviate" has the biomedical art-recognized meaning of a process by which the severity of a sign or symptom of a disorder is decreased. A sign or symptom can be alleviated without being eliminated. The administration of compositions or pharmaceutical compositions of the invention may or can lead to the elimination of a sign or symptom. However, elimination is not required. Effective dosages should be expected to decrease the severity of a sign or symptom.

The terms "an effective amount" and "a therapeutically effective amount" have the biomedical art-recognized meaning of an amount effective to achieve its intended purpose. The effect can be detected by any assay method known in the art. The precise effective amount for a subject will depend on the subject's body weight, size, and health; the nature and extent of the condition; and the therapeutic or combination of therapeutics selected for administration. Therapeutically effective amounts for a situation can be determined by routine experimentation that is within the skill and judgment of the clinician. In embodiments, the disease or condition to be treated is tendinopathy.

The term "anti-galactose-deficient IgA1 (Gd-IgA1) antibody" has the biomedical art-recognized meaning of an antibody that selectively binds galactose-deficient IgA1. In several embodiments of the invention, the anti-galactose-deficient IgA1 antibody is the published Km55 antibody, a Km55 variant, or an antigen-binding fragment thereof.

The term "anti-galactose-deficient IgA1 (Gd-IgA1) IgG antibody" has the biomedical art-recognized meaning of an IgG antibody or a fragment thereof that binds to a galactose-deficient IgA1. In several embodiments of the invention, the anti-galactose-deficient IgA1 antibody is a published Km55 antibody, a Km55 variant, or an antigen-binding fragment thereof. In some embodiments, this specification describes a "glycan-specific IgG antibody-binding" as an anti-galactose-deficient IgA1: IgG antibody.

The term "antigen-binding fragment thereof" has the biomedical art-recognized meaning of (1) a fragment of an intact antibody that binds to the same antigen recognized by the full-length antibody, such as $F(ab')_2$, $F(ab)_2$, Fab', Fab, Fv, sFv, or other fragments consisting of the variable regions, or (2) any synthetic or genetically engineered protein that acts like an antibody by binding to a specific antigen to form a complex. The term antigen-binding part of an antibody encompasses single-chain antibodies.

The term "asialoglycoprotein receptor (ASGPR) binding group" has the biomedical art-recognized meaning of a binding group that binds to a hepatocyte asialoglycoprotein receptor. The ASGPR binding group selectively binds to hepatocyte asialoglycoprotein receptors on the surface of hepatocytes. In several embodiments of this specification, an ASGPR binding group is a component of a bifunctional agent as a cellular receptor-binding moiety covalently bound to the antibody-binding moiety through a linker group. Through this ASGPR moiety, bifunctional agents complexed with a circulating protein, e.g., galactose-deficient IgA1, bind to hepatocytes. After the bifunctional agent complexed with a circulating protein is bound to a hepatocyte or other cell, the circulating protein is taken into the hepatocyte or other cell via a phagocytosis mechanism, wherein the circulating protein is degraded through lysosomal degradation.

The term "asialoglycoprotein receptor (ASGPR) has the biomedical art-recognized meaning of lectins, which bind asialoglycoprotein and glycoproteins from which a sialic acid has been removed to expose galactose residues. These cellular receptors are located on mammalian hepatocytes and other cells, such as glandular cells of the gallbladder and the stomach. ASGPR removes target glycoproteins from circulation.

The term “at least one of,” when preceding a list of elements, modifies the entire list of elements and does not modify the individual elements of the list.

The term “AT” has the biomedical art-recognized meaning of an antibody moiety. In some embodiments of this specification, the AT binds to galactose-deficient IgA1.

The term “cellular receptor-binding moiety” has the biomedical art-recognized meaning. In several embodiments of this specification, the cellular receptor-binding moiety is an asialoglycoprotein receptor (ASGPR) binding group.

The term “cellular receptor” has the biomedical art-recognized meaning of a protein on the surface of a cell that binds to a compound, e.g., a ligand, e.g., a protein, in solution, or on another cell. Generally, ligand-receptor binding induces one or more biological responses. In this specification, an asialoglycoprotein receptor (ASGPR) is a cellular receptor on the surface of hepatocytes or other cells that binds to an asialoglycoprotein or a derivative thereof.

The term “chimerized” has the biomedical art-recognized meaning. Chimeric antibodies are made by fusing variable domains from one species, such as a mouse, with constant domains from another species, such as a human being. With such biotechnical manipulation, chimeric antibodies have the foreign antibody's antigen specificity and affinity.

The terms “combination therapy” and “co-therapy” have the biomedical art-recognized meaning of the administration of a composition described herein and at least a second agent as part of a specific treatment regimen intended to provide the beneficial effect from the co-action of these therapeutic agents. The beneficial effect of the combination may include but is not limited to, pharmacokinetic or pharmacodynamic co-action resulting from the combination of therapeutic agents. These therapeutic agents are typically administered in combination over a defined time (usually minutes, hours, days, or weeks, depending on the combination selected). The term combination therapy” includes the administration of the therapeutic agents in further combination with other biologically active ingredients and non-drug therapies, e.g., surgery or radiation treatment. Where the combination therapy further comprises a non-drug treatment, the non-drug treatment may be conducted at any suitable time if a beneficial effect from the co-action of the combination of the therapeutic agents is achieved. In appropriate cases, the beneficial effect is still achieved when the non-drug treatment is temporally removed from the administration of the therapeutic agents, perhaps by days or even weeks.

The term “complementarity determining region (CDR)” has the biomedical art-recognized meaning of a polypeptide region of an antibody heavy chin or an antibody light chain that is a determinant of the antibody to antigen binding. Each antibody heavy chain contains three complementarity determining regions. Each antibody light chain has three complementarity determining regions, usually different from the three CDRs on an antibody heavy chain. Persons having ordinary skill in the biomedical art calculate the using a standardized numbering method known as the Kabat numbering scheme. Kabat et al., Sequences of Proteins of Immunological Interest, 5th edition (Public Health Service, National Institutes of Health, Bethesda, MD., USA, 1991), although other numbering schemes such as Chothia and IMGT are also used by persons having ordinary skill in the biomedical art.

The term “comprises,” the term “comprising,” the term “includes,” and the term “including” specify stated features, regions, integers, steps, operations, elements, or components, but do not preclude the presence or addition of one or more other features, regions, integers, steps, operations, elements, components, or groups thereof.

The term “dd-IgA1” has the biomedical art-recognized meaning of desialylated and degalactosylated IgA1.

The term “Fc-III-4c” has the biomedical art-recognized meaning of a polypeptide region in the fragment crystallizable region (Fc region), the tail region, of an antibody.

The term “Fc-M” has the biomedical art-recognized meaning of a polypeptide region in the fragment crystallizable region (Fc region), the tail region, of an antibody.

The term “FcB-1” has the biomedical art-recognized meaning of a polypeptide region in the fragment crystallizable region (Fc region), the tail region, of an antibody.

The term “FcB-2” has the biomedical art-recognized meaning of a polypeptide region in the fragment crystallizable region (Fc region), the tail region, of an antibody.

The terms “first,” “second,” “third,” etc., have the plain meaning of describing several elements, components, regions, layers, or sections. These terms should not limit these elements, components, regions, layers, or sections. These terms are only used to distinguish one element, component, region, layer, or section from another element, component, region, layer, or section. A first element, component, region, layer, or section could be termed a second element, component, region, layer, or section without departing from the teachings of the present embodiments.

The term “Gal” has the biomedical art-recognized meaning of galactose.

The term “galactose-deficient IgA1 (Gd-IgA1) binding moiety” has the biomedical art-recognized meaning of a moiety on a binding protein, e.g., an IgG antibody or a fragment thereof, that binds to a galactose-deficient IgA1. In some embodiments described in this specification, a “glycan-specific IgG antibody-binding moiety” is a galactose-deficient IgA1 binding moiety on an IgG antibody, such as the published Km55 antibody, a Km55 variant, or an antigen-binding fragment thereof.

The term “GalNAc” has the biomedical art-recognized meaning of N-acetylgalactosamine.

The term “glomerular mesangium” has the biomedical art-recognized meaning of a component of the kidney glomerulus, forming the supporting framework in which the glomerular tuft capillaries ramify. The mesangium includes an extracellular matrix comprising Type IV collagen, proteoglycans, other proteins, and two cell types.

The term “HAA” has the biomedical art-recognized meaning of *Helix aspersa* agglutinin.

The term “hepatocyte has the biomedical art-recognized meaning of a cell of the main parenchymal tissue of the liver. Hepatocytes make up 55-65% of the liver's mass.

The term “hepatocyte” has the biomedical art-recognized meaning of a cell of the main parenchymal tissue of the liver. Hepatocytes make up 55-65% of the liver's mass.

The term “humanized” has the biomedical art-recognized meaning a protein, e.g., an antibody, is genetically engineered to closely resemble the polypeptide structure of the human homologue. A variable domain of an antibody of rodent origin can be fused to a constant domain of human origin, keeping the specificity of the rodent antibody. The domain of human origin need not originate directly from a human in that it is first synthesized in a human. Instead, human domains can be generated in rodents whose genome incorporates human immunoglobulin genes. The antibody can be partially or completely humanized. In one approach, four general steps are used to humanize a monoclonal antibody. These steps are (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

The term "IgA antibody" has the biomedical art-recognized meaning. Two molecules of IgA are joined and associated with a protein that enables the newly formed IgA molecule to be secreted across epithelial cells that line several ducts and organs.

The term "IgA nephropathy (IgAN)," also known as Berger disease, has the biomedical art-recognized meaning of the most common form of primary glomerulonephritis worldwide. The condition was named based on the pathologic characteristics of IgA deposition in the glomeruli. An estimated 15-20% of the patients with IgAN progress to end-stage renal disease within 20 years of the disease onset. Kuroyanagi et al., Galactose-deficient IgA1 is involved in IgA deposition in renal grafts biopsied one hour after kidney transplantation. *Intern Med*. (Oct. 26, 2022). The IgA in the mesangial deposits is exclusively from the IgA1 subclass and is aberrantly glycosyl with the hinge-region O-linked glycans being deficient in galactose (Gal). The IgA1 in the circulation of patients with IgAN also carries Gal-deficient O-glycans, although Gal-deficient variants are rarely found in the IgA1 in sera from normal individuals. The production of these variants is due to altered expression of specific glycosyltransferases in the IgA1-producing cells. The binding of IgA1-containing immune complexes with aberrantly glycosylated IgA1 to mesangial cells induces the renal manifestations characteristic of IgAN. See Suzuki et al., J. Clin. Invest., 119, 1668-1677 (2009).

The term "IgG" antibody has the biomedical art-recognized meaning. Each IgG molecule consists of the basic four-chain immunoglobulin structure—two γ (gamma) heavy chains and two identical light chains (either kappa or lambda)—and carries two identical antigen-binding sites. There are four subclasses of IgG, each with minor differences in its H chains but with distinct biological properties.

The term "IgG1" antibody has the biomedical art-recognized meaning of an IgG antibody, where the Ig gamma-1 chain C region is a protein encoded by the IGHG1 gene in humans.

The term "IgG2" antibody has the biomedical art-recognized meaning of an IgG antibody where the Ig gamma-2 chain C region is a protein that in humans is encoded by the IGHG2 gene.

The term "IgG4" antibody has the biomedical art-recognized meaning of an IgG antibody, where the Ig gamma-4 chain C region is a protein encoded by the IGHG4 gene in humans.

The term "IVIG" has the biomedical art-recognized meaning of administering intravenous immunoglobulin (IVIG).

The term "Km55" in this specification refers to a group of anti-galactose-deficient IgA1 antibodies. In some embodiments, Km55 may be the published Km55 antibody, a Km55 variant, or an antigen-binding fragment thereof. In some embodiments, Km55 may be chimerized, partially humanized, or humanized Km55 variants thereof, or an antigen-binding fragment thereof.

The term "linker moiety" has the biomedical art-recognized meaning of a moiety of a chemical compound that links one moiety of the chemical compound to another moiety of the same compound. In several embodiments of this invention, the linker moiety connects an anti-galactose-deficient IgA1 IgG antibody to a cellular receptor-binding moiety. In one embodiment, a linker is largely comprised of PEG units. In another embodiment, a linker is amenable to presenting multiple ASGPR binders. In another embodiment, a linker is long enough to accommodate ternary complex formation. See also U.S. Pat. Publ. 2020/0190165, describing cleavable linkers and cleavable parts of each of which is incorporated herein by reference.

The term "Markush group" has the patent law-recognized meaning.

The term "MODE" has the proprietary meaning of molecular degraders. See International Pat. Publ. WO 2019/199634 (Yale University) and WO 2019/199621 (Yale University).

The term "moiety" has the biomedical meaning of a defined chemical group or entity with a particular structure or activity.

The term "monotherapy" has the biomedical art-recognized meaning of administering a single active or therapeutic compound to a subject in need. Monotherapy usually is administering a therapeutically effective amount of an active composition.

The term "Multimodal Antibody Therapy Enhancers (MATE or MATES)" has the proprietary meaning. See International Pat. Publ. WO 2021/102052 (Kleo Pharmaceuticals).

The term "N-acetyl-D-galactosamine (GalNAc) moiety" has the biomedical art-recognized meaning.

The term "on" has the plain meaning. When an element is referred to as being "on" another element, it can be directly in contact with the other element, or intervening elements may be present therebetween. When an element is referred to as being "directly on" another element, no intervening elements are present.

The term "one or more" has the plain meaning. As used in this specification, in some embodiments, "at least one" or "one or more" is 1-1000, 1-500, 1-200, 1-100, 1-90, 1-80, 1-70, 1-60, 1-50, 1-40, 1-30, 1-20, 1-10, 1-5, or about 1, 2, 3, 4, 5, 6, 7, 8, 9, 10, 11, 12, 13, 14, 15, 16, 17, 18, 19, 20, or more. In some embodiments, it is one. In some embodiments, it is two or more. In some embodiments, it is about 3. In some embodiments, it is about 4. In some embodiments, it is about 5. In some embodiments, it is about 6. In some embodiments, it is about 7. In some embodiments, it is about 8. In some embodiments, it is about 9. In some embodiments, it is about 10. In some embodiments, it is about ten or more.

The term "or" as used herein means "or." The term "or" as used herein includes any combinations of one or more of the associated listed items.

The term "other degrading cells" has the biomedical art-recognized meaning. Asialoglycoprotein receptors (ASGPRs) are located on the glandular cells of the gallbladder and the stomach.

The term "partially humanized" has the biomedical art-recognized meaning that a protein, e.g., an antibody, is genetically engineered to resemble the polypeptide structure of the human homologue more closely. A variable domain of an antibody of rodent origin can be fused to a constant domain of human origin, keeping the specificity of the rodent antibody. The domain of human origin need not originate directly from a human in that it is first synthesized in a human. Instead, human domains can be generated in rodents whose genome incorporates human immunoglobulin genes. The antibody can be partially or completely humanized.

The term "pharmaceutically acceptable excipient" has the biomedical art-recognized meaning of an excipient that is useful in preparing a pharmaceutical composition that is generally safe, non-toxic, and neither biologically nor otherwise undesirable, and includes excipient that is acceptable for veterinary use and human pharmaceutical use. A "pharmaceutically acceptable excipient," as used in the specification and claims, includes both one and more than one such excipient. A thorough discussion of pharmaceutically acceptable excipients is available in Remington's Pharmaceutical Sciences, 23rd edition (Elsevier, 2020).

The term "pharmaceutically acceptable" has the biomedical art-recognized meaning of those compounds, anions, cations, materials, compositions, carriers, or dosage forms that are, within the scope of sound medical judgment, suitable for contact with the tissues of humans and animals without excessive toxicity, irritation, allergic response, or other problem or complication, commensurate with a reasonable benefit/risk ratio.

The term "production run" has the plain business meaning of the set of processes necessary to manufacture an individual batch or batches of a product of a pre-determined quantity. In business, a production run is conducted in accordance with a manufacturing plan to make a product for research and development or for clinical use. Production runs are a standard manufacturing process for producing products in large quantities. The purpose of production runs is to efficiently produce a consistent and high-quality output within a specific timeframe.

The term "protein-binding moiety" has the biomedical art-recognized meaning of a region of a chemical composition, e.g., a polypeptide region of a chemical composition, that specifically binds to a protein, e.g., a specific protein.

The term "rIgG" has the biomedical art-recognized meaning of recombinant human IgG.

The term "ROC" has the biomedical art-recognized meaning of receiver operating typical curve.

The terms "subject" and "patient" have the biomedical art-recognized meanings. The term patient includes human and other mammalian subjects that receive either prophylactic or therapeutic treatment.

The term "TBT" has the biomedical art-recognized meaning of a target-binding moiety, a cellular receptor-binding moiety. In some embodiments of this specification, the TBT binds to ASGPR.

The terms "treating" and "treat" have the biomedical art-recognized meaning of managing and caring for a patient to combat a disease, condition, or disorder. This treatment includes the administration of a composition described to alleviate the symptoms or complications of a disease, condition, or disorder or to eliminate the disease, condition, or disorder.

The term "universal antibody-binding moiety" has the biomedical art-recognized meaning of a polypeptide region of an antibody-binding protein that binds a class of antibodies rather than a specific set of antibodies.

The term "UP/Cr" has the biomedical art-recognized meaning of urinary protein/urinary creatinine (ratio).

Some embodiments are described below by referring to structures and schemes to explain parts of the description.

Unless otherwise defined, all technical and scientific terms used have the same meaning as commonly understood by persons having ordinary skill in the biomedical art. The terminology used in the description is for describing particular embodiments only and is not intended to be limiting. The terms, such as those defined in commonly used dictionaries, should be interpreted as consistent with their meaning in the relevant art and the present disclosure. They should not be interpreted in an idealized or overly formal sense unless expressly so defined.

This specification does not concern a process for cloning humans, methods for changing the germ line genetic identity of humans, uses of human embryos for industrial or commercial purposes, or procedures for changing the genetic identity of animals likely to cause them suffering with no substantial medical benefit to humans or animals resulting from such processes.

Methods of Diagnosing IgA Nephropathy.

Previously, the diagnosis of IgAN was complicated because it often required renal biopsy, which may cause deadly complications.

Increasing evidence has indicated that galactose-deficient IgA is a trigger factor for the pathogenesis of IgAN. High levels of galactose-deficient IgA1 were reported to be associated with the disease progression. Zhang et al., Kidney Blood Pressure Res., 44, 1196-1206 (2019).

Although many researchers measured serum levels of galactose-deficient IgA using snail *Helix aspersa* agglutinin (HAA) lectin-based assay, the lectin-dependent assay needed to be more robust.

More recently, a more robust and stable enzyme-linked immunosorbent assay (ELISA) method was developed that uses the Km55 antibody to recognize a hinge region in human galactose-deficient IgA (Gd-IgA1 ELISA). Km55 has a high affinity towards galactose-deficient IgA and has been a diagnostic tool for detecting IgAN. Yasutake et al., Nephrol. Dial. Transplant., 30, 1315-1321 (2015). See also Japanese Pat. Publ. JP 2010-285419 published Dec. 24, 2010, and International Pat. Publ. WO 2015/064348 published May 7, 2015, each of which publication is incorporated herein in its entirety by reference.

Methods of Removing Galactose-Deficient IgA1 Antibody from a Patient or Subject.

The inventors conceived that reducing galactose-deficient IgA levels in IgAN patients results in disease treatment. The reduction of galactose-deficient IgA1 in subjects predisposed to IgAN may prevent disease. Towards this goal, the inventors designed and developed multifunctional degraders of galactose-deficient IgA1 that incorporate a galactose-deficient IgA1 binding moiety, such as a Km55 variant, and a cellular receptor-binding moiety with affinity to hepatocytes and other liver degrading cells. Galactose-deficient IgA1 bound through the anti-galactose-deficient IgA1 binding moiety is then delivered to the liver-degrading cells, where it is internalized and degraded through asialoglycoprotein receptors (ASGPR), or other cell receptors located on the surface of hepatocytes or other degrading cells in a patient or subject.

Method of Administration.

In one embodiment, the method of administration is by subcutaneous administration to a patient or subject of 50 mg/ml of the composition of matter (agent) for five to seven days. In a more specific embodiment, the composition of matter (agent) is AGN03A.

Methods of Measuring the Removal of Galactose-Deficient IgA1 Antibody from a Patient or Subject.

Guidance as to how much the administration of the agents of the invention to a patient or subject decreases IgA levels in the patient or subject is provided by several publications, e.g., Nihei, Suzuki, & Suzuki, Current understanding of IgA antibodies in the pathogenesis of IgA nephropathy. *Front. Immunol.,* 14, 1165394 (2023). Lectin-spectrometry and mass-spectrometry-based analyses showed that IgAN patients showed elevated serum levels of aberrantly glycosylated, specifically galactose-deficient, IgA1 in O-linked glycans of its hinge region. Over 70% of patients with IgAN showed increased serum galactose-deficient IgA1 levels above the 90th percentile in healthy controls. Moldoveanu et al., Kidney International, 71(11), 1148-54 (2007) showed that lectin from *Helix aspersa*, recognizing N-acetylgalactosamine, was used to develop an enzyme-linked immunosorbent assay that measures galactose-deficient IgA1 in serum. The median serum lectin-binding IgA1 level was significantly higher for patients with IgA nephropathy without progression to end-stage renal disease as compared with that for healthy adult controls. The sensitivity as a diagnostic test was 76.5%, with a specificity of 94%; the positive predictive value was 88.6%, and the negative predictive value was 78.9%.

Statistical Analyses.

Normal distribution quantitative variables can be expressed as means and SDs and compared by an independent-sample t-test, as was done by Zhang et al. (October 2019). The inventors used median and interquartile ranges for non-normally distributed variables and analyzed them with the Mann-Whitney U test. Categorical data was summarized by percentages. A two-sided p-value <0.05 was considered statistically significant. All statistical tests were performed using SPSS version 16.0.

The Chemical Structure of the Composition of Matter (Agent).

In an embodiment, the invention composes matter (agent) comprising:

- an anti-galactose-deficient IgA1 binding moiety,
- a cellular receptor-binding moiety that binds to hepatocytes or other degrading cells through asialoglycoprotein receptors (ASGPR) of hepatocytes or other cell receptors on the surface degrading cells in a patient or subject, and
- a linker moiety linking the antibody moiety and the cellular receptor-binding moiety.

In some embodiments, the invention composes matter (an agent) having a structure selected from the Markush group of structures consisting of:

$R^{CN}$—(Xaa)$y$—$R^{CC}$,

[AGN101]

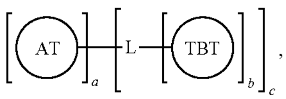

,

[AGN102]

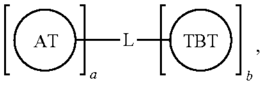

,

[AGN103]

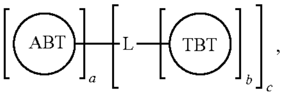

, or

-continued

[AGN104]

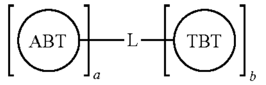

or a salt thereof. In these structures, a, b, and c may independently be an integer of 1 or greater. In some embodiments, each cellular receptor-binding moiety independently has the structure of —($R^{CN}$—(Xaa)y-$R^{CC}$) or salt form thereof.

In some embodiments, the invention composes matter (an agent) of formula AGN105:

[AGN105]

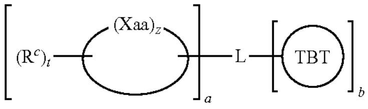

or a salt thereof, wherein:

each Xaa is independently a residue of an amino acid or an amino acid analog;

t is 0-50;

z is 1-50;

L is a linker moiety;

TBT is a cellular receptor-binding moiety;

each $R^c$ is independently -$L^a$-R';

each of a and b is independently 1-200;

each $L^a$ is independently a covalent bond, or an optionally substituted bivalent group selected from a $C_1$-$C_{20}$ aliphatic group or a $C_1$-$C_{20}$ heteroaliphatic group having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent monocyclic, bicyclic, or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus, and silicon, and a 3-20 membered heterocyclyl ring having 1-10 heteroatoms independently selected from oxygen, nitrogen, sulfur, phosphorus, and silicon;

each R' is independently —R, —C(O)R, —$CO_2$R, or —$SO_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus, and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus, and silicon, and 3-30 membered heterocyclyl having 1-10 heteroatoms independently selected from oxygen, nitrogen, sulfur, phosphorus, and silicon, or two R groups are optionally and independently taken together to form a covalent bond, or:

two or more R groups on the same atom are optionally and independently taken with the atom to form an optionally substituted, 3-30 membered, monocyclic, bicyclic, or polycyclic ring having, in addition to the atom, 0-10 heteroatoms independently selected from oxygen, nitrogen, sulfur, phosphorus, and silicon; or two or more R groups on two or more atoms are optionally and independently taken with their intervening atoms to form an optionally substituted, 3-30 membered, monocyclic, bicyclic, or polycyclic ring having, in addition to the intervening atoms, 0-10 heteroatoms independently selected from oxygen, nitrogen, sulfur, phosphorus, and silicon.

In some embodiments, a is 1. In some embodiments, b is 3. In some embodiments, a is 1 and b is 3, and a composition of matter of formula AGN107 has the structure of

[AGN107]

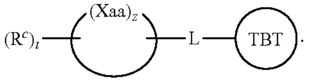

The Anti-Galactose-Deficient IgA1 Binding Moiety

The anti-galactose-deficient IgA1 binding moiety can be the published Km55 antibody, a Km55 variant, or an antigen-binding fragment thereof. The moiety may be a partially humanized galactose-deficient IgA1 antibody Km55 or an antigen-binding fragment thereof. The moiety may be a chimerized galactose-deficient IgA1 antibody Km55 or an antigen-binding fragment thereof.

In some embodiments, the galactose-deficient IgA1 binding moiety comprises a moiety selected from the Markush group consisting of one or more amino acid residues, a peptide moiety, a cyclic peptide moiety, a peptide comprising one or more natural amino acid residues, and a peptide comprising one or more unnatural natural amino acid residues.

The galactose-deficient IgA1 binding moiety may be or may comprise:

[ABT101]

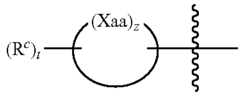

or a salt form thereof.

In some embodiments, ABT101 is a galactose-deficient IgA1 binding moiety. Each galactose-deficient IgA1 binding moiety in an agent may be of the same galactose-deficient IgA1 binding moiety or a salt thereof.

The Anti-Galactose-Deficient IgA1 Binding Moiety as a Universal Antibody-Binding Moiety.

In some embodiments, ABT101 is a universal antibody-binding moiety. In some embodiments, ABT101 is a universal antibody-binding moiety that can bind to glycan-specific IgG antibodies having different Fab regions. In some embodiments, ABT101 is a universal antibody-binding moiety that binds to an Fc region, e.g., the Fc region that binds to an Fc receptor.

Galactose-Deficient IgA1 Binding Moiety.

In some embodiments, a galactose-deficient IgA1 binding moiety, e.g., a galactose-deficient IgA1 binding moiety having the structure of ABT101, has the structure of

[ABT102]

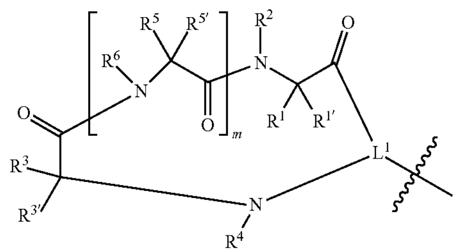

or

[ABT103]

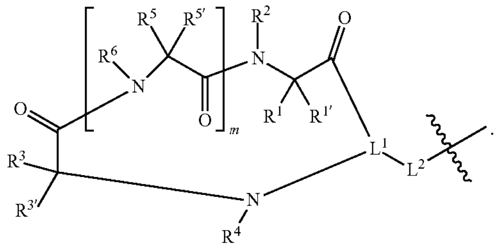

Other Embodiments of the Agent

In some embodiments, the invention composes matter comprising the formula AGN106:

[AGN106]

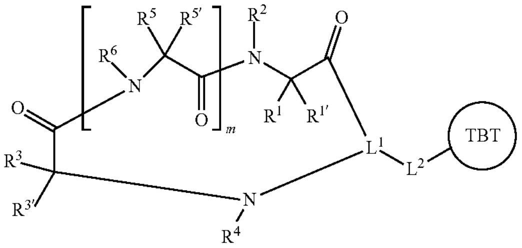

or a salt thereof, wherein:

each of $R^1$, $R^3$ and $R^5$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

$R^1$ and $R^{1'}$ are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

$R^3$ and $R^{3'}$ are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

an $R^5$ group and the $R^{5'}$ group attached to the same carbon atom are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur; or two $R^5$ groups are optionally taken with their intervening atoms to form a $C_{1-10}$ optionally substituted bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R) C(O)—, —S(O)—, $—S(O)_2—$, or $-Cy^1-$, wherein each $-Cy^1-$ is independently a 5-6 membered heteroarylenyl with 1-4 heteroatoms independently selected from nitrogen, oxygen or sulfur;

each of $R^{1'}$, $R^{3'}$ and $R^{5'}$ is independently hydrogen or optionally substituted $C_{1-3}$ aliphatic;

each of $R^2$, $R^4$ and $R^6$ is independently hydrogen, or optionally substituted $C_{1-4}$ aliphatic, or:

$R^2$ and $R^1$ are optionally taken with their intervening atoms to form a 4-8 membered, optionally substituted saturated or partially unsaturated monocyclic heterocyclic ring having 1-2 heteroatoms independently selected from nitrogen, oxygen, or sulfur;

$R^4$ and $R^3$ are optionally taken with their intervening atoms to form a 4-8 membered optionally substituted saturated or partially unsaturated monocyclic heterocyclic ring having 1-2 heteroatoms independently selected from nitrogen, oxygen, or sulfur; or an $R^6$ group and its adjacent $R^5$ group are optionally taken with their intervening atoms to form a 4-8 membered optionally substituted saturated or partially unsaturated monocyclic heterocyclic ring having 1-2 heteroatoms independently selected from nitrogen, oxygen, or sulfur;

$L^1$ is a trivalent linker moiety that connects

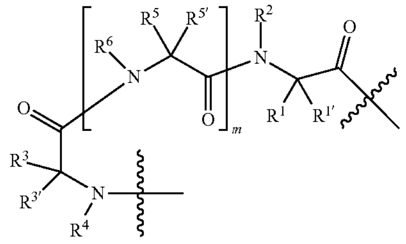

and;

$L^2$ is a covalent bond or a $C_{1-30}$ optionally substituted bivalent straight or branched saturated or unsaturated hydrocarbon chain wherein 1-10 methylene units of the chain are independently and optionally replaced with —S—, —N(R)—, —O—, —C(O)—, —OC(O)—, —C(O)O—, —C(O)N(R)—, —N(R) C(O)—, —S(O)—, $—S(O)_2—$, $—(CH_2OCH_2)_n—$, $—(OCH_2CH_2)_n—$, or $-Cy^1-$, wherein each $-Cy^1-$ is independently a 5-6 membered heteroarylenyl with 1-4 heteroatoms independently selected from nitrogen, oxygen or sulfur;

TBT is a cellular receptor-binding moiety; and each of m and n is independently 1, 2, 3, 4, 5, 6, 7, 8, 9, or 10.

Other embodiments use the components described in Intl. Pat. Publ. WO 2019/023501.

In some embodiments, the invention provides an agent comprising:

an antibody moiety, a cellular receptor-binding moiety, and a linker moiety (optionally a single peptide linkage) linking an antibody moiety and a cellular receptor-binding moiety.

In some embodiments, the agent has the structure of formula AGN101:

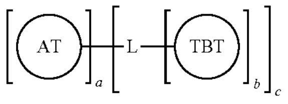

[AGN101] or a salt thereof, wherein:

each of a, b, and c is independently 1-200;

each AT is independently a galactose-deficient IgA1 binding moiety;

L is a linker moiety; and each TBT is independently a cellular receptor-binding moiety, wherein the galactose-deficient IgA1 binding moiety is a Km55 antibody, a Km55 variant, or an antigen-binding fragment thereof.

In some embodiments, the agent has the structure of formula AGN102:

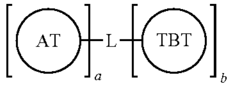

[AGN102] or a salt thereof, wherein:

each of a and b is independently 1-200;

each AT is independently a galactose-deficient IgA1 binding moiety;

L is a linker moiety; and each TBT is independently a cellular receptor-binding moiety, wherein the galactose-deficient IgA1 binding moiety is a Km55 antibody, a Km55 variant, or an antigen-binding fragment thereof.

In some embodiments, an agent comprises one and no more than one galactose-deficient IgA1 binding moiety. In some embodiments, one or no more than one galactose-deficient IgA1 binding moiety is bound to a linker moiety. In some embodiments, a is 1. In some embodiments, an agent comprises two or more glycan-specific IgG antibody moieties. In some embodiments, two or more glycan-specific IgG antibody moieties are bound to a single linker moiety. In some embodiments, a is 2 or more. In some embodiments, one and no more than one cellular receptor-binding moiety is bonded to a linker moiety. In some embodiments, b is 1. In some embodiments, two or more cellular receptor-binding moieties are bonded to a single linker moiety. In some embodiments, b is 2 or more. In some embodiments, an agent comprises one and no more than one cellular receptor-binding moiety. In some embodiments, c is 1. In some embodiments, b is 1 and c is 1. In some embodiments, a is 1, b is 1 and c is 1. In some embodiments, an agent comprises two or more target-binding moieties. In some embodiments, b is 2 or more and c is 1. In some embodiments, b is 2 or more and c is 2 or more. In some embodiments, b is 1 and c is 2 or more.

In some embodiments, c is 1-20, e.g., 1, 2, 3, 4, 5, 6, 7, 8, 9, 10, 11, 12, 13, 14, 15, 16, 17, 18, 19, or 20. In some embodiments, c is selected from the Markush group of size ranges, where c is 1-15, c is 1-10, c is 1-9, c is 1-8, c is 1-7, c is 1-6, c is 1-5, c is 1-4, c is 1-3, and c is 1-2. In some embodiments, c is a size selected from the Markush group of sizes consisting of 1, 2, 3, 4, 5, 6, 7, 8, and 9.

In some embodiments, each cellular receptor-binding moiety in an agent is the same. In some embodiments, each linker moiety connecting a cellular receptor-binding moiety to an antibody moiety is the same. In some embodiments, the TBTs in an agent are the same. In some embodiments, the several $\text{-L-(TBT)}_b$ are the same.

In some embodiments, b is 1. In some embodiments, c is 1. In some embodiments, c is two or more. In some embodiments, c is 2. Persons having ordinary skill in the biomedical art know that several technologies can conjugate antibody moieties with target-binding moieties, e.g., certain technologies used for preparing antibody-drug conjugates under the present disclosure. In some embodiments, target-binding moieties are connected to antibody moieties through certain types of groups or amino acid residues. In some embodiments, target-binding moieties are connected to lysine residues optionally through linker moieties. In some embodiments, target-binding moieties are connected to cysteine residues optionally through linker moieties. In some embodiments, target-binding moieties are connected to unnatural amino acid residues optionally through linker moieties. In some embodiments, the invention provides technologies for selectively linking target-binding moieties to particular amino acid residues optionally through linker moieties. In some embodiments, provided technologies selectively connect target-binding moieties to certain types of amino acid residues, e.g., lysine residues, optionally through linker moieties. In some embodiments, provided technologies selectively connect target-binding moieties to particular sites of antibody moieties, optionally through linker moieties. In some embodiments, provided technologies selectively connect target-binding moieties to certain types of amino acid residues at particular sites, optionally through linker moieties. In some embodiments, target-binding moieties are connected to K246 and K248 of an IgG1 heavy chain and amino acid residues corresponding thereto optionally through linker moieties. In some embodiments, target-binding moieties are connected to K251 and K253 of an IgG2 heavy chain and amino acid residues corresponding thereto, optionally through linker moieties. In some embodiments, target-binding moieties are connected to K239 and K241 of an IgG4 heavy chain and amino acid residues corresponding thereto optionally through linker moieties. In some embodiments, a cellular receptor-binding moiety is connected to a particular amino acid residue or site optionally through a linker. In some embodiments, each cellular receptor-binding moiety is independently connected to a particular amino acid residue or site optionally through a linker.

As known by persons having ordinary skill in the biomedical art, an antibody agent may comprise more than one particular site, e.g., one on each of the more than one chain, e.g., one or each heavy chain. In some embodiments, an antibody moiety comprises two heavy chains and one or both of the amino acid residues or amino acid residues corresponding thereto are each independently connected to a cellular receptor-binding moiety optionally through a linker. In some embodiments, one and no more than one is connected. In some embodiments, c is 1. In some embodiments, both are connected. In some embodiments, c is 2. In some embodiments, both target-binding moieties or both linker moieties (if any) are the same.

Antibody-Binding Moieties

Several antibody-binding moieties, including universal antibody-binding moieties, can be used under the teachings of this specification. Certain antibody-binding moieties and technologies for identifying or assessing antibody-binding moieties are described in WO 2019/023501 and WO 2019/136442, each of which is incorporated herein in its entirety by reference. Persons having ordinary skill in the biomedical art know that additional technologies in the biomedical art may be suitable for identifying or assessing antibody-binding moieties under the present disclosure. In some embodiments, an antibody-binding moiety comprises one or more amino acid residues, each independently natural or unnatural.

In some embodiments, a galactose-deficient IgA1 binding moiety, e.g., a protein-binding moiety, e.g., an antibody-binding moiety, e.g., a universal antibody-binding moiety, has the structure of or a salt form thereof, wherein:

- each of $R^1$, $R^3$ and $R^5$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:
- $R^1$ and $R^{1'}$ are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;
- $R^3$ and $R^{3'}$ are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;
- an $R^5$ group and the $R^{5'}$ group attached to the same carbon atom are optionally taken with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur; or
- two $R^5$ groups are optionally taken with their intervening atoms to form a $C_{1-10}$ optionally substituted bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R) C(O)—, —S(O)—, —$S(O)_2$—, or -$Cy^1$-, wherein each -$Cy^1$- is independently a 5-6 membered heteroarylenyl with 1-4 heteroatoms independently selected from nitrogen, oxygen or sulfur;

each of $R^{1'}$, $R^{3'}$ and $R^{5'}$ is independently hydrogen or optionally substituted $C_{1-3}$ aliphatic;

each of $R^2$, $R^4$ and $R^6$ is independently hydrogen, or optionally substituted $C_{1-4}$ aliphatic, or:

$R^2$ and $R^1$ are optionally taken with their intervening atoms to form a 4-8 membered, optionally substituted saturated or partially unsaturated monocyclic heterocyclic ring having 1-2 heteroatoms independently selected from nitrogen, oxygen, or sulfur;

$R^4$ and $R^3$ are optionally taken with their intervening atoms to form a 4-8 membered optionally substituted saturated or partially unsaturated monocyclic heterocyclic ring having 1-2 heteroatoms independently selected from nitrogen, oxygen, or sulfur; or an $R^6$ group and its adjacent $R^5$ group are optionally taken with their intervening atoms to form a 4-8 membered optionally substituted saturated or partially unsaturated monocyclic heterocyclic ring having 1-2 heteroatoms independently selected from nitrogen, oxygen, or sulfur;

$L^1$ is a trivalent linker moiety; and each of m and n is independently 1, 2, 3, 4, 5, 6, 7, 8, 9, 10, 11, 12, 13, 14, 15, 16, 17, 18, 19, or 20.

In some embodiments, $L^1$ is an optionally substituted trivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—. In some embodiments $L^1$ is —$(CH_2CH_2O)_{2-4}$— or —$(CH_2CH_2O)_2$—.

In some embodiments, a galactose-deficient IgA1 binding moiety, e.g., a protein-binding moiety, e.g., an antibody-binding moiety, e.g., a universal antibody-binding moiety, has the structure of or a salt form thereof, wherein:

each of $R^7$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

an $R^7$ group and the $R^{7'}$ group attached to the same carbon atom are optionally taken with their intervening carbon atom to form a 3-8 membered optionally substituted saturated or partially unsaturated spirocyclic carbocyclic ring or a 3-8 membered optionally substituted saturated or partially unsaturated spirocyclic heterocyclic ring having 1-2 heteroatoms independently selected from nitrogen, oxygen, or sulfur;

each of $R^{7'}$ is independently hydrogen or optionally substituted $C_{1-3}$ aliphatic;

each of $R^8$ is independently hydrogen, or optionally substituted $C_{1-4}$ aliphatic, or:

an $R^8$ group and its adjacent $R^7$ group are optionally taken with their intervening atoms to form a 4-8 membered optionally substituted saturated or partially unsaturated monocyclic heterocyclic ring having 1-2 heteroatoms independently selected from nitrogen, oxygen, or sulfur; and $R^9$ is hydrogen, optionally substituted $C_{1-3}$ aliphatic, or —C(O)—.

In some embodiments, a galactose-deficient IgA1 binding moiety, e.g., a universal antibody-binding moiety is or comprises a peptide moiety, e.g., a moiety having the structure of $R^c$—(Xaa)z- or a salt form thereof, wherein each of $R^c$, z and Xaa is independently as described herein. One or more Xaa may be independently an unnatural amino acid residue. Side chains of two or more amino acid residues may be linked to form bridges. Side chains of two cysteine residues may form a disulfide bridge comprising —S—S—, which, as in many proteins, can be formed by two —SH groups.

In some embodiments, a galactose-deficient IgA1 binding moiety, e.g., a protein-binding moiety, e.g., an antibody-binding moiety, e.g., a universal antibody-binding moiety, is or comprises a cyclic peptide moiety, e.g., a moiety having the structure of or a salt form thereof, wherein:

each Xaa is independently a residue of an amino acid or an amino acid analog;

t is 0-50;

z is 1-50;

each $R^c$ is independently -$L^a$-R';

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N(R')$—, —C(O)S—, or —C(O)O—;

each -Cy- is independently an optionally substituted bivalent monocyclic, bicyclic, or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus, and silicon, and a 3-20 membered heterocyclyl ring having 1-10 heteroatoms independently selected from oxygen, nitrogen, sulfur, phosphorus, and silicon;

each R' is independently —R, —C(O)R, —$CO_2R$, or —$SO_2R$;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus, and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus, and silicon, and 3-30 membered heterocyclyl having 1-10 heteroatoms independently selected from oxygen, nitrogen, sulfur, phosphorus, and silicon, or two R groups are optionally and independently taken together to form a covalent bond, or:

two or more R groups on the same atom are optionally and independently taken with the atom to form an optionally substituted, 3-30 membered, monocyclic, bicyclic, or polycyclic ring having, in addition to the atom, 0-10 heteroatoms independently selected from oxygen, nitrogen, sulfur, phosphorus, and silicon; or two or more R groups on two or more atoms are optionally and independently taken with their intervening atoms to form an optionally substituted, 3-30 membered, monocyclic, bicyclic, or polycyclic ring having, in addition to the intervening atoms, 0-10 heteroatoms.

In some embodiments, the heteroatom is independently selected from oxygen, nitrogen, sulfur, phosphorus, and silicon.

MATES

As used herein, the term "MATE" refers to Multimodal Antibody Therapy Enhancer. This next-generation antibody conjugation technology enables site-directed pairing with therapeutic monoclonal antibodies (mAbs), or therapeutic immunoglobulin (IG) pooled from donors. Persons having ordinary skill in the biomedical art can use MATES materials and methods as guidance to predictable results when making and using the invention:

This agent can be a MATE agent or MATE. The MATE agents are described, for example, in International Application No. PCT/US2020/061127, filed Nov. 18, 2020, the content of which is incorporated herein in its entirety by reference. In some embodiments, an agent comprises an antibody moiety, a cellular receptor-binding moiety, and a linker moiety linking an antibody moiety and a cellular receptor-binding moiety.

The galactose-deficient IgA1 binding moiety may be configured to bind to a galactose-deficient IgA1. In an embodiment, the galactose-deficient IgA1 binding moiety may be a recombinant IgG antibody moiety (rIgG). In another embodiment, the galactose-deficient IgA1 binding moiety may be isolated from sera of an IgA nephropathy patient. In another embodiment, the galactose-deficient IgA1 binding moiety may be a chimerized Km55 or an antigen-binding fragment thereof. In another embodiment, the galactose-deficient IgA1 binding moiety may be a partially humanized galactose-deficient IgA1 antibody Km55 or an antigen-binding fragment thereof. In another embodiment, the galactose-deficient IgA1 binding moiety may be the Km55 antibody described in Yasutake et al., Nephrol. Dial. Transplant., 30, 1315-1321 (2015).

Galactose-Deficient IgA1 Binding Moiety

In some embodiments, a galactose-deficient IgA1 binding moiety is or comprises $R^c$—(Xaa)z- or a salt form thereof, wherein each variable is as described herein. In some embodiments, a galactose-deficient IgA1 binding moiety is or comprises

[ABT101]

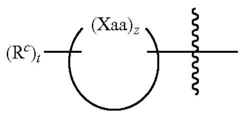

or a salt form thereof, wherein each variable is as described herein.

In some embodiments, a protein-binding moiety comprises $R^c$-(Xaa)z- or a salt form thereof, wherein each variable is as described herein. In some embodiments, a protein-binding moiety is or comprises ABT101 or a salt form thereof, wherein each variable is as described herein.

In some embodiments, a galactose-deficient IgA1 binding moiety, e.g., a universal antibody-binding moiety, is or comprises $R^c$-(Xaa)z- or a salt form thereof, wherein each variable is as described herein. In some embodiments, a galactose-deficient IgA1 binding moiety, e.g., a universal antibody-binding moiety, is or comprises ABT101 or a salt form thereof, wherein each variable is as described herein. In some embodiments, a galactose-deficient IgA1 binding moiety, e.g., a universal antibody-binding moiety, is Rc-(Xaa)z- or ABT101, or a salt form thereof and is or comprises a peptide unit.

In some embodiments, —(Xaa)z- is or comprises a peptide unit.

In some embodiments, amino acid residues may form bridges, e.g., connections formed by side chains optionally through linker moieties, e.g., L). As in many polypeptides, cysteine residues may form disulfide bridges.

In some embodiments, a peptide unit comprises an amino acid residue, e.g., at physiological pH about 7.4 (positively charged amino acid residue, $Xaa^p$), e.g., a residue of an amino acid of formula:

$NH(R^{a1})-L^{a1}-C(R^{a2})(R^{a3})-L^{a2}-COOH$ [LNK101]

with a positively charged side chain, lysine (Lys, K), arginine (Arg, R), and histidine (His, H) (basic side chains). In some embodiments, a peptide unit comprises R. In embodiments, at least one Xaa is R.

In some embodiments, a peptide unit comprises a functional group in an amino acid residue that can react with a functional group of another amino acid residue. In some embodiments, a peptide unit comprises an amino acid residue with a side chain which comprises a functional group that can react with another functional group of the side chain of another amino acid residue to form a linkage, e.g., see moieties described in TABLE 1. In some embodiments, one functional group of one amino acid residue is connected to a functional group of another amino acid residue to form a linkage (or bridge. Linkages are bonded to backbone atoms of peptide units and comprise no backbone atoms. In some embodiments, a peptide unit comprises a linkage formed by two side chains of non-neighboring amino acid residues. In some embodiments, a linkage is bonded to two backbone atoms of two non-neighboring amino acid residues. In some embodiments, both backbone atoms bonded to a linkage are carbon atoms.

In some embodiments, a galactose-deficient IgA1 binding moiety comprises an optionally substituted moiety of TABLE 2. In some embodiments, a protein-binding moiety is or comprises an optionally substituted moiety of TABLE 2. In some embodiments, a galactose-deficient IgA1 binding moiety, e.g., a universal antibody-binding moiety, is or comprises an optionally substituted moiety of TABLE 2. In some embodiments, a galactose-deficient IgA1 binding moiety is selected from TABLE 2. In some embodiments, a protein-binding moiety is selected from TABLE 2. In some embodiments, a galactose-deficient IgA1 binding moiety, e.g., a universal antibody-binding moiety, is selected from TABLE 2. In some embodiments, the C-terminus or N-terminus are optionally capped, e.g., for the C-terminus, by converting —COOH into $—C(O)N(R')_2$ like $—C(O)NH_2$; for N-terminus, by adding R'C(O)— like $CH_3C(O)$— to an amino group.

TABLE 2
| Exemplary binding moieties |
|---|
| 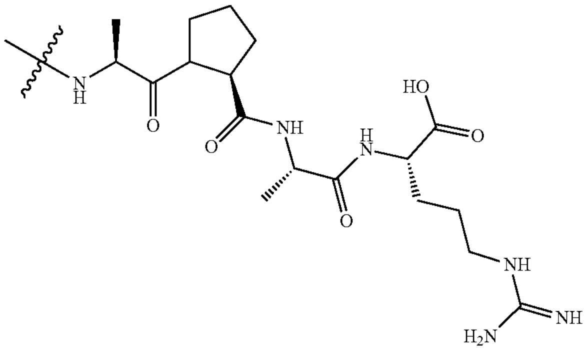 [SMILES: *N[C@@H](C)C(=O)C1CCC[C@H]1C(=O)N[C@@H](C)C(=O)N[C@@H](CCCNC(=N)N)C(=O)O] |
| ABT201 |
| 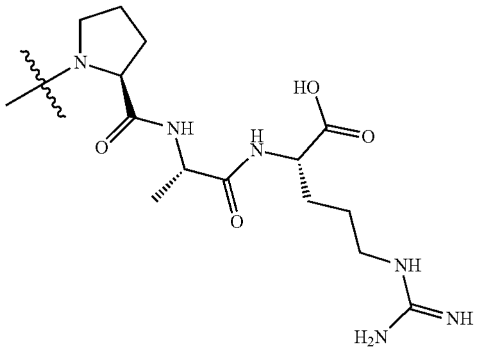 [SMILES: *N1CCC[C@H]1C(=O)N[C@@H](C)C(=O)N[C@@H](CCCNC(=N)N)C(=O)O] |
| ABT202 |
| 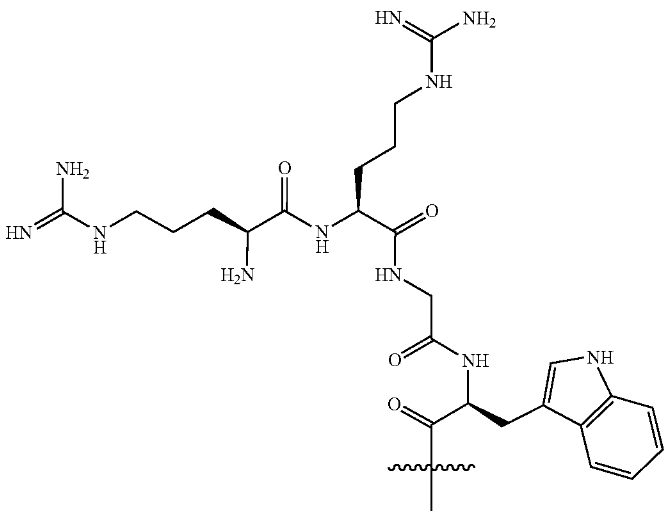 [SMILES: *C(=O)[C@H](Cc1c[nH]c2ccccc12)NC(=O)CNC(=O)[C@H](CCCNC(=N)N)NC(=O)[C@@H](N)CCCNC(=N)N] |
| ABT203 |

TABLE 2-continued
| Exemplary binding moieties |
| --- |
| 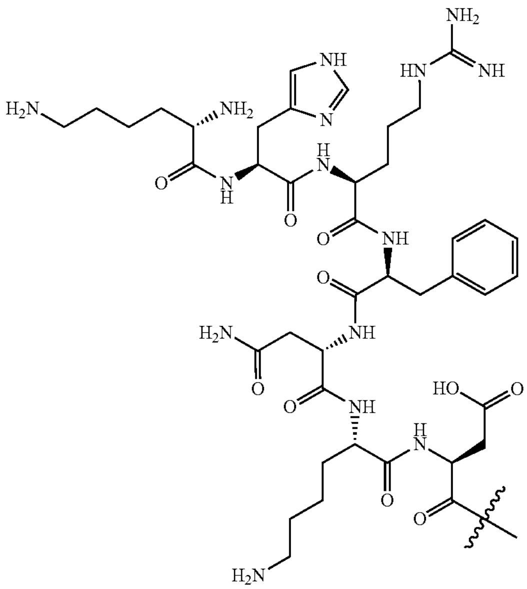 [SMILES: *C(=O)[C@H](CC(=O)O)NC(=O)[C@H](CCCCN)NC(=O)[C@H](CC(N)=O)NC(=O)[C@H](Cc1ccccc1)NC(=O)[C@H](CCCNC(=N)N)NC(=O)[C@H](Cc1c[nH]cn1)NC(=O)[C@@H](N)CCCCN] |
| ABT204 |
| 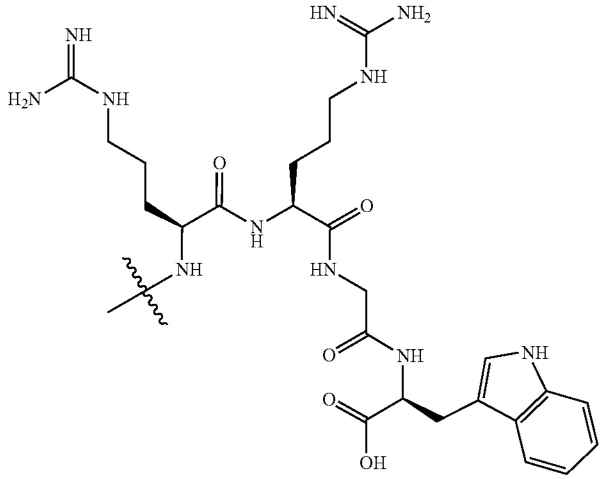 [SMILES: *N[C@@H](CCCNC(=N)N)C(=O)N[C@@H](CCCNC(=N)N)C(=O)NCC(=O)N[C@@H](Cc1c[nH]c2ccccc12)C(=O)O] |
| ABT205 |
| 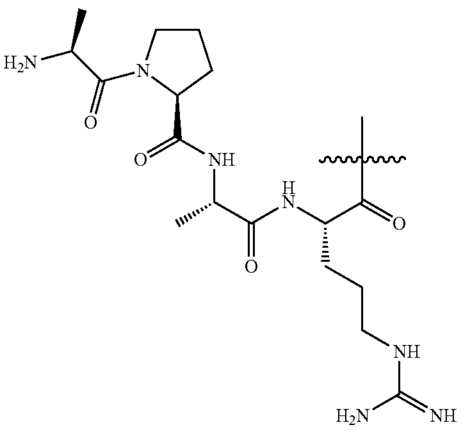 [SMILES: *C(=O)[C@H](CCCNC(=N)N)NC(=O)[C@H](C)NC(=O)[C@@H]1CCCN1C(=O)[C@H](C)N] |
| ABT206 |

TABLE 2-continued
| Exemplary binding moieties |
| --- |
| 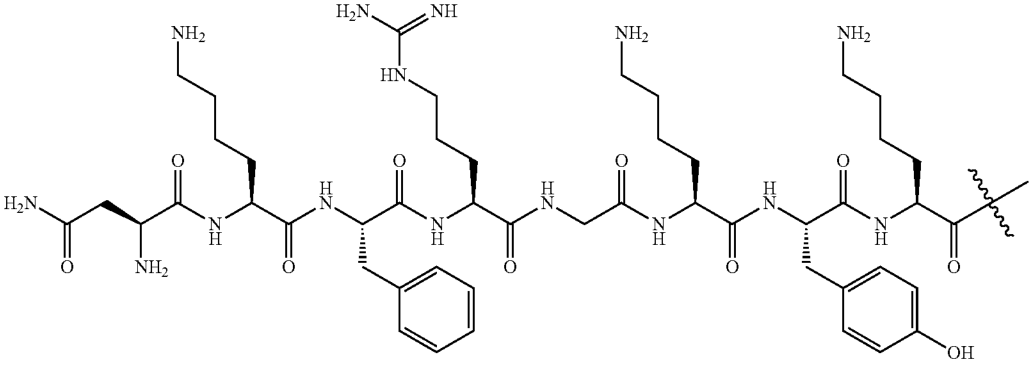 [SMILES: *C(=O)[C@H](CCCCN)NC(=O)[C@H](Cc1ccc(O)cc1)NC(=O)[C@H](CCCCN)NC(=O)CNC(=O)[C@H](CCCNC(=N)N)NC(=O)[C@H](Cc1ccccc1)NC(=O)[C@H](CCCCN)NC(=O)[C@@H](N)CC(N)=O] |
| ABT207 |
| 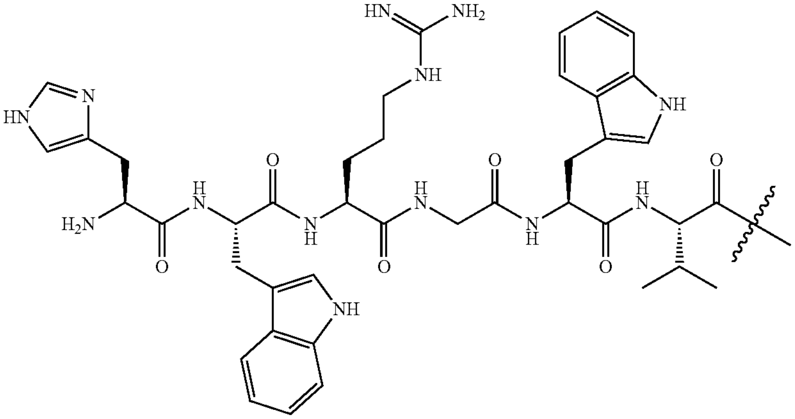 [SMILES: *C(=O)[C@@H](NC(=O)[C@H](Cc1c[nH]c2ccccc12)NC(=O)CNC(=O)[C@H](CCCNC(=N)N)NC(=O)[C@H](Cc1c[nH]c2ccccc12)NC(=O)[C@@H](N)Cc1c[nH]cn1)C(C)C] |
| ABT208 |
| 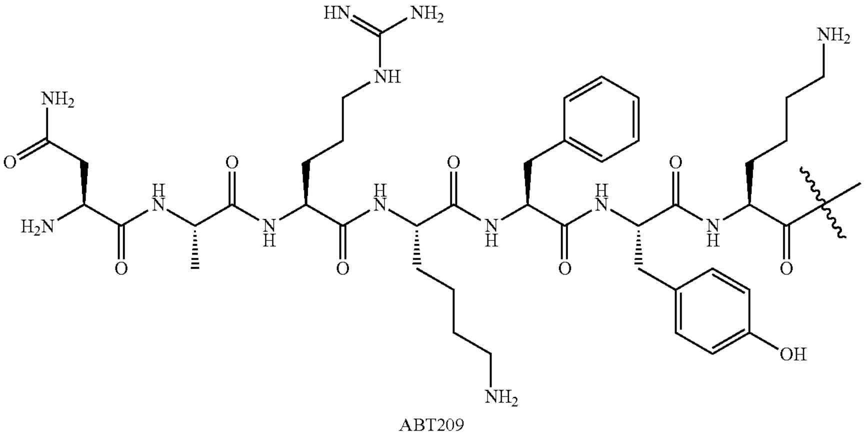 |
| ABT209 |

TABLE 2-continued
| Exemplary binding moieties |
| --- |
| 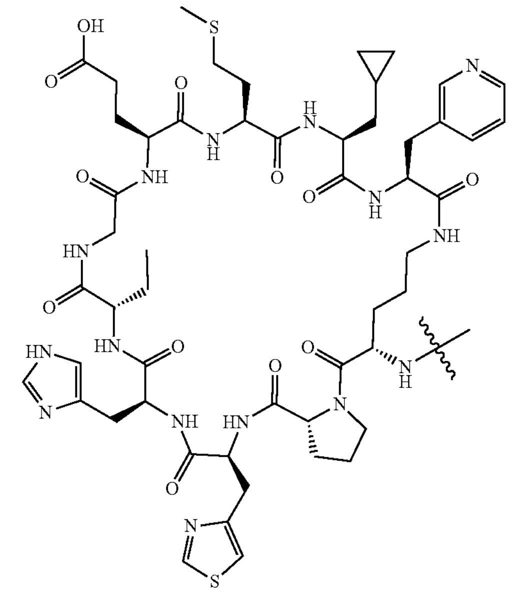 [SMILES: *N[C@H]1CCCNC(=O)[C@H](Cc2cccnc2)NC(=O)[C@H](CC2CC2)NC(=O)[C@H](CCSC)NC(=O)[C@H](CCC(=O)O)NC(=O)CNC(=O)[C@H](CC)NC(=O)[C@H](Cc2c[nH]cn2)NC(=O)[C@H](Cc2cscn2)NC(=O)[C@H]2CCCN2C1=O] |
| ABT210 |
| 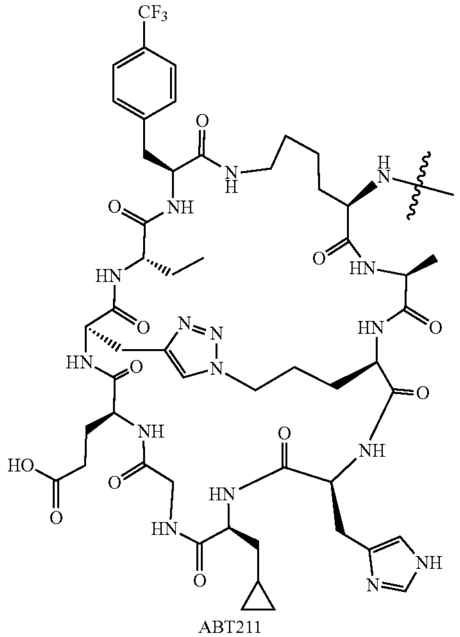 |
| ABT211 |

TABLE 2-continued
| Exemplary binding moieties |
|---|
| 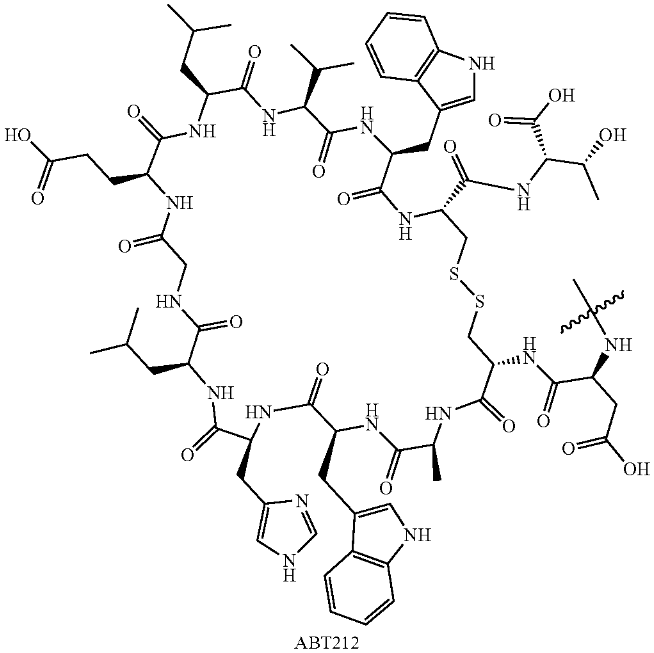 ABT212 |
| 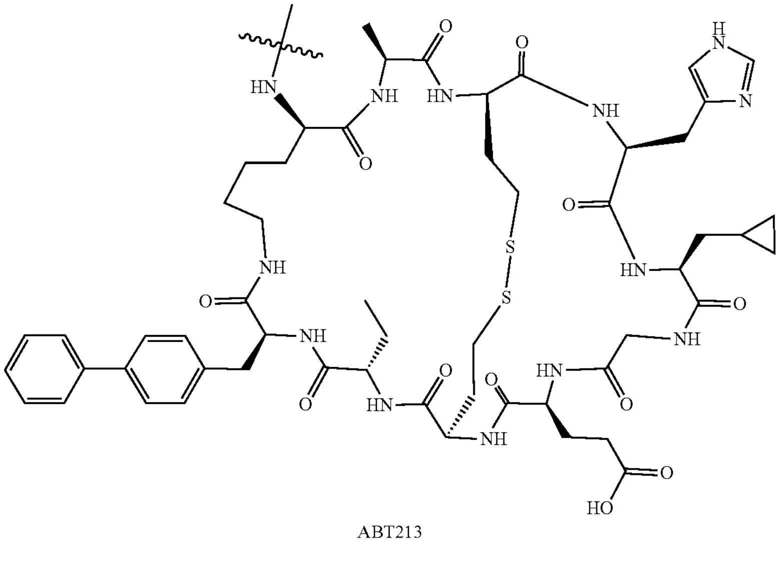 ABT213 |

TABLE 2-continued
| Exemplary binding moieties |
| --- |
| 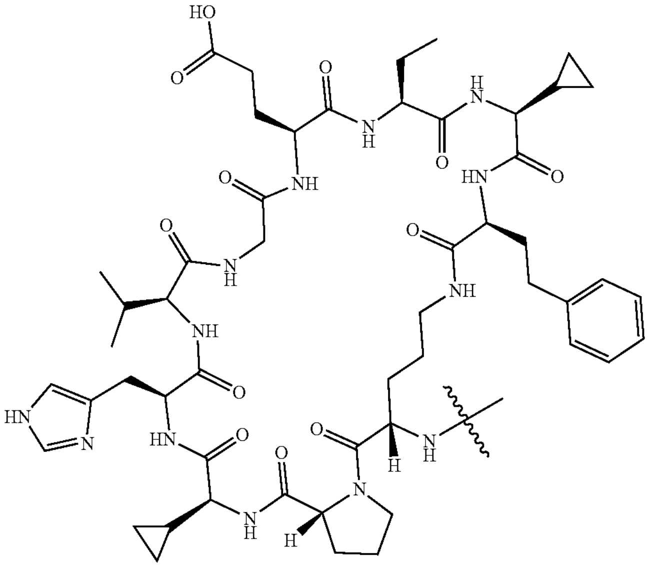 [SMILES: *N[C@H]1CCCNC(=O)[C@H](CCc2ccccc2)NC(=O)[C@H](C2CC2)NC(=O)[C@H](CC)NC(=O)[C@H](CCC(=O)O)NC(=O)CNC(=O)[C@H](C(C)C)NC(=O)[C@H](Cc2c[nH]cn2)NC(=O)[C@H](C2CC2)NC(=O)[C@H]2CCCN2C1=O]<br>ABT214 |
| 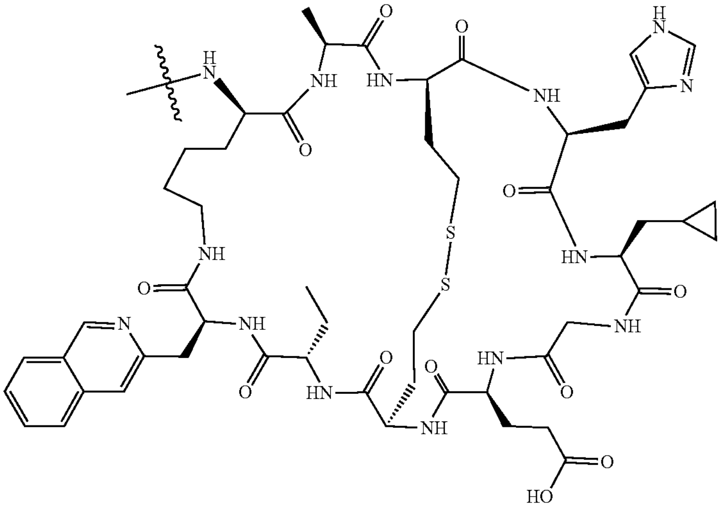 [SMILES: *N[C@@H]1CCCCNC(=O)[C@H](Cc2cc3ccccc3cn2)NC(=O)[C@H](CC)NC(=O)[C@H]2CCSSCC[C@@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2]<br>ABT215 |

TABLE 2-continued
| Exemplary binding moieties |
| --- |
| 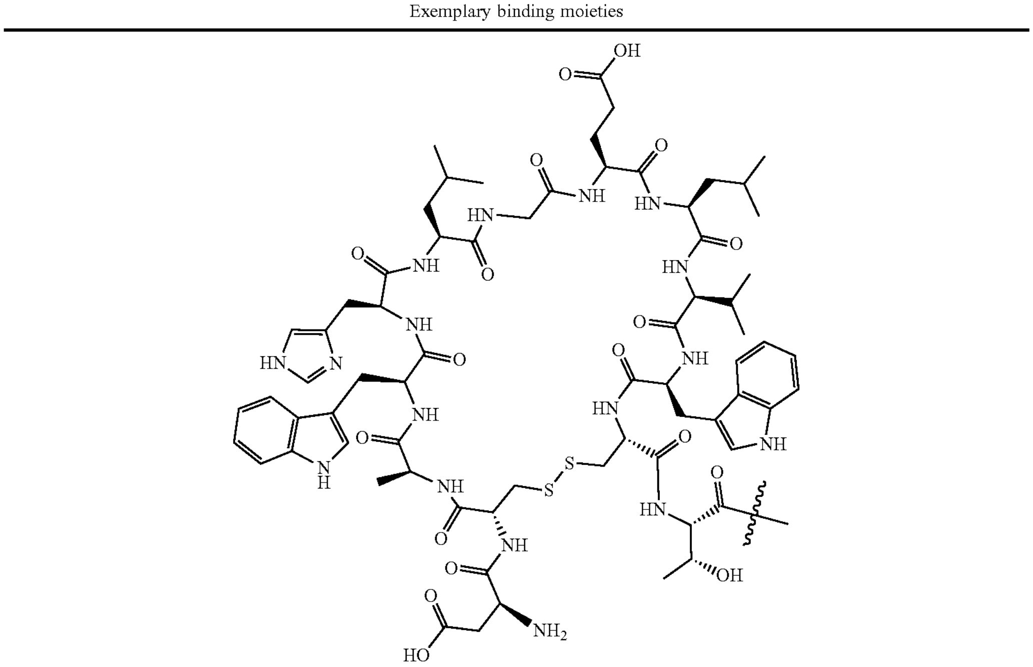 ABT216 |
| 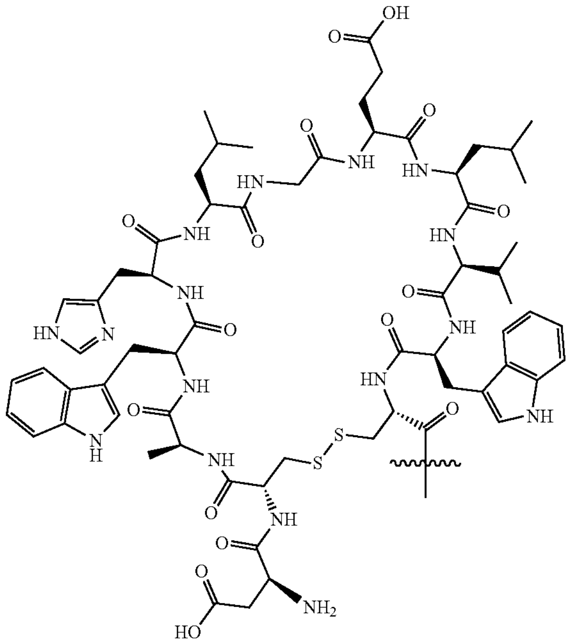 [SMILES: *C(=O)[C@@H]1CSSC[C@H](NC(=O)[C@@H](N)CC(=O)O)C(=O)N[C@@H](C)C(=O)N[C@@H](Cc2c[nH]c3ccccc23)C(=O)N[C@@H](Cc2c[nH]cn2)C(=O)N[C@@H](CC(C)C)C(=O)NCC(=O)N[C@@H](CCC(=O)O)C(=O)N[C@@H](CC(C)C)C(=O)N[C@@H](C(C)C)C(=O)N[C@@H](Cc2c[nH]c3ccccc23)C(=O)N1] ABT217 |

TABLE 2-continued
Exemplary binding moieties
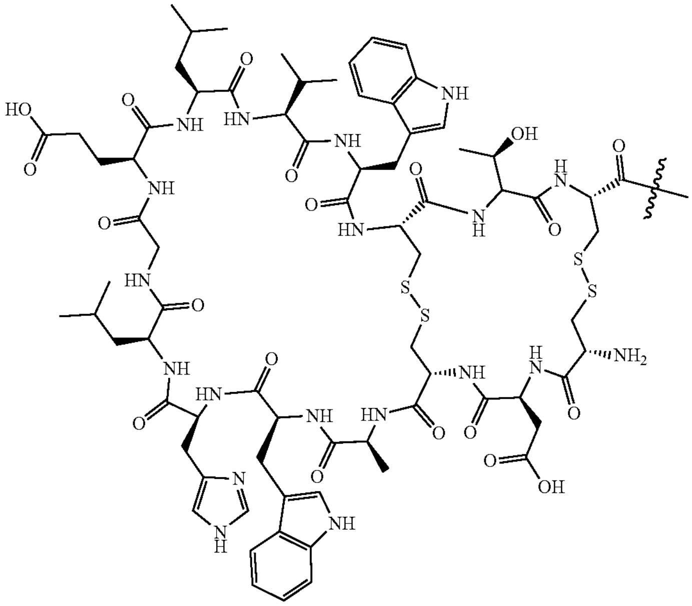 [SMILES: *C(=O)[C@@H]1CSSC[C@H](N)C(=O)N[C@@H](CC(=O)O)C(=O)N[C@H]2CSSC[C@H](NC(=O)[C@H](Cc3c[nH]c4ccccc34)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc3c[nH]cn3)NC(=O)[C@H](Cc3c[nH]c4ccccc34)NC(=O)[C@H](C)NC2=O)C(=O)NC([C@@H](C)O)C(=O)N1]
ABT218
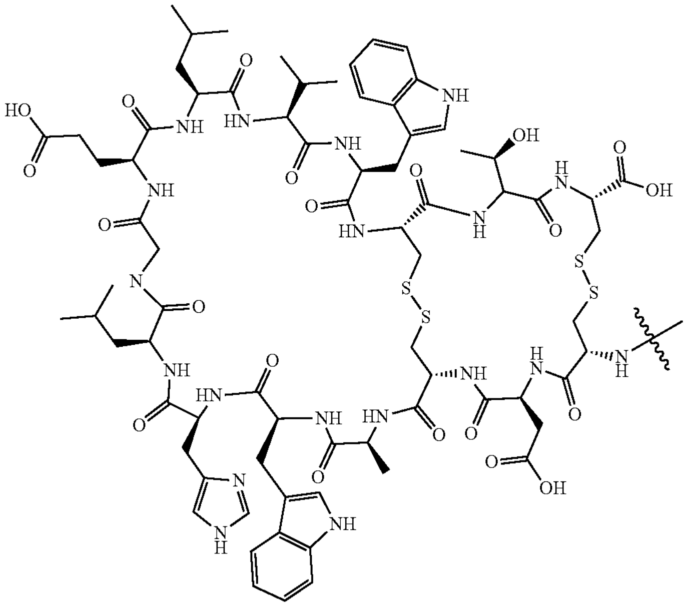
ABT219

TABLE 2-continued
| Exemplary binding moieties |
| --- |
| 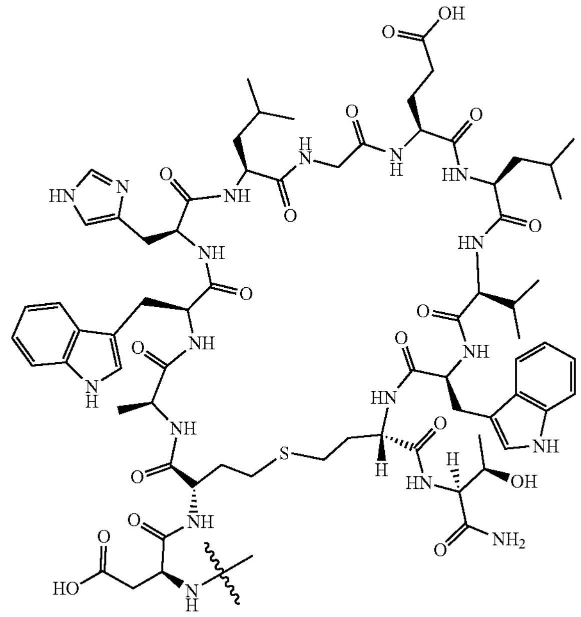 ABT220 |
| 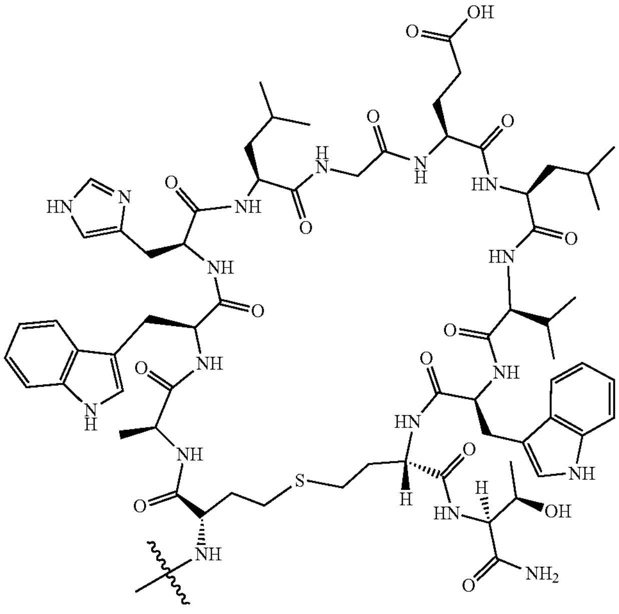 ABT221 |

TABLE 2-continued
| Exemplary binding moieties |
| --- |
| 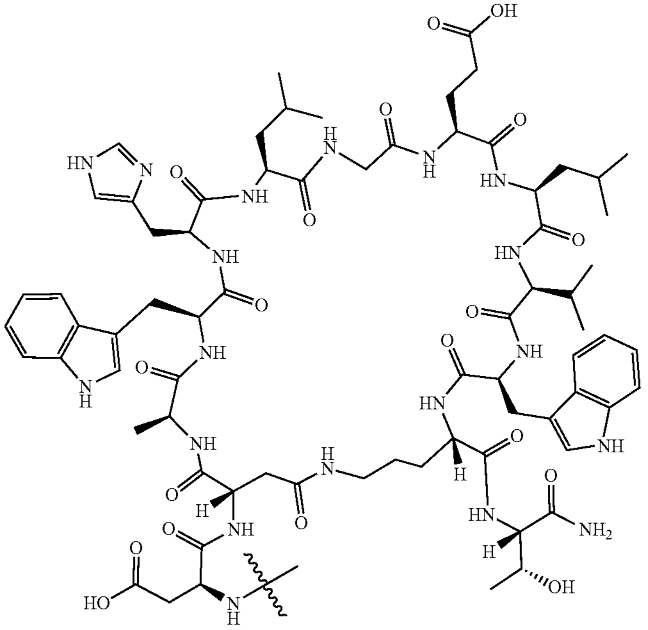 [SMILES: *N[C@@H](CC(=O)O)C(=O)N[C@H]1CC(=O)NCCC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O] ABT222 |
| 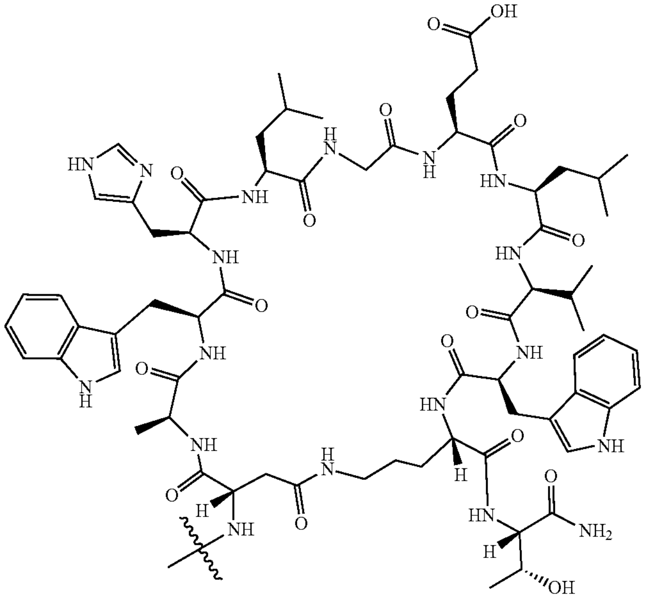 [SMILES: *N[C@H]1CC(=O)NCCC[C@@H](C(=O)N[C@H](C(N)=O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O] ABT223 |

TABLE 2-continued
| Exemplary binding moieties |
| --- |
| 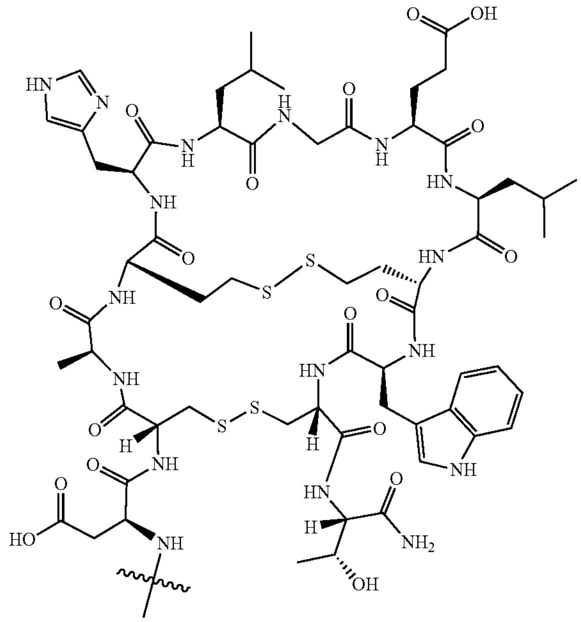 [SMILES: *N[C@@H](CC(=O)O)C(=O)N[C@H]1CSSC[C@@H](C(=O)N[C@H](C(N)=O)[C@@H](C)O)NC(=O)[C@H](Cc2c[nH]c3ccccc23)NC(=O)[C@@H]2CCSSCC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CC(C)C)C(=O)N2] |
| ABT224 |
| 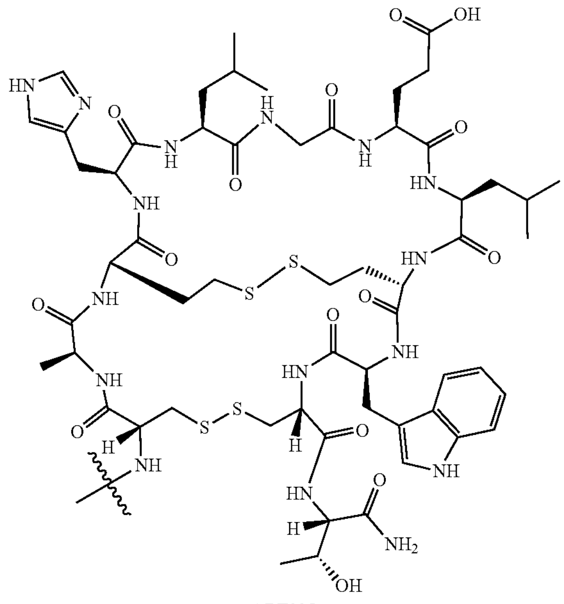 [SMILES: *N[C@H]1CSSC[C@@H](C(=O)N[C@H](C(N)=O)[C@@H](C)O)NC(=O)[C@H](Cc2c[nH]c3ccccc23)NC(=O)[C@@H]2CCSSCC[C@H](NC(=O)[C@H](C)NC1=O)C(=O)N[C@@H](Cc1c[nH]cn1)C(=O)N[C@@H](CC(C)C)C(=O)NCC(=O)N[C@@H](CCC(=O)O)C(=O)N[C@@H](CC(C)C)C(=O)N2] |
| ABT225 |

TABLE 2-continued
| Exemplary binding moieties |
| --- |
| 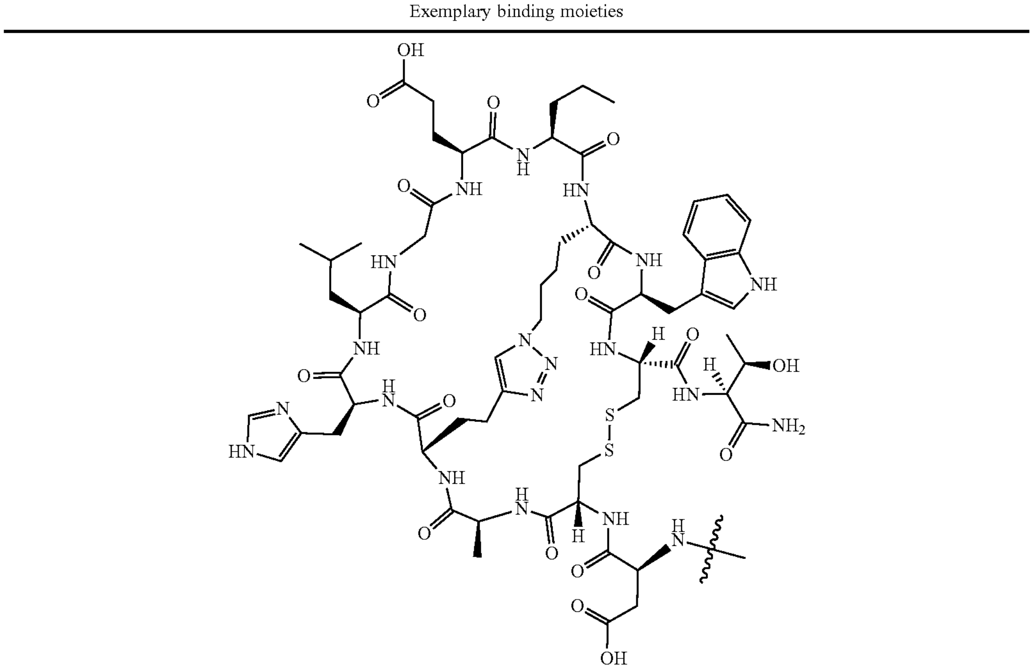 ABT226 |
| 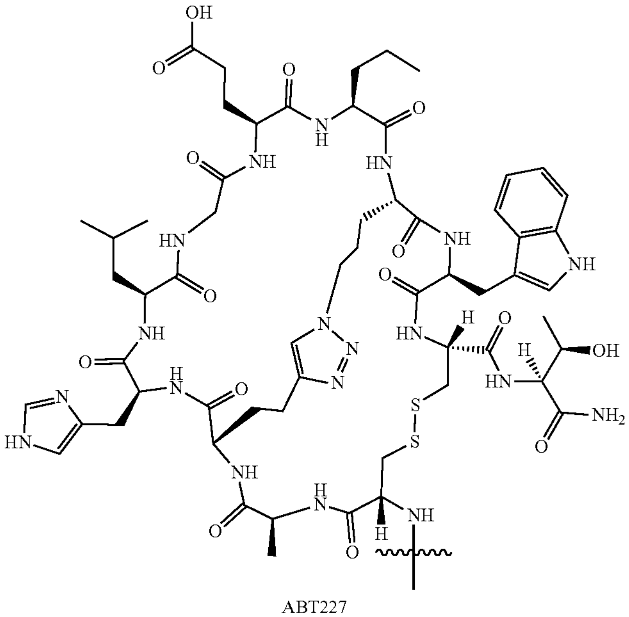 ABT227 |

TABLE 2-continued
| Exemplary binding moieties |
|---|
| 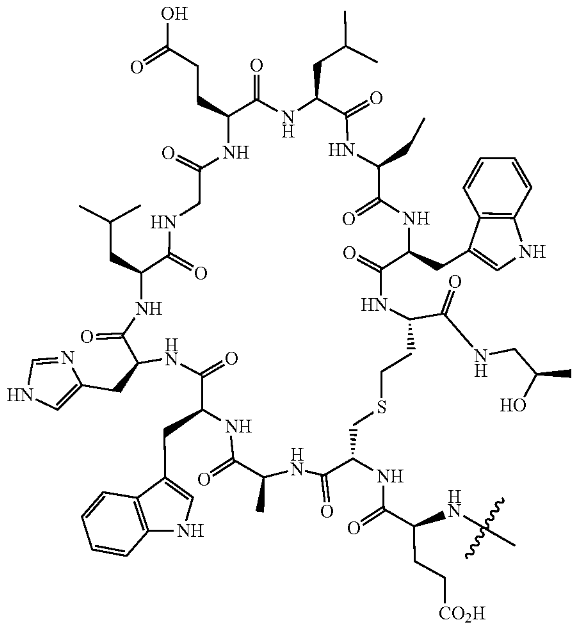 [SMILES: *N[C@@H](CCC(=O)O)C(=O)N[C@H]1CSCC[C@@H](C(=O)NC[C@@H](C)O)NC(=O)[C@H](Cc2c[nH]c3ccccc23)NC(=O)[C@H](CC)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O] ABT228 |
| 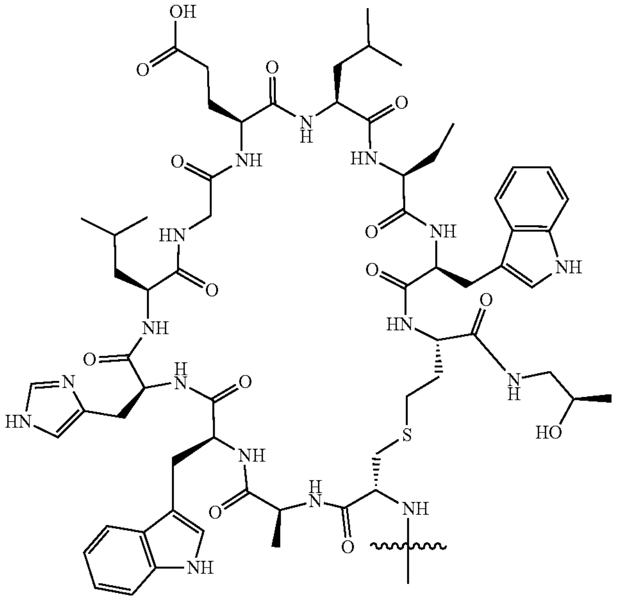 [SMILES: *N[C@H]1CSCC[C@@H](C(=O)NC[C@@H](C)O)NC(=O)[C@H](Cc2c[nH]c3ccccc23)NC(=O)[C@H](CC)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O] ABT229 |

TABLE 2-continued
| Exemplary binding moieties |
| --- |
| 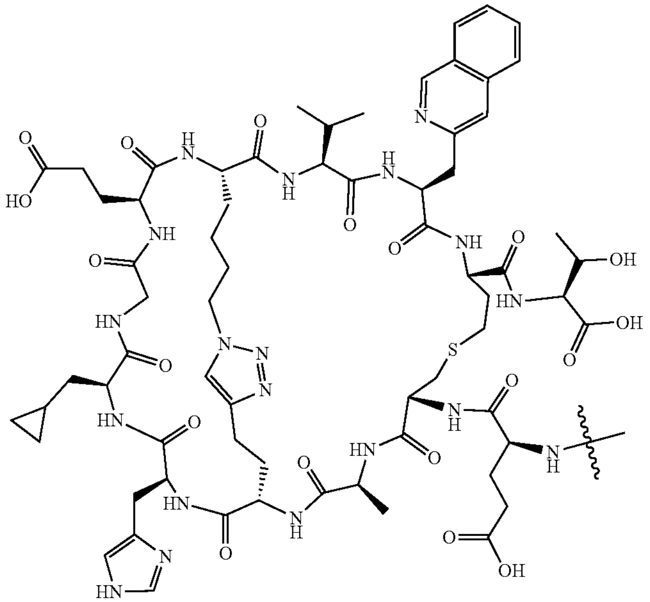 [SMILES: *N[C@@H](CCC(=O)O)C(=O)N[C@H]1CSCC[C@@H](C(=O)N[C@H](C(=O)O)C(C)O)NC(=O)[C@H](Cc2cc3ccccc3cn2)NC(=O)[C@H](C(C)C)NC(=O)[C@@H]2CCCCn3cc(nn3)CC[C@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2] |
| ABT230 |
| 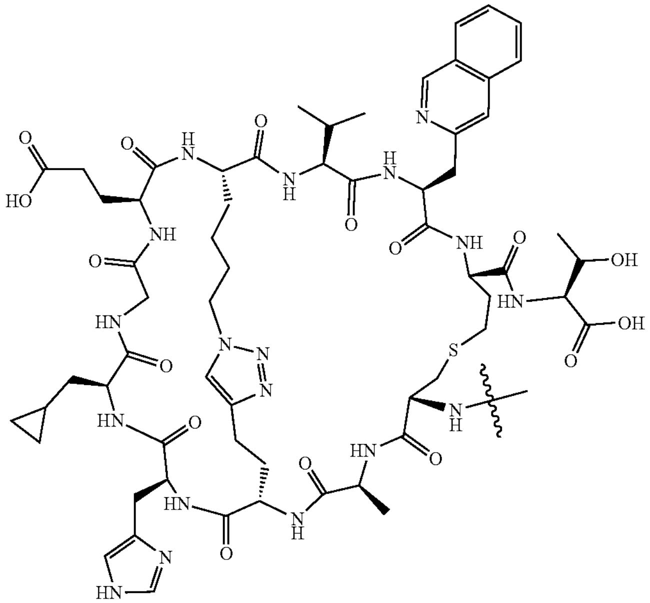 [SMILES: *N[C@H]1CSCC[C@@H](C(=O)N[C@H](C(=O)O)C(C)O)NC(=O)[C@H](Cc2cc3ccccc3cn2)NC(=O)[C@H](C(C)C)NC(=O)[C@@H]2CCCCn3cc(nn3)CC[C@H](NC(=O)[C@H](C)NC1=O)C(=O)N[C@@H](Cc1c[nH]cn1)C(=O)N[C@@H](CC1CC1)C(=O)NCC(=O)N[C@@H](CCC(=O)O)C(=O)N2] |
| ABT231 |

TABLE 2-continued
| Exemplary binding moieties |
|---|
| 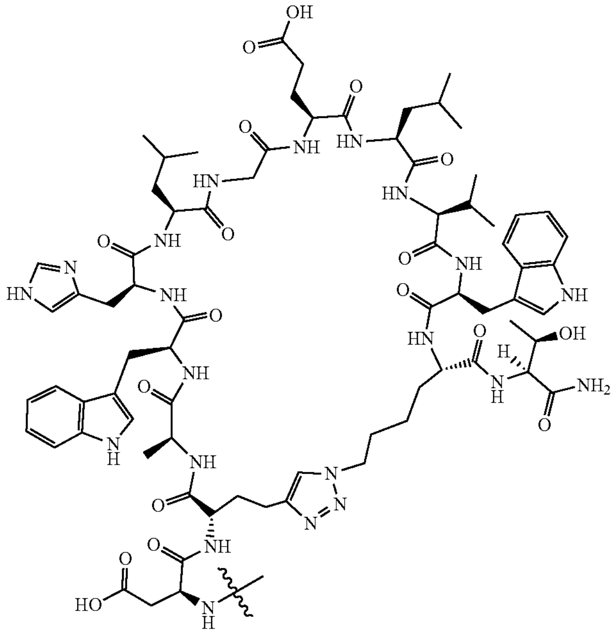 |
| ABT232 |
| 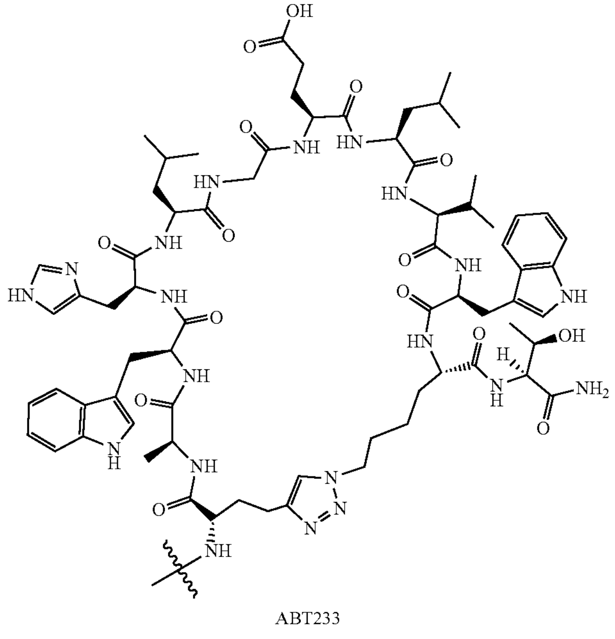 |
| ABT233 |

TABLE 2-continued
| Exemplary binding moieties |
| --- |
| 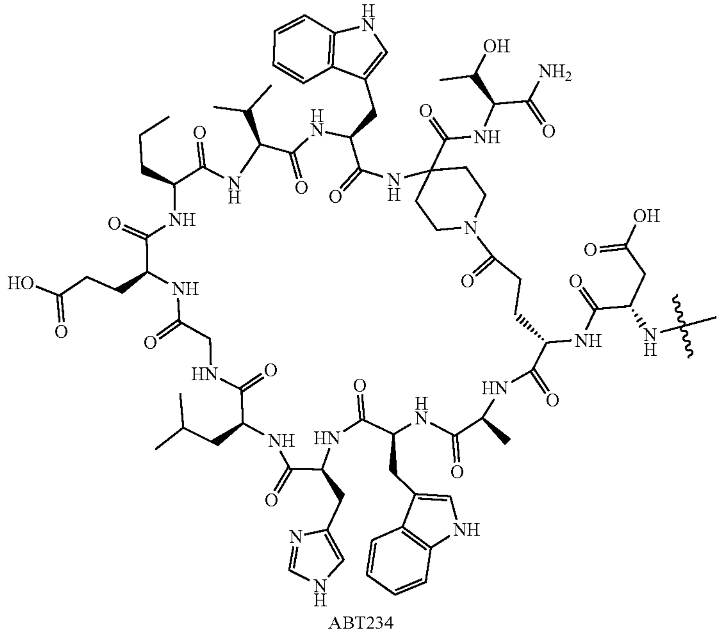 ABT234 |
| 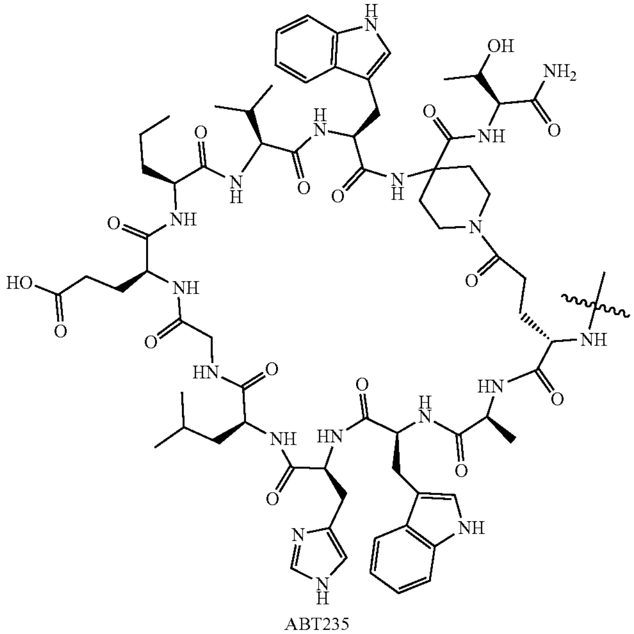 ABT235 |

TABLE 2-continued
| Exemplary binding moieties |
| --- |
| 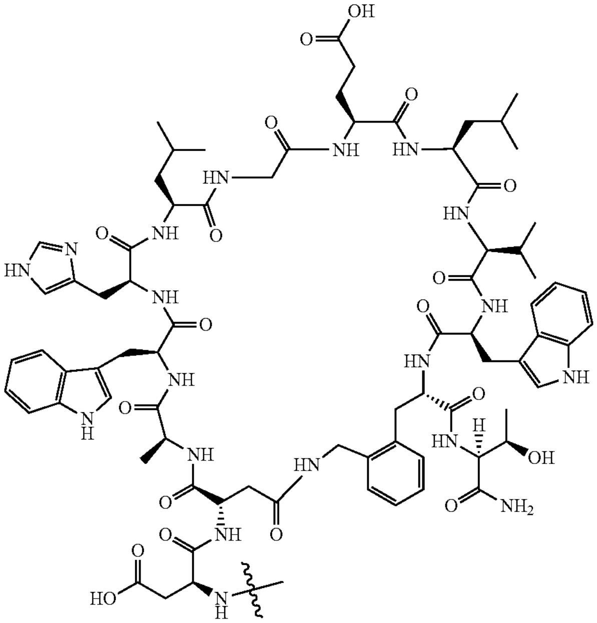 ABT236 |
| 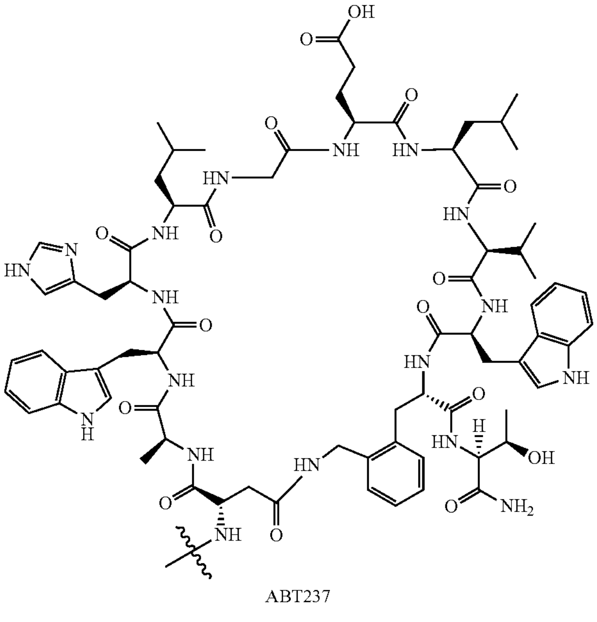 ABT237 |

TABLE 2-continued
| Exemplary binding moieties |
|---|
| 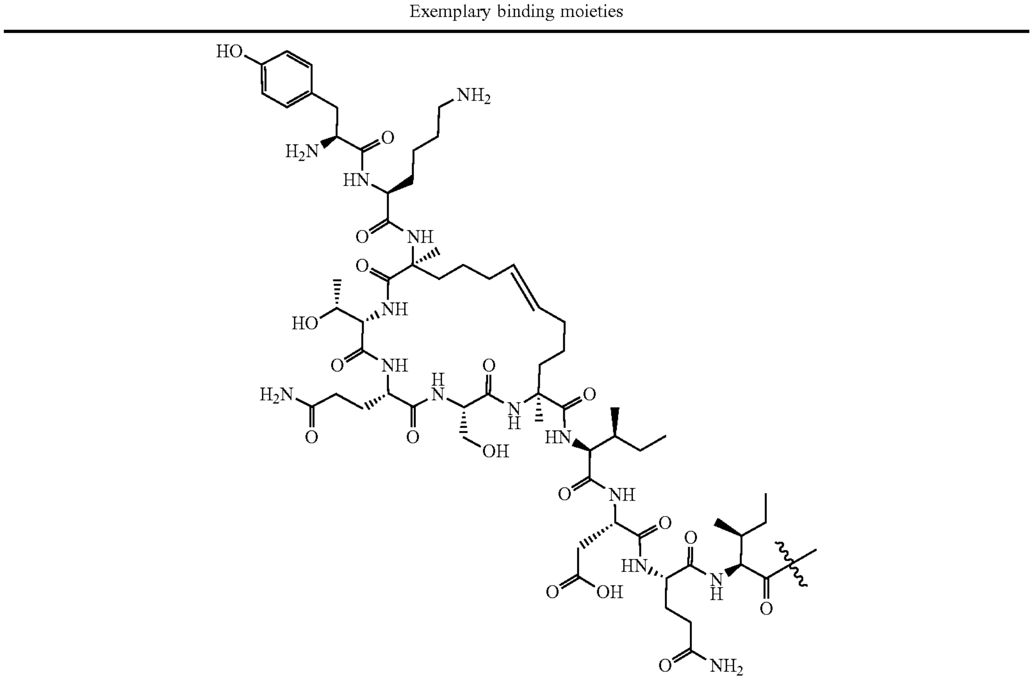 |
| ABT238 |
| 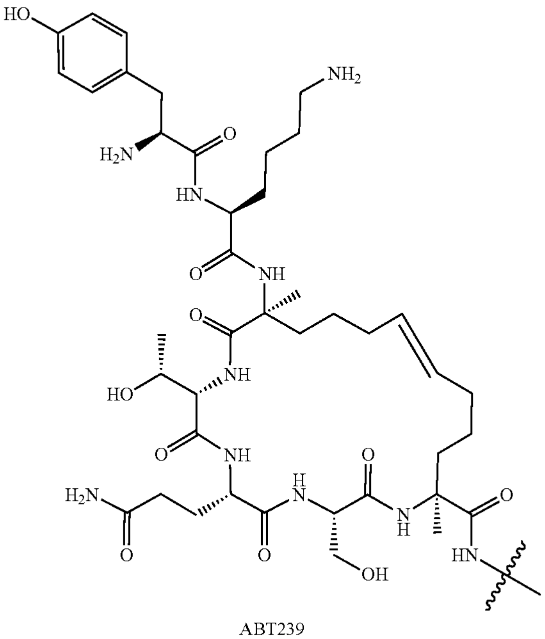 |
| ABT239 |

TABLE 2-continued
| Exemplary binding moieties |
| --- |
| 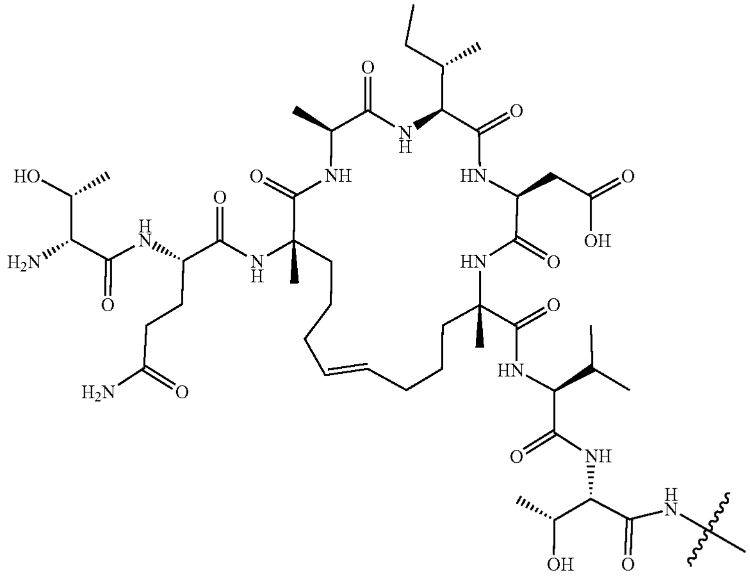 [SMILES: *NC(=O)[C@@H](NC(=O)[C@@H](NC(=O)[C@]1(C)CCC/C=C/CCC[C@](C)(NC(=O)[C@H](CCC(N)=O)NC(=O)[C@H](N)[C@@H](C)O)C(=O)N[C@@H](C)C(=O)N[C@@H]([C@@H](C)CC)C(=O)N[C@@H](CC(=O)O)C(=O)N1)C(C)C)[C@@H](C)O] |
| ABT240 |
| 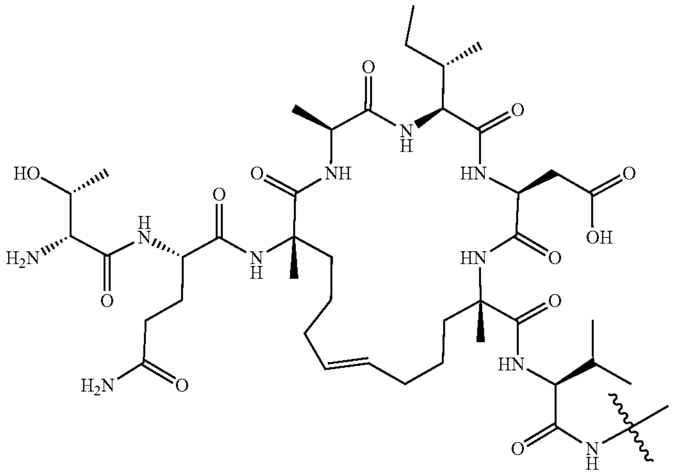 [SMILES: *NC(=O)[C@@H](NC(=O)[C@]1(C)CCC/C=C/CCC[C@](C)(NC(=O)[C@H](CCC(N)=O)NC(=O)[C@H](N)[C@@H](C)O)C(=O)N[C@@H](C)C(=O)N[C@@H]([C@@H](C)CC)C(=O)N[C@@H](CC(=O)O)C(=O)N1)C(C)C] |
| ABT241 |
| 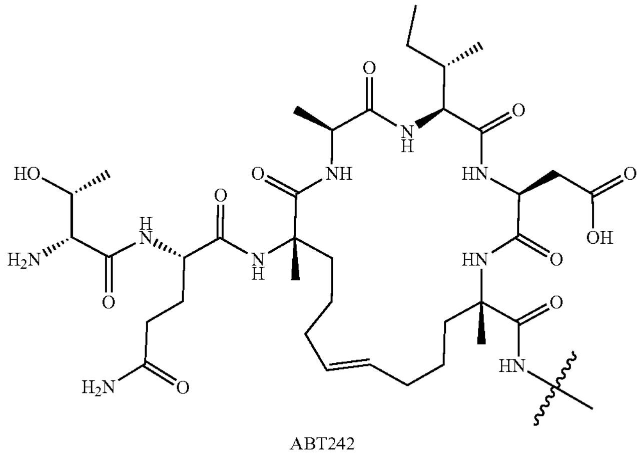 |
| ABT242 |

TABLE 2-continued
| Exemplary binding moieties |
| --- |
| 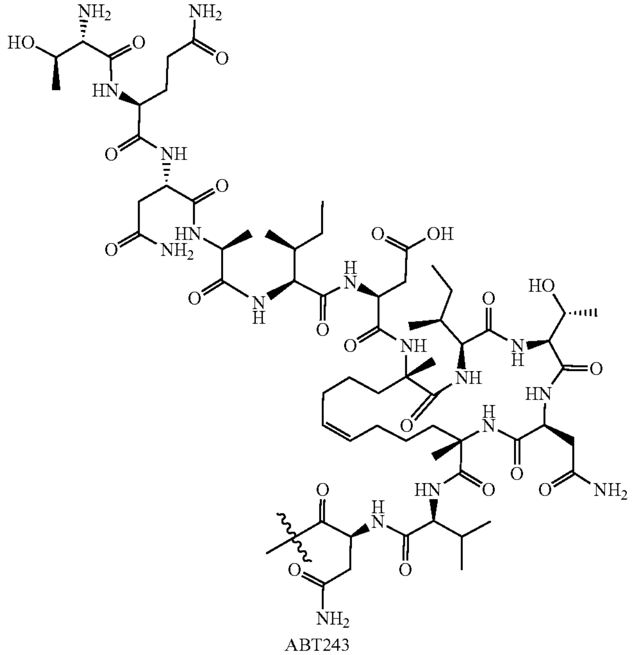 ABT243 |
| 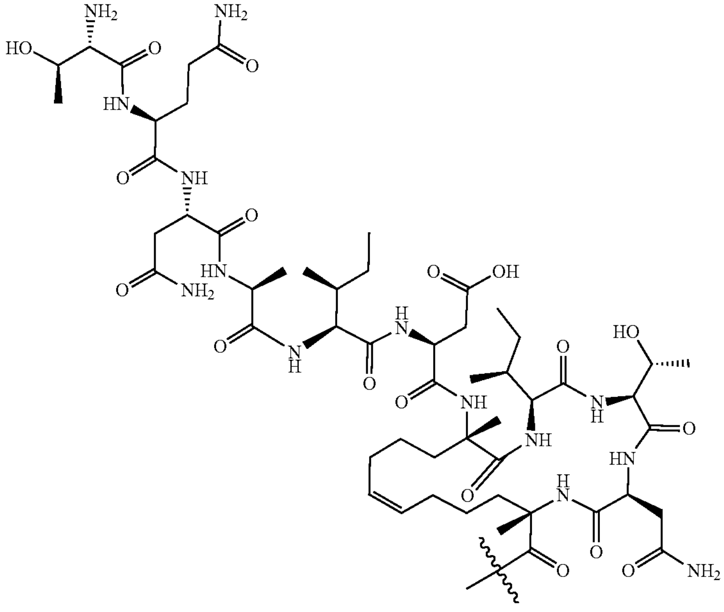 [SMILES: *C(=O)[C@]1(C)CCC/C=C\CCC[C@](C)(NC(=O)[C@H](CC(=O)O)NC(=O)[C@@H](NC(=O)[C@H](C)NC(=O)[C@H](CC(N)=O)NC(=O)[C@H](CCC(N)=O)NC(=O)[C@@H](N)[C@@H](C)O)[C@@H](C)CC)C(=O)N[C@@H]([C@@H](C)CC)C(=O)N[C@@H]([C@@H](C)O)C(=O)N[C@@H](CC(N)=O)C(=O)N1] ABT244 |

TABLE 2-continued
| Exemplary binding moieties |
| --- |
| 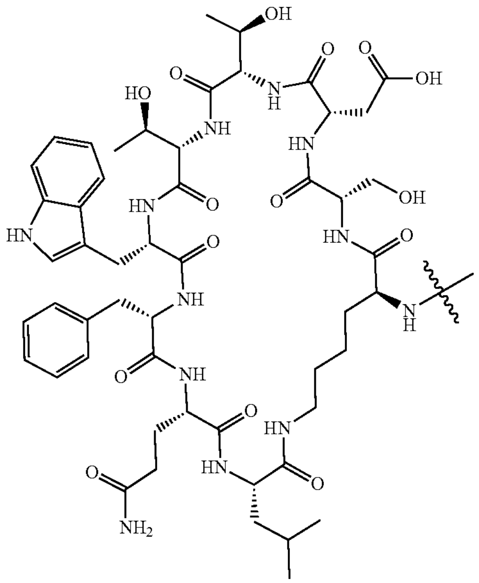 [SMILES: *N[C@H]1CCCCNC(=O)[C@H](CC(C)C)NC(=O)[C@H](CCC(N)=O)NC(=O)[C@H](Cc2ccccc2)NC(=O)[C@H](Cc2c[nH]c3ccccc23)NC(=O)[C@H]([C@@H](C)O)NC(=O)[C@H]([C@@H](C)O)NC(=O)[C@H](CC(=O)O)NC(=O)[C@H](CO)NC1=O] |
| ABT245 |
| 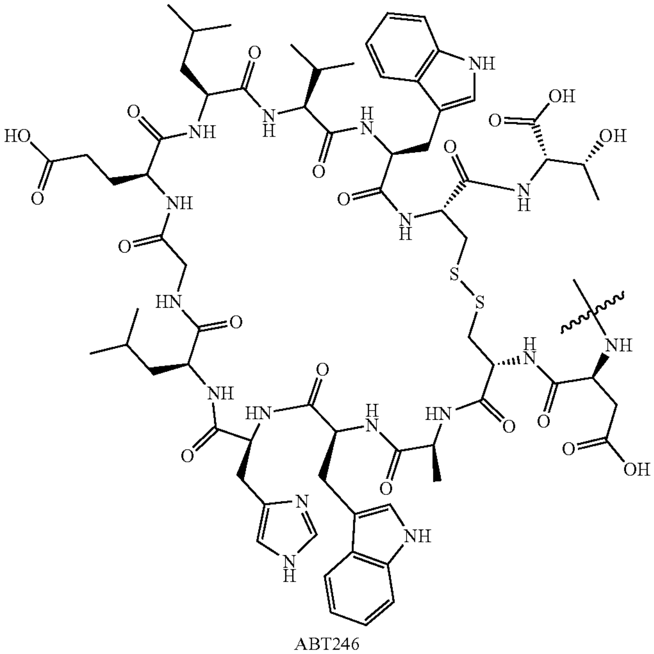 |
| ABT246 |

TABLE 2-continued
| Exemplary binding moieties |
|---|
| 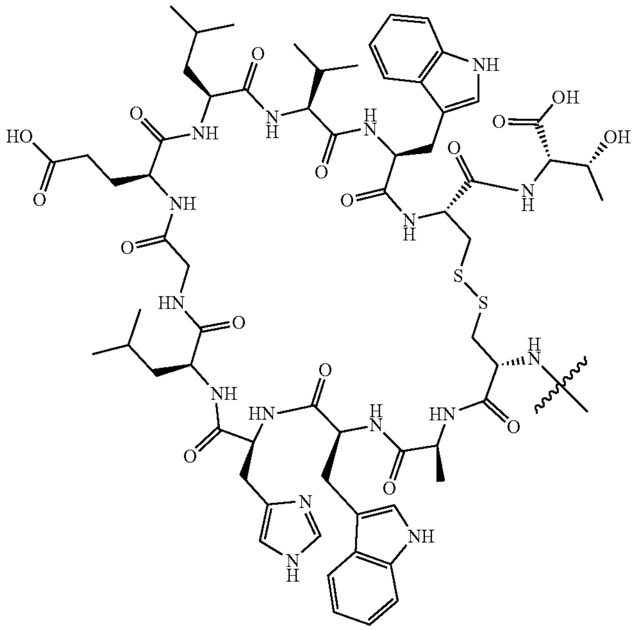 [SMILES: *N[C@H]1CSSC[C@@H](C(=O)N[C@H](C(=O)O)[C@@H](C)O)NC(=O)[C@H](Cc2c[nH]c3ccccc23)NC(=O)[C@H](C(C)C)NC(=O)[C@H](CC(C)C)NC(=O)[C@H](CCC(=O)O)NC(=O)CNC(=O)[C@H](CC(C)C)NC(=O)[C@H](Cc2c[nH]cn2)NC(=O)[C@H](Cc2c[nH]c3ccccc23)NC(=O)[C@H](C)NC1=O] |
| ABT247 |
| 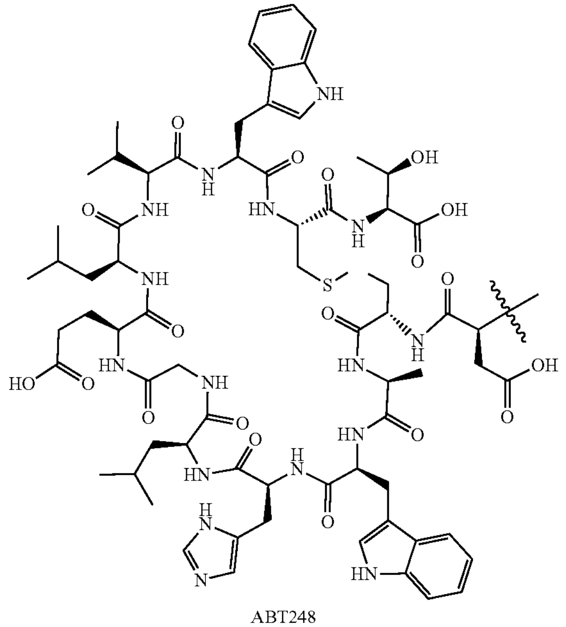 |
| ABT248 |

TABLE 2-continued

Exemplary binding moieties

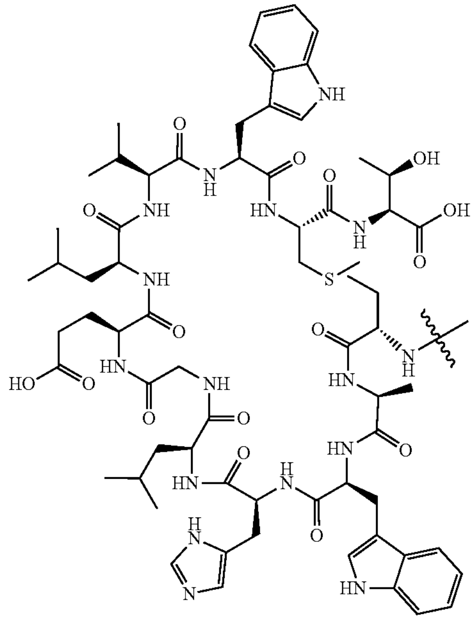 [SMILES: *N[C@@H](CC)C(=O)N[C@@H](C)C(=O)N[C@@H](Cc1c[nH]c2ccccc12)C(=O)N[C@@H](Cc1cnc[nH]1)C(=O)N[C@@H](CC(C)C)C(=O)NCC(=O)N[C@@H](CCC(=O)O)C(=O)N[C@@H](CC(C)C)C(=O)N[C@H](C(=O)N[C@@H](Cc1c[nH]c2ccccc12)C(=O)N[C@@H](CSC)C(=O)N[C@H](C(=O)O)[C@@H](C)O)C(C)C]

ABT249

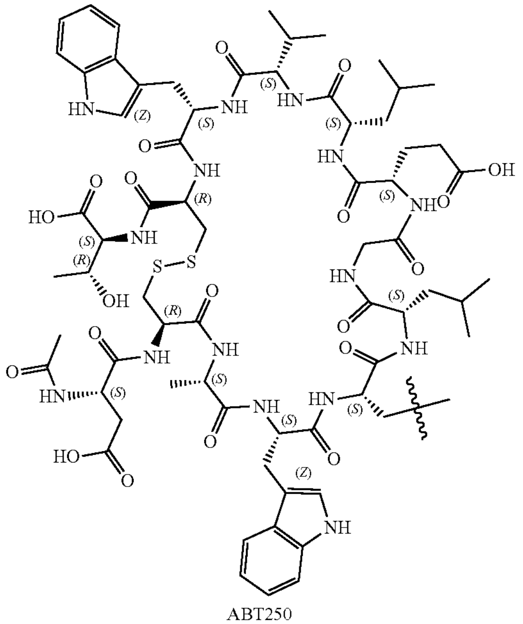

ABT250

In some embodiments, antibody-binding moieties, e.g., antibody-binding moieties, and useful technologies for developing or assessing such moieties are described in, e.g., Alves, *Langmuir,* 28, 9640-9648 (2012), Choe et al., *Materials,* 9, 994 (2016), Gupta et al., *Nature Biomedical Engineering,* 3, 917-929 (2019), Muguruma et al., *ACS Omega,* 4, 14390-14397 (2019), Yamada et al., *Angew Chem. Int., Ed Engl.;* 58(17), 5592-5597 (Apr. 16, 2019), Kruljec et al., *Bioconjug Chem.,* 28(8): 2009-2030 (2017), e.g., Fabsorbent, triazines, etc.; Kruljec et al., *Bioconjugate Chem.,* 29(8), 2763-2775 (2018), WO2012017021A2, etc., the binding moieties, e.g., antibody-binding moieties) of each of which is incorporated herein in its entirety by reference.

In some embodiments, an antibody-binding moiety, e.g., a protein-binding moiety, e.g., an antibody-binding moiety), is an affinity substance described in AU 2018259856 or WO 2018199337, the affinity substance of each of which is incorporated herein by reference.

In some embodiments, an antibody-binding moiety, e.g., an antibody-binding moiety, is or comprises an adapter protein agent, e.g., as described in Hui et al., Bioconjugate Chem., 26, 1456-1460 (2015). In some embodiments, when used under the present disclosure, adapter proteins do not require reactive residues) to achieve one or more advantages.

In some embodiments, an antibody-binding moiety, e.g., an antibody-binding moiety, is or comprises a triazine moiety, e.g., one described in US 2009/0286693. In some embodiments, an antibody-binding moiety, e.g., an antibody-binding moiety, is of such a structure that its corresponding compound is described in U.S. Pat. Publ. 2009/0286693, the compounds of which are independently incorporated by reference. In some embodiments, an antibody-binding moiety, e.g., an antibody-binding moiety, is ABT. In some embodiments, ABT is of such a structure that H-ABT is a compound described in US 2009/0286693, the compounds of which are independently incorporated by reference. In some embodiments, this compound can bind to an antibody. In some embodiments, this compound can bind to the Fc region of an antibody.

In some embodiments, an antibody-binding moiety, e.g., an antibody-binding moiety, is or comprises a triazine moiety, e.g., one described in Teng et al., J. Mol. Recognit., 12, 67-75 (1999). In some embodiments, an antibody-binding moiety, e.g., an antibody-binding moiety, is of such a structure that its corresponding compound is described in Teng et al., J. Mol. Recognit., 12, 67-75 (1999), the compounds of which are independently incorporated by reference. In some embodiments, an antibody-binding moiety, e.g., an antibody-binding moiety, is of such a structure that H-ABT is a compound described in Teng, the compounds of which are independently incorporated by reference. In some embodiments, this compound can bind to an antibody. In some embodiments, this compound can bind to the Fc region of an antibody.

In some embodiments, an antibody-binding moiety, e.g., an antibody-binding moiety, is a triazine moiety, e.g., one described in Uttamchandani et al., J. Comb. Chem., 6(6), 862-8 (November-December 2004). In some embodiments, an antibody-binding moiety, e.g., an antibody-binding moiety, is of such a structure that its corresponding compound is a compound described in Uttamchandani, the compounds of which are independently incorporated by reference. In some embodiments, an antibody-binding moiety, e.g., an antibody-binding moiety, is of such a structure that H-ABT is a compound described in Uttamchandani, the compounds of which are independently incorporated by reference. In some embodiments, this compound can bind to an antibody. In some embodiments, this compound can bind to the Fc region of an antibody.

In some embodiments, an antibody-binding moiety binds to one or more binding sites of a protein selected from the Markush group of proteins consisting of protein A, protein G, protein L, protein Z, protein LG, protein LA, and protein AG. In some embodiments, an antibody-binding moiety is described in Choe, Durgannavar, & Chung, Materials, 9(12) (2016).

In some embodiments, an antibody-binding moiety, e.g., an antibody-binding moiety, can bind to a nucleotide-binding site. In some embodiments, an antibody-binding moiety, e.g., an antibody-binding moiety, is a small molecule that can bind to a nucleotide-binding site. In some embodiments, a small molecule is tryptamine. In some embodiments, an antibody-binding moiety, e.g., an antibody-binding moiety, is of such a structure that H-ABT is tryptamine. Certain useful technologies were described in Mustafaoglu et al., *Analyst,* 141(24), 6571-6582 (Nov. 28, 2016).

Characterizing Antibody-Binding Properties.

Many technologies are available for identifying, assessing, or characterizing antibody-binding moieties, including protein-binding moieties, e.g., antibody-binding moieties such as universal antibody-binding moieties, or their use in provided technologies, e.g., those described in WO/2019/023501, the technologies of which are incorporated herein by reference. In some embodiments, an antibody-binding moiety is a moiety, e.g., small molecule moiety, peptide moiety, nucleic acid moiety, etc., that can selectively bind to IgG and, when used in provided technologies, can provide or stimulate ADCC or ADCP. In some embodiments, peptide display technologies, e.g., phase display, non-cellular display, etc., can identify antibody-binding moieties. In some embodiments, an antibody-binding moiety is a moiety, e.g., small molecule moiety, peptide moiety, nucleic acid moiety, etc., that can bind to IgG and optionally can compete with known antibody binders, e.g., protein A, protein G, protein L, etc.

The characterization of antibodies specific for Gal-deficient IgA1 secreted by cloned cell lines can be performed using the method of Suzuki et al., J. Clin. Invest., 119, 1668-1677 (2009). Capture ELISA measures the levels of antigen-specific IgG produced by IgG-secreting cell lines. The results are expressed as optical density (OD) measured at 490 nm. Levels of IgG directed against dd-IgA1 and Fab-IgA1 are higher in IgAN patients than in controls. IgG secreted by cell lines from IgAN patients and healthy controls is tested for binding with a hinge-region glycopeptide (HR-GalNAc-BSA) or HR-BSA, with or without HAA blockade. IgG produced by cell lines from IgAN patients bound to HR-GalNAc in an HAA-inhabitable fashion.

The ability of glycan-specific antibodies to form immune complexes with Gal-deficient IgA1 can be determined in vitro by the method of Suzuki et al., J. Clin. Invest., 119, 1668-1677 (2009), by incubating the purified IgG proteins with a Gal-deficient IgA1 myeloma protein (Ale mono) at a 1:1 molar ratio. The reaction mixture was then fractionated by HPLC with the IgA1-IgG immune complexes identified by cross-capture ELISA. Incubation of the Gal-deficient IgA1 with IgG produced by the cells derived from IgAN patients produced greater amounts of immune complexes than were formed on incubation with IgG produced by cells derived from healthy controls. Analysis of the size and composition of the immune complexes suggested that they consisted of one molecule of IgG bound to either one or two molecules of IgA1.

Characterization of immune-complex formation can be determined in vitro using the method of Suzuki et al., J. Clin. Invest., 119, 1668-1677 (2009). Size-exclusion chromatography and ELISA analysis measure the immune complexes formed in vitro with monomeric Gal-deficient IgA1 (50 μg) and glycan-specific IgG (50 μg) from patients with IgAN or healthy controls. IgG and monomeric (m) and dimeric (d) IgA1 standards were used to calibrate the column. Glycan-specific IgG from IgAN patients exhibits more binding to Gal-deficient IgA1 than binding IgG from healthy controls. Immune complexes likely have one or two molecules of IgA1 bound to two molecules of IgG. Dot-blot analysis shows that IgG secreted by cell lines from IgAN patients shows high binding to Gal-deficient IgA1.

Measurement of Ig and immune-complex levels can be determined in vitro using the method of Suzuki et al., J. Clin. Invest., 119, 1668-1677 (2009). The isotypes of the immunoglobulins secreted by the immortalized cells are determined by capture ELISA. ELISA plates were coated with 1 μg/ml of the F(ab')2 fragment of goat IgG specific for human IgA, IgG, or IgM (Jackson ImmunoResearch Laboratories Inc.). The captured immunoglobulins are detected with a biotin-labeled F(ab')2 fragment of goat IgG anti-human IgA, IgG, or IgM antibody (BioSource). Avidin-horseradish peroxidase conjugate (ExtrAvidin; Sigma-Aldrich) and the peroxidase chromogenic substrate o-phenylenediamine —$H_2O_2$ (Sigma-Aldrich) are added. The color reaction is stopped with 1 M sulfuric acid, and the absorbance at 490 nm was measured using an EL312 BioKinetics Microplate Reader (BioTek). Standard curves for immunoglobulins are generated from a pool of normal human sera calibrated for all Ig isotypes (Binding Site). The results are calculated using a DeltaSoft III computer program (BioMetallics). Urinary IgA-IgG immune complexes are measured using cross-capture ELISA.

ELISA characterization of antigen-specific IgG antibodies. The binding of serum IgG from IgAN patients and healthy controls, as well as IgG secreted by EBV-immortalized cells from the same subjects, are analyzed by ELISA, according to the method of Suzuki et al., J. Clin. Invest., 119, 1668-1677 (2009) using a panel of antigens: dd-IgA1, Fab-IgA1 generated using an IgA-specific protease from *Haemophilus influenzae* HK50, HR-BSA, and HR-GalNAc-BSA. HR-GalNAc was synthesized by Bachem (asterisks mark the sites with GalNAc): V—P—S-T-P—P-*T-P—*S—P—*S-T-P—P-T-P—S—P—S—C—NH2 [SEQ ID NO: 15]. The hinge-region peptide was the same peptide but with no GalNAc. Both preparations were cross-linked to bovine serum albumin. For ELISA, flat-bottom 96-well plates (MaxiSorp; Nunc) were coated with 1 μg/ml solution of the antigens mentioned above. Serum or culture supernatant samples diluted in phosphate-buffered saline were added to each well. The total IgG used for the analyses was normalized in all samples. The captured IgG were detected with a biotin-labeled F(ab')2 fragment of goat IgG anti-human IgG antibody (BioSource; Invitrogen). Avidin-horseradish peroxidase conjugate (ExtrAvidin; Sigma-Aldrich) was then added, and the reaction was developed as described before.

SDS-PAGE and Western blotting by the method of Suzuki et al., J. Clin. Invest., 119, 1668-1677 (2009). SDS-PAGE can separate serum and culture supernatants under reducing conditions using 4%-20% gradient slab gels (Bio-Rad). The amounts of protein loaded are adjusted to achieve equivalent amounts of IgA protein in each lane. The gels are blotted onto PVDF membranes and incubated with antibodies specific for IgA heavy chains (Vector Laboratories) or a biotin-labeled HAA lectin. HAA reacts with terminal GalNAc but not with sialylated GalNAc or GalNAc-Gal disaccharide. Gal-deficient IgA1 myeloma proteins (Mce or Ale poly), after separation by SDS-PAGE under reducing conditions and electroblotting onto PVDF membranes, served as antigens for analysis of glycan-specific IgG. The bound IgG is detected with an IgG-specific antibody, and the visualization of positive bands is done by subsequent incubation of the membrane with avidin-peroxidase conjugate, followed by enhanced chemiluminescence detection (Pierce; Thermo Scientific).

Dot-blot analysis. Gal-deficient IgA1 can be placed into the wells of a 96-well plate with PVDF membrane (MultiScreenHTS IP Filer Plate; Millipore) and blocked with SuperBlock (Pierce; Thermo Scientific). Serum or cell-culture supernatants (normalized to 0.5 μg IgG in each sample) are added and incubated overnight at 4° C. As a positive control, 0.5 μg of rIgG from an IgAN patient is used. The binding is detected with IgG-specific antibody, followed by subsequent incubation of the membrane with avidin-peroxidase conjugate, and the reaction was visualized using enhanced chemiluminescence (Pierce; Thermo Scientific), as described by the method of Suzuki et al., J. Clin. Invest., 119, 1668-1677 (2009) for Western blotting. Results are evaluated densitometrically. The intensity of rIgG binding to Gal-deficient IgA is assigned a value of 100%.

IgA Antibody-Binding Moieties.

Persons having ordinary skill in the biomedical art know that antibodies of several properties and activities, e.g., antibodies recognizing different antigens, having optional changes, etc., may be targeted by antibody-binding moieties described in this specification. In some embodiments, such antibodies include antibodies administered to a subject, e.g., for therapeutic purposes. In some embodiments, antibody-binding moieties described may bind antibodies toward different antigens and are useful for conjugating moieties of interest with several antibodies.

In some embodiments, an antibody-binding moiety, e.g., is or comprises a meditope agent moiety. A meditope agent is described in US 2019/0111149.

In some embodiments, an antibody-binding moiety, e.g., an antibody-binding moiety, can bind to human IgG. In some embodiments, an antibody-binding moiety, e.g., an antibody-binding moiety, can bind to an antibody selected from the Markush group of antibodies consisting of rabbit IgG, IgG1, IgG2, IgG3, and IgG4. In some embodiments, an antibody-binding moiety, e.g., an antibody-binding moiety, binds to IgG1, IgG2, and IgG4.

Methods of Making Agents.

Agents of the present disclosure may be prepared or isolated by synthetic or semi-synthetic methods or recombinant methods under the present disclosure. Certain technologies are described in the Examples. In some embodiments, polypeptide agents, e.g., cellular receptor-binding moiety peptide agents, may be prepared using biological expression systems. In some embodiments, provided agents are prepared synthetically. In some embodiments, provided agents are prepared using certain technologies described in WO2019/023501, which is incorporated herein in its entirety by reference.

Several technologies, e.g., those for preparing antibody-drug conjugates, may be used to prepare MATE agents. In many such technologies, conjugation is not selective regarding amino acid residue sites, and product compositions usually have several types of agents that may differ from each other regarding several target-binding moieties conjugated or conjugation sites. In some embodiments, the invention provides technologies that can be used for selective conjugation of target-binding moieties at particular amino acid residue sites.

In some embodiments, the invention provides a method of synthesis comprising the steps:

- contacting a first agent comprising a cellular receptor-binding moiety linked to a first reactive group optionally through a first linker with a second agent comprising an antibody moiety linked to a second reactive group optionally through a second linker, wherein the first reactive group reacts with a second reactive group, and
- forming a product agent comprising a cellular receptor-binding moiety and an antibody-binding moiety optionally through a linker.

In some embodiments, the invention provides a method of synthesis comprising the steps:

- contacting a first composition comprising a plurality of first agents, each independently comprising a cellular receptor-binding moiety linked to a first reactive group optionally through a first linker moiety, with a second composition comprising a plurality of second agents, each independently comprising an antibody moiety optionally linked to a second reactive group, optionally through a second linker moiety, wherein a product composition comprising a plurality of product agents, each independently comprising a cellular receptor-binding moiety and an antibody-binding moiety optionally through a linker, is formed.

Second Agent.

In another embodiment, the invention provides a composition including the agent and at least one additional agent comprising a moiety capable of binding to the antibody that forms the antibody moiety of the first compound.

In some embodiments, a first composition comprises a first agent described herein. In some embodiments, second agents independently comprise second reactive groups. In some embodiments, a second composition comprises a plurality of agents wherein each cellular receptor-binding moiety is independently a reactive group as described herein. In some embodiments, a second composition is an antibody composition, wherein antibodies in the composition are not chemically changed. In some embodiments, a second composition is an IVIG preparation. In some embodiments, a product composition comprises a plurality of agents wherein each cellular receptor-binding moiety is independently a cellular receptor-binding moiety as described herein.

In some embodiments, a cellular receptor-binding moiety in a product agent is a cellular receptor-binding moiety in a first agent. In some embodiments, an antibody moiety in a product agent is an antibody moiety in a second agent. In some embodiments, a second agent is an antibody agent, e.g., a monoclonal antibody, an antibody in a polyclonal antibody, an antibody in an IVIG preparation, etc. In embodiments, a second reactive group is a function group of an amino acid residue, e.g., —NH2 of Lys, —SH of Cys, etc. In embodiments, a second reactive group is —NH2 of a Lys residue, e.g., of a residue selected from K246 and K248 of an IgG1 heavy chain amino acid residues corresponding thereto, K251 and K253 of an IgG2 heavy chain and amino acid residues corresponding thereto, and K239 and K241 of an IgG4 heavy chain and amino acid residues corresponding thereto. In some embodiments, the invention provides selective reactions at particular amino acid residues of antibody moieties.

In some embodiments, a second reactive group is installed to an antibody moiety optionally through a linker. In some embodiments, a second reactive group is installed to an antibody moiety through a linker. In some embodiments, a second reactive group is selectively linked to certain location(s) of an antibody moiety, e.g., certain location(s) selected from K246 and K248 of an IgG1 heavy chain amino acid residues corresponding thereto, K251 and K253 of an IgG2 heavy chain and amino acid residues corresponding thereto, and K239 and K241 of an IgG4 heavy chain and amino acid residues corresponding thereto. In some embodiments, the invention provides selective reactions at particular amino acid residues of antibody moieties.

In some embodiments, the invention provides agents, each independently comprising an antibody-binding moiety that binds to an antibody agent, a reactive group, a cellular receptor-binding moiety, and optionally one or more linker moieties linking such groups/moieties. In some embodiments, such agents are useful as reaction partners, e.g., first agents) for conjugating moieties of interest, e.g., target-binding moieties, reactive groups, e.g., second reactive groups, to agents comprising antibody moieties, e.g., second agents. In some embodiments, the invention provides agents for conjugating moieties of interest to antibody moieties in several agents or antibody agents, e.g., monoclonal antibody agents, polyclonal antibody agents, antibody agents of IVIG preparations, etc. In embodiments, provided agents each comprise a cellular receptor-binding moiety, a reactive group, an antibody-binding moiety, and optionally one or more linker moieties (linkers) linking such moieties. In some embodiments, an antibody-binding moiety is part of a leaving group released after contacting this agent, e.g., a first agent, with an antibody moiety, e.g., of a second agent) and reacting a reactive group of this agent, e.g., a first reactive group of a first agent) with a reactive group of an antibody moiety, e.g., a second reactive group of a second agent, such as —NH2 of a Lys residue of an antibody protein. In some embodiments, provided technologies can provide improved conjugation efficiency, high selectivity, or fewer steps (sometimes, single step) to conjugation product agents. In some embodiments, a provided agent, e.g., a first agent, is a composition of matter of formula AGN301:

LG-RG-LRM-TBT (AGN301) or a salt thereof, wherein:

LG is a group comprising an antibody-binding moiety;

RG is a reactive group;

LRM is a linker; and

TBT is a cellular receptor-binding moiety.

Persons having ordinary skill in the biomedical art know that provided agents may have one or more stereocenters and may be present as a racemic or diastereomeric mixture. Those of skill in the biomedical art know there are many methods known in the biomedical art for the separation of isomers to obtain stereoenriched or stereopure isomers of those compounds, including but not limited to HPLC, chiral HPLC, fractional crystallization of diastereomeric salts, kinetic enzymatic resolution, e.g., by fungal-, bacterial-, or animal-derived lipases or esterases, and formation of covalent diastereomeric derivatives using an enantioenriched reagent.

Those of skill in the biomedical art know that several functional groups present in compounds of the present disclosure, such as aliphatic groups, alcohols, carboxylic acids, esters, amides, aldehydes, halogens, and nitriles, can be interconverted by techniques well known in the biomedical art including, but not limited to reduction, oxidation, esterification, hydrolysis, partial oxidation, partial reduction, halogenation, dehydration, partial hydration, and hydration. Smith & March, *March's Advanced Organic Chemistry: Reactions, Mechanisms, and Structure*, $5^{th}$ edition (John Wiley & Sons, 2001), the entirety of which is incorporated herein by reference. Such interconversions may require one or more techniques. Some methods for synthesizing compounds of the present disclosure are described below.

As known by persons having ordinary skill in the biomedical art, reaction partners are generally contacted with each other under conditions and for a time sufficient for producing the desired results, e.g., formation of product agents and compositions thereof to desired extents. Many reaction conditions and reaction times may be assessed and used to determine if they are suitable for the purposes described in the present disclosure. Some conditions, reaction times, assessments, etc., are described in the EXAMPLES.

In some embodiments, the invention provides products of provided processes, which have low levels of damage to antibody moieties compared to processes comprising steps performed for antibody-binding moiety removal but not for substantial conjugation of moieties of interest, e.g., target-binding moieties. In some embodiments, provided product agent compositions have high homogeneity, e.g., regarding the number of cellular receptor-binding moiety per antibody moiety, or positions of amino acid residues in antibody moieties conjugated to moieties of interest, compared to reference product compositions, e.g., those from technologies without using antibody-binding moieties, or using extra steps for antibody-binding moiety removal, e.g., not using reaction partners described which comprise a reactive group between an antibody-binding moiety and a cellular receptor-binding moiety.

In some embodiments, the invention provides a product agent comprising an antibody moiety, a cellular receptor-binding moiety, and optionally a linker moiety linking an antibody-binding moiety and a cellular receptor-binding moiety.

In some embodiments, the invention provides a composition comprising a plurality of agents, wherein each agent independently comprises:

an antibody moiety, a cellular receptor-binding moiety, and optionally a linker moiety linking an antibody-binding moiety and a cellular receptor-binding moiety.

In some embodiments, product agents are MATE agents. In some embodiments, an antibody agent moiety comprises the IgG Fc region. In some embodiments, an antibody moiety is connected to a cellular receptor-binding moiety through an amino group, optionally through a linker. In some embodiments, it is through a lysine residue wherein the amino group of the side chain is connected to a cellular receptor-binding moiety optionally through a linker, e.g., forming —NH—C(O)— as part of an amide group, a carbamate group, etc.

In some embodiments, selected locations of antibody moieties are used for conjugation. In some embodiments, K246 or K248 of an antibody agent (EU numbering or corresponding residues) are conjugation locations. In some embodiments, a conjugation location is K246 of the heavy chain (unless otherwise specified, locations herein include corresponding residues in, e.g., changed sequence, e.g., longer, shorter, rearranged, etc., sequences. In some embodiments, a location is K248 of the heavy chain. In some embodiments, a location is K288 or K290 of heavy chain. In some embodiments, a location is K288 of the heavy chain. In some embodiments, a location is K290 of heavy chain. In some embodiments, a location is K317. In some embodiments, an antibody moiety is a moiety of an IgG1 antibody or an antigen-binding fragment thereof. In some embodiments, an antibody moiety is a moiety of an IgG2 antibody or an antigen-binding fragment thereof. In some embodiments, an antibody moiety is a moiety of an IgG4 antibody or an antigen-binding fragment thereof. In some embodiments, a composition comprises a plurality of MATE agents, wherein antibody moieties of MATE agents are independently an antibody moiety of an IgG1, IgG2, or IgG4 antibody or an antigen-binding fragment thereof.

In some embodiments, antibody heavy chains are selectively conjugated/labeled over light chains.

In some embodiments, the invention provides a composition comprising a plurality of agents, each of which independently comprises:

an antibody moiety, a cellular receptor-binding moiety, and optionally a linker moiety linking the antibody moiety and the cellular receptor-binding moiety;

wherein antibody moieties of agents of the plurality comprise a common amino acid sequence, and agents of the plurality share a common cellular receptor-binding moiety independently of at least one common amino acid residue of the common amino acid sequence; and wherein about 1%-100% of all agents comprising an antibody moiety comprising the common amino acid sequence and the cellular receptor-binding moiety are agents of the plurality.

In some embodiments, the invention provides a composition comprising a plurality of agents, each of which independently comprises:

an antibody moiety, a cellular receptor-binding moiety, and optionally a linker moiety linking an antibody moiety and a cellular receptor-binding moiety; wherein agents of the plurality share the same or substantially the same antibody moiety and a cellular receptor-binding moiety at least one common location; and wherein about 1%-100% of all agents that comprise the antibody moiety and the cellular receptor-binding moiety are agents of the plurality.

Reactive Group

In some embodiments, provided agents, compounds, e.g., those useful as reaction partners such as first agents, comprise reactive groups, e.g., RG. In some embodiments, reactive groups, e.g., RG, are between antibody-binding moieties, e.g., ABT, and moieties of interest, e.g., MOI, and are optionally and independently linked to antibody-binding moieties and moieties of interest via linkers. In some embodiments, RG is a reaction group, as described herein.

In some embodiments, reactive groups, when used in agents that comprise no antibody-binding moieties, react slowly and provide a low level of, in some embodiments, substantially no conjugation of moieties of interest with target agents. Combination of reactive groups with antibody-binding moieties in the same agents, e.g., as in compounds of formula AGN301 or salts thereof, can promote reactions between reactive groups and target agents, enhance reaction efficiency, reduce side reactions, or improve reaction selectivity, e.g., in terms of target sites wherein conjugation of moieties of interest with target agents occurs.

Reactive groups in agents can react with several types of groups in target agents. In some embodiments, reactive groups in agents selectively react with amino groups of target agents, e.g., —$NH_2$ groups on side chains of lysine residues of proteins. In some embodiments, reactive groups, when used in agents, e.g., those of formula AGN301 or salts thereof, selectively react with particular sites of target agents, e.g., as shown in examples herein, one or more of K246, K248, K288, K290, K317, etc., of IgG1, K251, K 253, etc. for IgG2, K239, K241 for IgG4, etc. In embodiments, a site is K246 or K248 of an antibody heavy chain. In some embodiments, sites are K246 or K248 of an antibody heavy chain. In some embodiments, a site is K246 of an antibody heavy chain. In some embodiments, a site is K248 of an antibody heavy chain. In some embodiments, a site is K288 or K290 of an antibody heavy chain. In some embodiments, a site is K288 of an antibody heavy chain. In some embodiments, a site is K290 of an antibody heavy chain. In some embodiments, a site is K317. In some embodiments, a site is K414 of an antibody heavy chain. In some embodiments, a site is K185 of an antibody light chain. In some embodiments, a site is K187 of an antibody light chain. In some embodiments, sites are K251 or K253 of an IgG2 heavy chain. In some embodiments, a site is K251 of an IgG2 heavy chain. In some embodiments, a site is K253 of an IgG2 heavy chain. In some embodiments, sites are K239 or K241 of an IgG4 heavy chain. In some embodiments, a site is K239 of an IgG4 heavy chain. In some embodiments, a site is K241 of an IgG4 heavy chain. In some embodiments, conjugation selectively occurs at one or more heavy chain sites over light chain sites. In some embodiments, for technologies without antibody-binding moieties, conjugation occurs at light chain sites more than heavy chain sites.

In some embodiments, a reactive group, e.g., RG, is or comprises an ester group. In some embodiments, a reactive group, e.g., RG, is or comprises an electrophilic group, e.g., a Michael acceptor.

In some embodiments, a reactive group, e.g., RG, is or comprises $-L^{RG1}-L^{RG2}-$, wherein each of $L^{RG1}$ and $L^{RG2}$ is independently L as described herein. In some embodiments, a reactive group, e.g., RG, is or comprises $-L^{LG4}-L^{RG1}-L^{RG2}-$, wherein each variable is as described herein. In some embodiments, a reactive group, e.g., RG, is or comprises $-L^{LG3}-L^{LG4}-L^{RG1}-L^{RG2}-$, wherein each variable is as described herein. In some embodiments, a reactive group, e.g., RG, is or comprises $-L^{LG2}-L^{LG3}-L^{LG4}-L^{RG1}-L^{RG2}-$, wherein each variable is as described herein. In some embodiments, a reactive group, e.g., RG, is or comprises $-L^{LG4}-L^{RG2}-$, wherein each variable is as described herein. In some embodiments, a reactive group, e.g., RG, is or comprises $-L^{LG3}-L^{LG4}-L^{RG2}-$, wherein each variable is as described herein. In some embodiments, a reactive group, e.g., RG, is or comprises $-L^{LG2}-L^{LG3}-L^{LG4}-L^{RG2}-$, wherein each variable is as described herein.

In some embodiments, $L^{LG4}$ is —O—. In some embodiments, $L^{LG4}$ is —N(R)—. In some embodiments, $L^{LG4}$ is —NH—.

In some embodiments, $L^{LG3}$ is or comprises an optionally substituted aryl ring. In some embodiments, $L^{LG3}$ is or comprises a phenyl ring. In some embodiments, an aryl or phenyl ring is substituted. In some embodiments, a substituent is an electron-withdrawing group, e.g., $—NO_2$, —F, etc.

In some embodiments, $L^{RG1}$ is a covalent bond. In some embodiments, $L^{RG1}$ is not a covalent bond. In some embodiments, $L^{RG1}$ is $—S(O)_2—$.

In some embodiments, $L^{RG2}$ is —C(O)—. In some embodiments, a reactive group is or comprises $-L^{LG4}$-C(O)—, wherein each variable is as described herein. In some embodiments, a reactive group is or comprises $-L^{LG3}-L^{LG4}$-C(O)—, wherein each variable is as described herein. In some embodiments, a reactive group comprises $-L^{LG2}-L^{LG3}-L^{LG4}$-C(O)—, wherein each variable is as described herein.

In some embodiments, $L^{RG2}$ is $-L^{RG3}-C({=}CR^{RG1}R^{RG2})—CR^{RG3}R^{RG4}—$, wherein each of $R^{RG1}$, $R^{RG2}$, $R^{RG3}$ and $R^{RG4}$ is independently -L-R', and $L^{RG3}$ is —C(O)—, —C(O)O—, —C(O)N(R')—, —S(O)—, $—S(O)_2—$, —P(O)(OR')—, —P(O)(SR')—, or $—P(O)(N(R')_2)—$. In some embodiments, each of $R^{RG1}$, $R^{RG2}$, $R^{RG3}$, and $R^{RG4}$ is independently R'. In some embodiments, one or more of $R^{RG1}$, $R^{RG2}$, $R^{RG3}$ and $R^{RG4}$ is independently —H. In embodiments, $L^{RG3}$ is —C(O)—. In some embodiments, $L^{RG3}$ is —C(O)O—. In some embodiments, —O—, —N(R')—, etc. of $L^{RG3}$ is bonded to $L^{PM}$.

In some embodiments, $R^{RG1}$ is —H. In embodiments, $R^{RG3}$ is —H.

In some embodiments, $L^{RG2}$ is optionally substituted $-L^{RG3}-C({=}CHR^{RG2})—CHR^{RG4}—$, wherein each variable is as described herein.

In some embodiments, $R^{RG2}$ and $R^{RG4}$ are taken with their intervening atoms to form an optionally substituted ring as described herein. In some embodiments, a formed ring is an optionally substituted 3-10 membered monocyclic or bicyclic ring having 0-5 heteroatoms. In some embodiments, a formed ring is an optionally substituted 3-10-membered cycloaliphatic ring. In some embodiments, a formed ring is selected from the Markush group consisting of optionally substituted cycloaliphatic rings consisting of a 3-8 membered cycloaliphatic ring, a 5-8 membered cycloaliphatic ring, a 5-membered cycloaliphatic ring, a 6-membered cycloaliphatic ring, and a 7-membered cycloaliphatic ring. In some embodiments, a formed ring is substituted. In some embodiments, a formed ring is not substituted. In some embodiments, a formed ring has no more unsaturation than the double bond in $C({=}CHR^{RG2})$ or $C({=}CR^{RG1}R^{RG2})$.

In some embodiments, $—C({=}CHR^{RG2})—CHR^{RG4}$ or $—C({=}CR^{RG1}R^{RG2})—CR^{RG3}R^{RG4}$ is optionally substituted

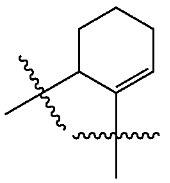
or is
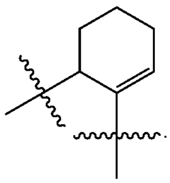.

In some embodiments, $—[C({=}CHR^{RG2})—CHR^{RG4}]-L^{RG3}-$ or $—[C({=}CR^{RG1}R^{RG2})—CR^{RG3}R^{RG4}]-L^{RG3}-$ is optionally substituted

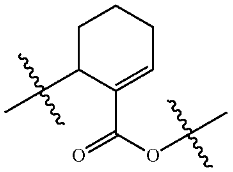
or is
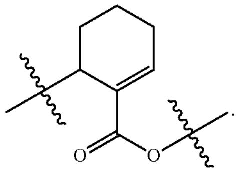.

In some embodiments, $-L^{RG1}-[C({=}CHR^{RG2})—CHR^{RG4}]-L^{RG3}-$ or $-L^{RG1}-[C({=}CR^{RG1}R^{RG2})—CR^{RG3}R^{RG4}]-L^{RG3}-$ is optionally substituted

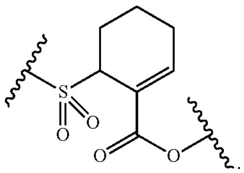 [SMILES: *OC(=O)C1=CCCCC1S(*)(=O)=O].

In some embodiments, $-L^{RG1}-[C({=}CHR^{RG2})—CHR^{RG4}]-L^{RG3}-$ or $-L^{RG1}-[C({=}CR^{RG1}R^{RG2})—CR^{RG3}R^{RG4}]-L^{RG3}-$ is optionally substituted.

In some embodiments, a reactive group is a structure selected from TABLE 3 below. In some embodiments, $-L^{LG2}-L^{LG3}-L^{LG4}-L^{RG1}-L^{RG2}-$ is a structure selected from TABLE 3 below. In some embodiments, $-L^{LG2}-L^{LG3}-L^{LG4}-L^{RG1}-$ is a structure selected from TABLE 3 below.

TABLE 3
| Certain structures as examples |
| --- |
| 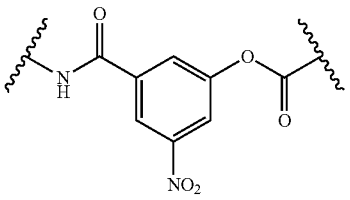 [SMILES: *NC(=O)c1cc(OC(*)=O)cc([N+](=O)[O-])c1] |
| 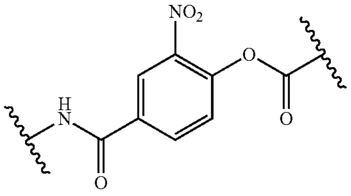 [SMILES: *NC(=O)c1ccc(OC(*)=O)c([N+](=O)[O-])c1] |
| 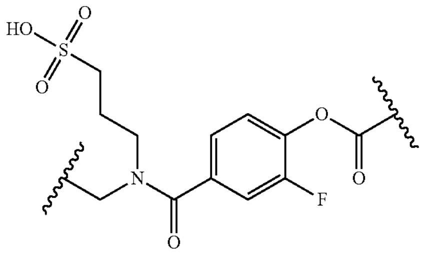 [SMILES: *CN(CCCS(=O)(=O)O)C(=O)c1ccc(OC(*)=O)c(F)c1] |
| 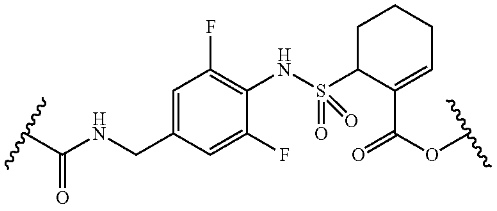 [SMILES: *OC(=O)C1=CCCCC1S(=O)(=O)Nc1c(F)cc(CNC(*)=O)cc1F] |
| 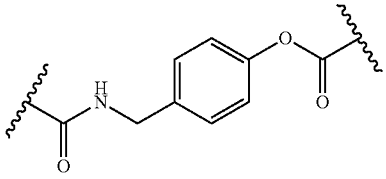 [SMILES: *C(=O)NCc1ccc(OC(*)=O)cc1] |
| 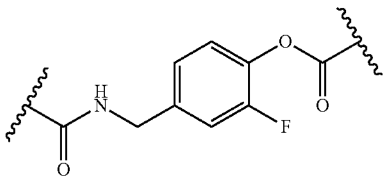 [SMILES: *C(=O)NCc1ccc(OC(*)=O)c(F)c1] |
| 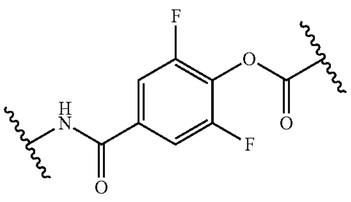 [SMILES: *NC(=O)c1cc(F)c(OC(*)=O)c(F)c1] |
TABLE 3-continued
| Certain structures as examples |
| --- |
| 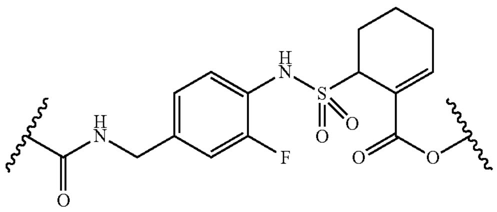 [SMILES: *OC(=O)C1=CCCCC1S(=O)(=O)Nc1ccc(CNC(*)=O)cc1F] |
| 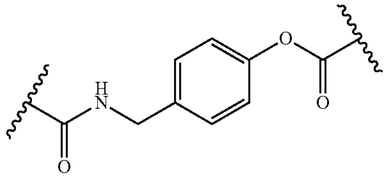 [SMILES: *C(=O)NCc1ccc(OC(*)=O)cc1] |
| 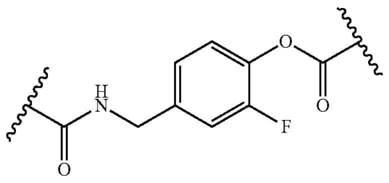 [SMILES: *C(=O)NCc1ccc(OC(*)=O)c(F)c1] |
| 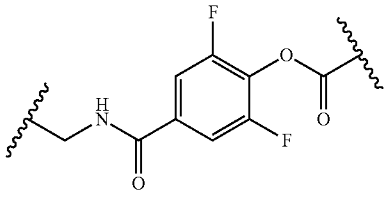 [SMILES: *CNC(=O)c1cc(F)c(OC(*)=O)c(F)c1] |
| 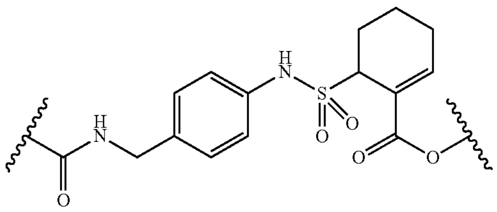 [SMILES: *OC(=O)C1=CCCCC1S(=O)(=O)Nc1ccc(CNC(*)=O)cc1] |
| 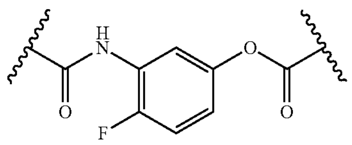 [SMILES: *C(=O)Nc1cc(OC(*)=O)ccc1F] |
| 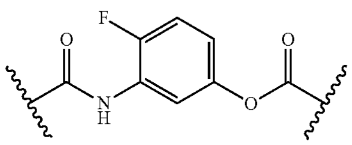 [SMILES: *C(=O)Nc1cc(OC(*)=O)ccc1F] |
| 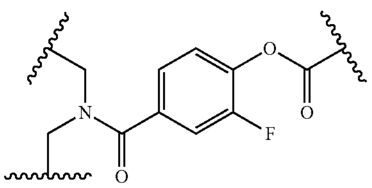 [SMILES: *CN(C*)C(=O)c1ccc(OC(*)=O)c(F)c1] |

TABLE 3-continued

Certain structures as examples

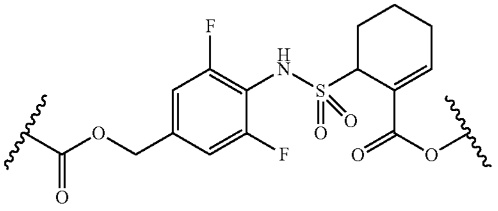 [SMILES: *OC(=O)C1=CCCCC1S(=O)(=O)Nc1c(F)cc(COC(*)=O)cc1F]

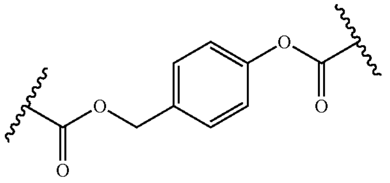 [SMILES: *C(=O)OCc1ccc(OC(*)=O)cc1]

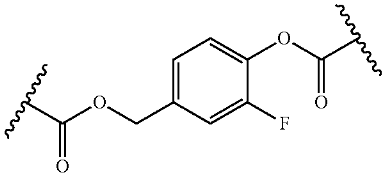 [SMILES: *C(=O)OCc1ccc(OC(*)=O)c(F)c1]

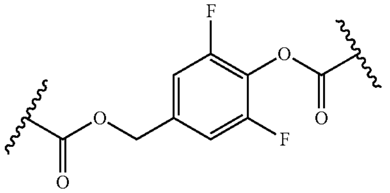 [SMILES: *C(=O)OCc1cc(F)c(OC(*)=O)c(F)c1]

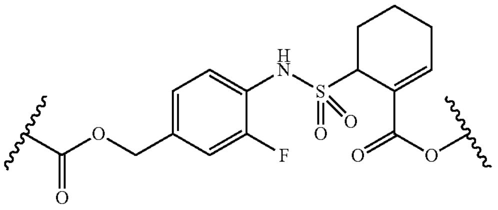 [SMILES: *OC(=O)C1=CCCCC1S(=O)(=O)Nc1ccc(COC(*)=O)cc1F]

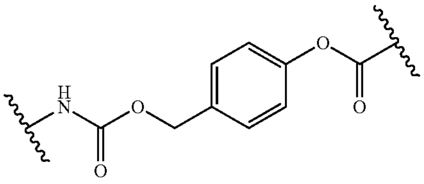 [SMILES: *NC(=O)OCc1ccc(OC(*)=O)cc1]

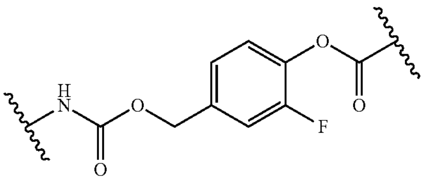 [SMILES: *NC(=O)OCc1ccc(OC(*)=O)c(F)c1]

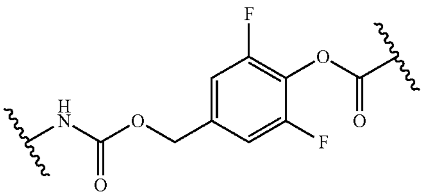 [SMILES: *NC(=O)OCc1cc(F)c(OC(*)=O)c(F)c1]

TABLE 3-continued

Certain structures as examples

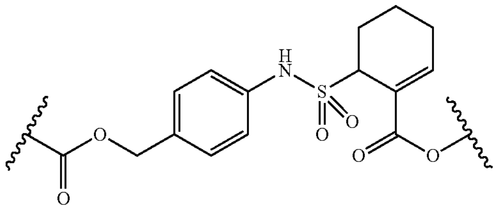 [SMILES: *OC(=O)C1=CCCCC1S(=O)(=O)Nc1ccc(COC(*)=O)cc1]

In some embodiments, $-L^{LG4}-L^{RG2}-$ is —O—C(O)— or —S—C(O)—. In some embodiments, $-L^{LG4}-L^{RG1}-L^{RG2}-$ is —S—C(O)—.

In some embodiments, $-L^{LG4}-L^{RG2}-$ is —N(—)—C(O)—, wherein N is a ring atom of an optionally substituted heteroaryl ring. In some embodiments, $-L^{LG4}-L^{RG2}-$ is —N(—)—C(O)—, wherein N is a ring atom of $L^{LG4}$, which is or comprises an optionally substituted heteroaryl ring. In some embodiments, $-L^{LG4}-L^{RG2}-$ is —N(–)-C(O)—O—, wherein N is a ring atom of $L^{LG4}$, which is or comprises an optionally substituted heteroaryl ring.

In some embodiments, $L^{RG2}$ is optionally substituted —$CH_2$—C(O)—, wherein —$CH_2$— is bonded to an electron-withdrawing group comprising or connected to an antibody-binding moiety. In some embodiments, $L^{RG2}$ is optionally substituted —$CH_2$— bonded to an electron-withdrawing group comprising or connected to an antibody-binding moiety. In some embodiments, $L^{RG1}$ is an electron-withdrawing group. In some embodiments, $L^{RG1}$ is selected from the Markush group consisting of —C(O)—, —S(O)—, —$S(O)_2$—, —P(O(OR)—, —P(O(SR)—, —P(O(N(R)$_2$)—, —OP(O(OR)—, —OP(O(SR)—, and —OP(O(N(R)$_2$)—.

In some embodiments, $L^{RG2}$ is optionally substituted —$CH_2$—C(O)—, wherein —$CH_2$— is bonded to a leaving group comprising or connected to an antibody-binding moiety. In some embodiments, $L^{RG2}$ is optionally substituted —$CH_2$— bonded to a leaving group comprising or connected to an antibody-binding moiety. In some embodiments, $L^{RG1}$ is selected from the Markush group consisting of —O—C(O)—, —$OS(O)_2$—, —OP(O(OR)—, —OP(O (SR)—, and —OP(O(N(R)$_2$)—.

In some embodiments, a reactive group reacts with an amino group of a target agent. In some embodiments, an amino group is —$NH_2$ of the side chain of a lysine residue.

In some embodiments, a target agent is a protein agent. In some embodiments, a target agent is an antibody agent. In some embodiments, a reactive group reacts with an amino acid residue of this protein or antibody agent. In some embodiments, an amino acid residue is a lysine residue. In some embodiments, a reactive group reacts with —$NH_2$ of the side chain of a lysine residue. In some embodiments, a reactive group is or comprises —C(O)—O—, reacts with —$NH_2$, e.g., of the side chain of a lysine residue), and forms an amide group —C(O)—O— with the —$NH_2$.

In some embodiments, reactive groups are at terminal locations, e.g., a first reactive group, a second reactive group, etc. In some embodiments, agents comprise first reactive groups linked to target-binding moieties, optionally through linker moieties, and do not have antibody-binding moieties.

In some embodiments, the invention provides methods for preparing a composition comprising a plurality of agents, wherein each agent independently comprises:

an antibody moiety, a cellular receptor-binding moiety, and optionally a linker moiety linking an antibody moiety and a cellular receptor-binding moiety;

which method comprises:

contacting a plurality of agents, each independently comprising a reactive group with a plurality of antibody agents.

In some embodiments, an agent comprising a reactive group comprises an antibody-binding moiety, a cellular receptor-binding moiety, and optionally a linker. In some embodiments, agents comprising a reactive group share the same cellular receptor-binding moiety. In some embodiments, agents comprising a reactive group share the same structure. In some embodiments, antibody molecules are of such structures, properties, or activities to provide antibody moieties in the agents described. In some embodiments, a plurality of antibody molecules comprises two or more IgG subclasses. In some embodiments, a plurality of antibody molecules comprises IgG1. In some embodiments, a plurality of antibody molecules comprises IgG2. In some embodiments, a plurality of antibody molecules comprises IgG4. In some embodiments, a plurality of antibody molecules comprises IgG1 and IgG2. In some embodiments, a plurality of antibody molecules comprises IgG1, IgG2, and IgG4. In some embodiments, a plurality of antibody molecules comprises IgG1, IgG2, IgG3 and IgG4. In some embodiments, a plurality of antibody molecules is IVIG antibody molecules.

In some embodiments, provided agents comprise a reactive group, e.g.,

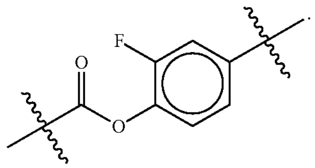

In some embodiments, —C(O)— is connected to a cellular receptor-binding moiety or a moiety comprising —(Xaa)y-, optionally through a linker, and the other end is connected to an antibody-binding moiety. In some embodiments,

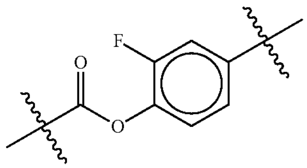

reacts with an amino group of another moiety, e.g., an antibody moiety, forming an amide group with the moiety and releasing a moiety comprising an antibody-binding moiety. In some embodiments, an amino group is —$NH_2$ of a lysine side chain. In some embodiments, —C(O)— is connected to a cellular receptor-binding moiety or a moiety comprising —(Xaa)y-, optionally through a linker, and the other end is connected to R' or an optional substituent. In some embodiments, provided agents comprise optionally substituted

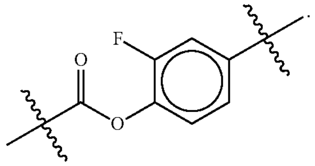

Such reactive groups may be useful for conjugation with detection, diagnosis, or therapeutic agents. Persons having ordinary skill in the biomedical art know that several agents and technologies, e.g., click chemistry reactions based on functional groups such as amino groups, can be used for conjugation.

In some embodiments, antibody-binding moieties bind to Fc regions of antibodies. In some embodiments, reactions occur at residues at Fc regions. In some embodiments, target-binding moieties are conjugated to residues of Fc regions, optionally through linker moieties. In some embodiments, a residue is a Lys residue. In some embodiments, an antibody is or comprises IgG1. In some embodiments, an antibody is or comprises IgG2. In some embodiments, an antibody is or comprises IgG4. In some embodiments, an antibody composition used in a method comprises IgG1 and IgG2. In some embodiments, an antibody composition used in a method comprises IgG1, IgG2, and IgG4. In some embodiments, an antibody composition used in a method comprises IgG1, IgG2, IgG3, and IgG4.

In some embodiments, a product comprises IgG1, IgG2, IgG3, and IgG4. In some embodiments, a product composition comprises IgG1 and IgG2, IgG2, and IgG4.

In some embodiments, agents comprising antibody moieties provide one or more antibody immune activities, e.g., for recruiting one or more types of immune cells or providing short-term and long-term immune activities. In some embodiments, provided agents comprising antibody moieties do not significantly reduce one or more or substantially all relevant antibody immune activities. In some embodiments, provided agents comprising antibody moieties improve one or more or substantially all relevant antibody immune activities, e.g., compared to antibody moieties themselves. In some embodiments, agents provide comparable or better stability compared to antibody moieties by themselves, e.g., home time in blood. In some embodiments, antibody moieties in provided agents can bind to FcRy of immune cells, e.g., several FcRy of immune effector cells for desired immune activities; typically, at comparable or better levels. In some embodiments, antibody moieties in provided agents have comparable Fab/antigen binding capabilities. In some embodiments, antibody moieties in provided agents have comparable Fab/antigen binding capabilities. In some embodiments, antibody moieties in provided agents provide FcRn binding. In some embodiments, antibody moieties in provided agents provide FcRn binding, e.g., for antibody recycling or prolonged half-life. In some embodiments, provided technologies are useful for changing blood-derived IgG products as provided technologies are suitable for and can use all IgG subclasses.

In some embodiments, a provided method comprises one step described below. In some embodiments,

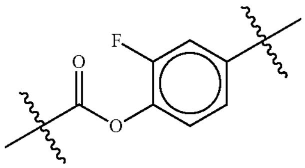

reacts with an amino group of a lysine side chain to form an amide bond with an antibody molecule and releases, or a salt form thereof.

Linker Moieties

In some embodiments, moieties are optionally connected to each other through linker moieties. In some embodiments, a reactive group, e.g., RG, is connected to a cellular receptor-binding moiety, e.g., TBT, through a linker, e.g., $L^{RM}$. In some embodiments, a moiety, e.g., LG, may also comprise one or more linkers, e.g., $L^{LG1}$, $L^{LG2}$, $L^{LG3}$, $L^{LG4}$, etc., to link several parts. In some embodiments, $L^{LG}$ is a linker moiety described. In some embodiments, $L^{LG1}$ is a linker moiety described. In some embodiments, $L^{LG2}$ is a linker moiety described. In some embodiments, $L^{LG3}$ is a linker moiety described. In some embodiments, $L^{LG4}$ is a linker moiety described. In some embodiments, $L^{RM}$ is a linker moiety described. In some embodiments, $L^{PM}$ is L, as described herein. In some embodiments, $L^{PM}$ is a linker moiety described. In some embodiments, $L^{PM}$ is L, as described herein.

Under the present disclosure, linker moieties of several types or for several purposes, e.g., those used in antibody-drug conjugates, etc., may be used.

Linker moieties can be bivalent or polyvalent, depending on how they are used. In some embodiments, a linker moiety is bivalent. In some embodiments, a linker is polyvalent and connects over two moieties.

In some embodiments, a linker moiety, e.g., $L^z$ (wherein z represents superscript text, e.g., $L^{PM}$, $L^{RM}$, $L^{LG}$, $L^{LG1}$, etc., is or comprises L.

In some embodiments, L is a covalent bond, or a bivalent or polyvalent optionally substituted $C_{1-100}$ group comprising one or more aliphatic, aryl, heteroaliphatic having 1-20 heteroatoms, heteroaromatic having 1-20 heteroatoms, or any combinations thereof, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —$C(R')_2$—, —O—, —S—, —S—S—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—$C(R')_2$—$C(R')_2$—$)_n$]—, wherein n is 1-20. The linker optionally has a cyclic group, Cy, defined below, and a reactive group, RG, as defined below. In some embodiments, each amino acid residue independently has the structure of —$N(R^{a1})$-$L^{a1}$-$C(R^{a2})(R^{a3})$-$L^{a2}$-CO— or a salt form thereof.

In some embodiments, L is bivalent. In some embodiments, L is a covalent bond.

In some embodiments, L is a bivalent or optionally substituted group selected from $C_{1-00}$ aliphatic and $C_{1-100}$ heteroaliphatic having 1-50 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —$C(R')_2$—, —O—, —S—, —S—S—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—$C(R')_2$—$C(R')_2$—$)_n$]—. In some embodiments, L is a bivalent or optionally substituted group selected from $C_{1-20}$ aliphatic and $C_{1-20}$ heteroaliphatic having 1-10 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —$C(R')_2$—, —O—, —S—, —S—S—, —N(R')—, —C(O)—, —C(S)—, —C(NR)—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—$C(R')_2$—$C(R')_2$—$)_n$]—. In some embodiments, L is a bivalent or optionally substituted group selected from $C_{1-20}$ aliphatic wherein one or more methylene units of the group are optionally and independently replaced with —C≡C—, -Cy-, —$C(R')_2$—, —O—, —S—, —S—S—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—$C(R')_2$—$C(R')_2$—$)_n$]—. In some embodiments, L is a bivalent or optionally substituted $C_{1-20}$ aliphatic group, wherein one or more methylene units of the group are optionally and independently replaced with —C≡C—, -Cy-, —$C(R')_2$—, —O—, —S—, —S—S—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, —C(O)S—, —C(O)O—, an amino acid residue or —[(—O—$C(R')_2$—$C(R')_2$—$)_n$]—. In some embodiments, L is a bivalent or optionally substituted $C_{1-100}$ aliphatic group, wherein one or more methylene units of the group are optionally and independently replaced with —C≡C—, -Cy-, —$C(R')_2$—, —O—, —N(R')—, —C(O)—, —C(S)—, —C(NR')—, —C(O)N(R')—, —C(O)$C(R')_2$N(R')—, —N(R')C(O)N(R')—, —N(R')C(O)O—, —S(O)—, —$S(O)_2$—, —$S(O)_2$N(R')—, an amino acid residue or —[(—O—$C(R')_2$—$C(R')_2$—$)_n$]—. In some embodiments, L is a bivalent or optionally substituted $C_{1-50}$ aliphatic group, wherein one or more methylene units of the group are optionally and independently replaced as described herein. In some embodiments, L is a bivalent or optionally substituted $C_{1-40}$ aliphatic group, wherein one or more methylene units of the group are optionally and independently replaced as described herein. In some embodiments, L is a bivalent or optionally substituted $C_{1-20}$ aliphatic group, wherein one or more methylene units of the group are optionally and independently replaced as described herein. In some embodiments, L is a bivalent or optionally substituted $C_{1-10}$ aliphatic group, wherein one or more methylene units of the group are optionally and independently replaced as described herein. In some embodiments, L is a bivalent or optionally substituted $C_{1-100}$ alkylene group, wherein one or more methylene units of the group are optionally and independently replaced as described herein. In some embodiments, L is a bivalent or optionally substituted $C_{1-50}$ alkylene group, wherein one or more methylene units of the group are optionally and independently replaced as described herein. In some embodiments, L is a bivalent or optionally substituted $C_{1-40}$ alkylene group, wherein one or more methylene units of the group are optionally and independently replaced as described herein. In some embodiments, L is a bivalent or optionally substituted $C_{1-20}$ alkylene group, wherein one or more methylene units of the group are optionally and independently replaced as described herein. In some embodiments, L is a bivalent or optionally substituted $C_{1-10}$ alkylene group, wherein one or more methylene units of the group are optionally and independently replaced as described herein.

In some embodiments, a linker moiety, e.g., L, $L^{PM}$, $L^{RM}$, etc., comprises an acidic group, e.g., $—S(O)_2OH$.

In some embodiments, L is or comprises $—[(—O—C(R')_2—C(R')_2—)_n]—$. In some embodiments, L is or comprises $—[(—O—CH_2—CH_2—)_n]—$. In some embodiments, L is $—[(—CH_2—CH_2—O)_6]—CH_2—CH_2—$. In some embodiments, L is $—[(—CH_2—CH_2—O)_8]—CH_2—CH_2—$. In some embodiments, $—CH_2—CH_2—O—$ is bonded to an antibody-binding moiety at a $—CH_2—$. In some embodiments, $—CH_2—CH_2—O—$ is bonded to a cellular receptor-binding moiety at a $—CH_2—$. In some embodiments, $L^{PM}$ is such L as described herein. In some embodiments, $L^{RM}$ is such L as described herein.

In some embodiments, a linker moiety, e.g., L, is or comprises one or more $—(CH_2)_n—O—$, wherein each n is independently 1-20. In some embodiments, it is or comprises one or more $—[(CH_2)_n—O]_m—$, wherein each n is independently 1-20, and m is 1-100. In some embodiments, it comprises two or more $—[(CH_2)_n—O]_m—$, wherein each n is independently 1-20, and each m is 1-100. In some embodiments, it is or comprises one or more $—(O)C—[(CH_2)_nO]_m(CH_2)_nNH—$, $—[(CH_2)_nO]_mNHC(O)[(CH_2)_nO]_mNH—$, $—[(CH_2)_nO]_m\{NHC(O)[(CH_2)_nO]_m\}_pNH—$ wherein each n is independently 1-20, and each m is independently 1-100, and where each p is independently 1 to 10. In some embodiments, n is 1-10. In some embodiments, n is 1-5. In some embodiments, each n is 2. In some embodiments, m is 1-50. In some embodiments, m is 1-40. In some embodiments, m is 1-30. In some embodiments, m is 1-20. In some embodiments, m is 1-10. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20.

In some embodiments, a linker moiety, or L, is or comprises $—(CH_2CH_2O)_n—$, wherein each $—CH_2—$ is independently and optionally substituted, and n is 1-20. In some embodiments, a linker moiety, or L, is or comprises $—(CH_2)_n—O—(CH_2CH_2O)_n—(CH_2)_n—$, wherein each n is independently 1-10, and each $—CH_2—$ is independently and optionally substituted.

In some embodiments, a linker moiety is trivalent or polyvalent. In some embodiments, a linker moiety is L, as described herein, and L is trivalent or polyvalent. In some embodiments, L is trivalent. In some embodiments, L is $—CH_2—N(—CH_2—)—C(O)—$.

In some embodiments, a linker moiety, e.g., L, comprises one or more amino acid residues or analogs thereof.

In some embodiments, a linker moiety, e.g., L, $L^{RM}$, etc., is or comprises a reactive group as described herein. In some embodiments, an agent comprises an antibody-binding moiety and a cellular receptor-binding moiety linked through a linker comprising a reactive group. In some embodiments, a reactive group can react with a lysine residue of an antibody in an aqueous buffer, as described herein. In some embodiments, a reactive group comprises —C(O)—O—. In some embodiments, a reactive group comprises —C(O)—O—, wherein —O— is bonded to an optionally substituted aryl group. In some embodiments, a reactive group comprises —C(O)—O—, wherein —O— is bonded to an aryl group substituted with one or more electron-withdrawing groups. In some embodiments, one or more of each electron-withdrawing group is independently selected from $—NO_2$ and —F. In embodiments, an aryl group has the structure of

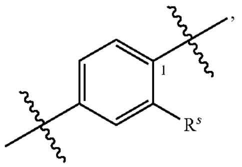

wherein $R^s$ is halogen, $—NO_2$, —F, -L-R', —C(O)-L-R', —S(O)-L-R', $—S(O)_2$-L-R', or $—P(O)(-L-R')_2$. In some embodiments, an aryl group has the structure of

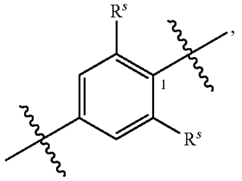

wherein each $R^s$ is independently halogen, $—NO_2$, —F, -L-R', —C(O)-L-R', —S(O)-L-R', $—S(O)_2$-L-R', or $—P(O)(-L-R')_2$. In some embodiments, an aryl group is

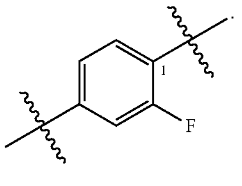

In some embodiments, an aryl group is

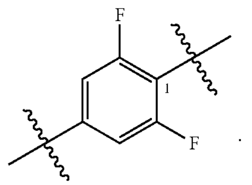 [SMILES: *c1cc(F)c(*)c(F)c1]

In some embodiments, C1 is bound to the —O— of —C(O)—O—. In some embodiments, a cellular receptor-binding moiety is at the side of —C(O)— and an antibody-binding moiety is at the side of —O—.

In some embodiments, a linker moiety, e.g., L, $L^{RM}$, etc., comprises a reactive group, wherein upon contact with an antibody, the reactive group reacts with a group of the antibody and conjugates a cellular receptor-binding moiety, or a moiety comprising —(Xaa)y-, to the antibody optionally through a linker. In some embodiments, a reactive group comprises

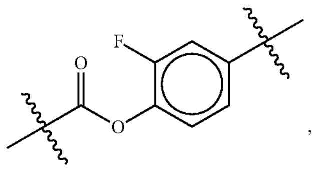

, wherein the —C(O)— is connected to a cellular receptor-binding moiety or a moiety comprising —(Xaa)y-, optionally through a linker. In some embodiments, a reactive group is or comprises

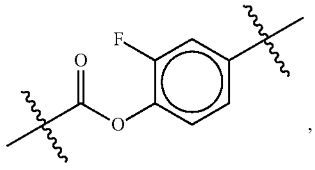

, wherein the —C(O)— is connected to a cellular receptor-binding moiety, or a moiety comprising —(Xaa)y-, optionally through a linker and the other end of the reactive group is connected to an antibody-binding moiety.

In some embodiments, a linker moiety, e.g., L) is or comprises one or more, e.g., 1, 2, 3, 4, 5, 6, 7, 8, 9, 10, 11, 12, 13, 14, 15, 16, 17, 18, 19, 20 or more) polyethylene glycol units. In some embodiments, a linker moiety comprises $-(CH_2CH_2O)_n-$, wherein n is described in this specification. In some embodiments, one or more methylene units of L are independently replaced with $-(CH_2CH_2O)_n-$.

In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, a linker moiety, e.g., L, is or comprises one or more, e.g., 1, 2, 3, 4, 5, 6, 7, 8, 9, 10, 11, 12, 13, 14, 15, 16, 17, 18, 19, 20 or more) amino acid residues. In some embodiments, one or more methylene units of L are independently replaced with an amino acid residue. In some embodiments, one or more methylene units of L are independently replaced with an amino acid residue, wherein the amino acid residue is of an amino acid of formula LNK101 or a salt thereof. In some embodiments, one or more methylene units of L are independently replaced with an amino acid residue, wherein each amino acid residue independently has the structure of $-N(R^{a1})-L^{a1}-C(R^{a2})(R^{a3})-L^{a2}-CO-$ or a salt form thereof.

In some embodiments, a linker moiety comprises one or more moieties, e.g., amino, carbonyl, etc., that can be used for connection with other moieties. In some embodiments, a linker moiety comprises one or more —NR'—, wherein R' is described in this specification. In some embodiments, —NR'— improves solubility. In some embodiments, —NR'— serves as connection points to another moiety. In some embodiments, R' is —H. In embodiments, one or more methylene units of L are independently replaced with —NR'—, wherein R' is as described in this specification.

In some embodiments, a linker moiety, e.g., L, comprises a —C(O)— group, which can be used for connections with a moiety. In some embodiments, one or more methylene units of L are independently replaced with —C(O)—.

In some embodiments, a linker moiety, e.g., L, comprises a —NR'— group, which can be used for connections with a moiety. In some embodiments, one or more methylene units of L are independently replaced with —N(R')—.

In some embodiments, a linker moiety, e.g., L, comprises a —C(O)NR'— group, which can be used for connections with a moiety. In some embodiments, one or more methylene units of L are independently replaced with —C(O)N(R')—.

In some embodiments, a linker moiety, e.g., L, comprises a $-C(R')_2-$ group. In some embodiments, one or more methylene units of L are independently replaced with $-C(R')_2-$. In some embodiments, $-C(R')_2-$ is —CHR'—. In some embodiments, R' is $-(CH_2)_2C(O)NH(CH_2)_{11}COOH$. In some embodiments, R' is $-(CH_2)_2COOH$. In some embodiments, R' is —COOH.

In some embodiments, a linker moiety is or comprises one or more ring moieties, e.g., one or more methylene units of L are replaced with -Cy-. In some embodiments, a linker moiety, e.g., L, comprises an aryl ring. In some embodiments, a linker moiety, e.g., L, comprises a heteroaryl ring. In some embodiments, a linker moiety, e.g., L, comprises an aliphatic ring. In some embodiments, a linker moiety, e.g., L, comprises a heterocyclyl ring. In some embodiments, a linker moiety, e.g., L, comprises a polycyclic ring. In some embodiments, a ring in a linker moiety, e.g., L, is 3-20 membered. In some embodiments, a ring is 5-membered. In some embodiments, a ring is 6-membered. In some embodiments, a ring in a linker is a product of a cycloaddition reaction, e.g., click chemistry and variants thereof, used to link different moieties.

In some embodiments, a linker moiety, e.g., L, is or comprises

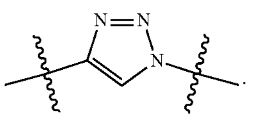 [SMILES: *c1cn(*)nn1]

In some embodiments, a methylene unit of L is replaced with

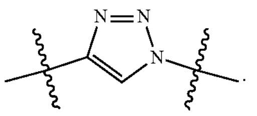 [SMILES: *c1cn(*)nn1]

In some embodiments, a methylene unit of L is replaced with -Cy-. In some embodiments, -Cy- is

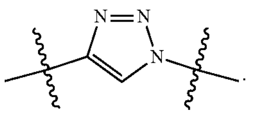 [SMILES: *c1cn(*)nn1]

In some embodiments, a linker moiety, e.g., L, is or comprises —CO)y-. In some embodiments, L is or comprises $-[(CH_2)_nO]_mCy[(CH_2)_nO]_mNH$, or L is $-[(CH_2)_nO]_mCy[(CH_2)_nO]_mNHC(O)[(CH_2)_nO]_mNH-$, or L is $-[(CH_2)_nO]_mCy[(CH_2)_nO]_m\{NHC(O)[(CH_2)_nO]_m\}_pNH-$, where n, m, and p are independently chosen at each occurrence from 1-20, from 1-12, or 2-10. In some embodiments, each n is 2, m is independently chosen at each occurrence from an integer from 2-10, or in some embodiments, m is independently chosen from an integer from 2-6, and Cy is

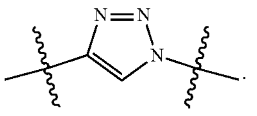 [SMILES: *c1cn(*)nn1]

In some embodiments, a methylene unit of L is replaced with -Cy-. In some embodiments, -Cy- is

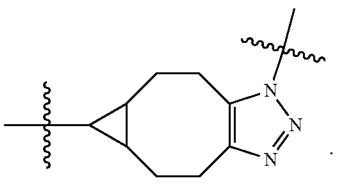 [SMILES: *C1C2CCc3nnn(*)c3CCC12]

In some embodiments, -Cy- is

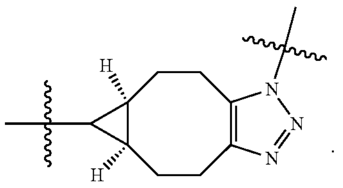 [SMILES: *C1[C@H]2CCc3c(nnn3*)CC[C@@H]12]

In some embodiments, -Cy- is

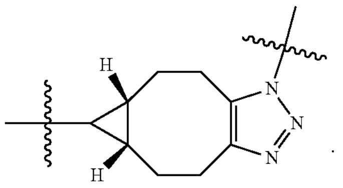 [SMILES: *C1[C@H]2CCc3nnn(*)c3CC[C@@H]12]

In some embodiments, a linker moiety is as described in TABLE 2. In some embodiments, L is $L^1$, as described in this specification. In some embodiments, L is $L^b$, as described in this specification.

In some embodiments, $L^{RM}$ is a covalent bond. In some embodiments, $L^{RM}$ is not a covalent bond. In some embodiments, $L^{RM}$ is or comprises $-(CH_2CH_2O)_n-$. In some embodiments, $L^{RM}$ is or comprises $-(CH_2)_n-O-(CH_2CH_2O)_n-(CH_2)_n-$, wherein each n is independently and each $-CH_2-$ is independently optionally substituted. In some embodiments, $L^{RM}$ is $-(CH_2)_n-O-(CH_2CH_2O)_n-(CH_2)_n-$, wherein each n is independently and each $-CH_2-$ is independently optionally substituted. In some embodiments, $L^{RM}$ is $-(CH_2)_2-O-(CH_2CH_2O)_n-(CH_2)_2-$, wherein n is and each $-CH_2-$ is independently optionally substituted. In some embodiments, $L^{RM}$ is $-(CH_2)_2-O-(CH_2CH_2O)_n-(CH_2)_2-$, wherein n is as described herein.

In some embodiments, $L^{PM}$ is a covalent bond. In some embodiments, $L^{PM}$ is not a covalent bond. In some embodiments, $L^{PM}$ is or comprises $-(CH_2CH_2O)_n-$. In some embodiments, $L^{PM}$ is or comprises $-(CH_2)_n-O-(CH_2CH_2O)_n-(CH_2)_n-$, wherein each n is independently and each $-CH_2-$ is independently optionally substituted. In some embodiments, $L^{PM}$ is $-(CH_2)_n-O-(CH_2CH_2O)_n-(CH_2)_n-$, wherein each n is independently and each $-CH_2-$ is independently optionally substituted. In some embodiments, $L^{PM}$ is $-(CH_2)_2-O-(CH_2CH_2O)_n-(CH_2)_2-$, wherein n is and each $-CH_2-$ is independently optionally substituted. In some embodiments, $L^{PM}$ is $-(CH_2)_2-O-(CH_2CH_2O)_n-(CH_2)_2-$, wherein n is as described herein.

In some embodiments, $L^{PM}$, e.g., in a product of first and second agents, is or comprises a reaction product moiety formed by a first reactive moiety and a second reactive moiety.

In some embodiments, a linker moiety, e.g., $L^{PM}$ in a product of first and second agents, is or comprises

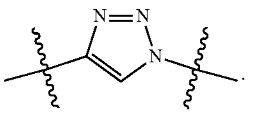 [SMILES: *c1cn(*)nn1]

In some embodiments, a methylene unit of a linker moiety, e.g., L or a linker moiety that can be L, e.g., $L^{RM}$, $L^{PM}$, etc., is replaced with -Cy-. In some embodiments, -Cy- is optionally substituted

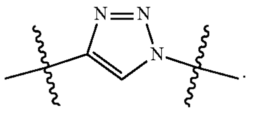 [SMILES: *c1cn(*)nn1]

In some embodiments, -Cy- is

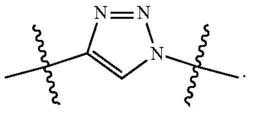 [SMILES: *c1cn(*)nn1]

In some embodiments L is $—[(CH_2)_nO]_mCH_2Cy[(CH_2)_nO]_m—$ or ~~ In embodiments, -Cy- is

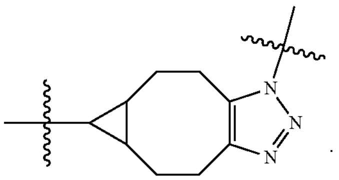 [SMILES: *C1C2CCc3nnn(*)c3CCC12]

In some embodiments, -Cy- is

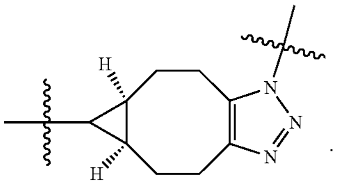 [SMILES: *C1[C@H]2CCc3c(nnn3*)CC[C@@H]12]

In some embodiments, -Cy- is

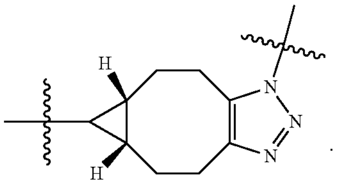 [SMILES: *C1[C@H]2CCc3nnn(*)c3CC[C@@H]12]

Cellular Receptor-Binding Moiety

According to embodiments of the present invention, several receptor-binding moieties are described in WO2019/199621A1, published Oct. 17, 2019, WO2019/199634, published Oct. 17, 2019, International Application No. PCT/US2020/055053 filed Oct. 9, 2020, and International Application No. PCT/US2020/055053 filed Oct. 9, 2020, each of which is incorporated herein in its entirety by reference.

In an embodiment, the cellular receptor-binding moiety may include an asialoglycoprotein receptor (ASGPR) binding group connected through an amine group to the linker moiety.

The amine group may be a primary alkyl amine group or a secondary alkyl amine group, each optionally substituting the amine group with a $C_1$-$C_3$ alkyl group.

The cellular receptor-binding moiety may include an ASGPR binding group according to the chemical structure:

[TBT101]

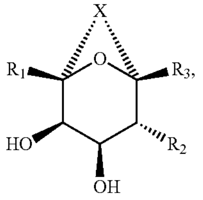

or

[TBT102]

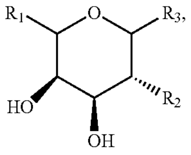

wherein X is 1-4 atoms in length and comprises O, S, $N(R^{N1})$ or $C(R^{N1})(R^{N1})$ groups such that:

when X is 1 atom in length, X is O, S, $N(R^{N1})$ or $C(R^{N1})(R^{N1})$, when X is 2 atoms in length, no more than 1 atom of X is O, S, or $N(R^{N1})$, when X is 3 or 4 atoms in length, no more than 2 atoms of X are O, S, or $N(R^{N1})$;

wherein $R^{N1}$ is H or a $C_1$-$C_3$ alkyl group optionally substituted with from 1-3 halo groups; $R^1$ and $R^3$ are each independently:

H, $—(CH_2)_KOH$, $—(CH_2)_KOC_1$-$C_4$ alkyl, which is optionally substituted with from 1-3 halo groups, $C_1$-$C_4$ alkyl, which is optionally substituted with from 1-3 halo groups, $—(CH_2)_K$-vinyl, O$—(CH_2)_K$-vinyl, $—(CH_2)_K$-alkynyl, $—(CH_2)_K—COOH$, $—(CH_2)_KC(O)O—C_1$-$C_4$ alkyl optionally substituted with from 1-3 halo groups, O—C(O)—$C_1$-$C_4$ alkyl, which is optionally substituted with from 1-3 halo groups, —C(O)—$C_1$-$C_4$ alkyl, which is optionally substituted with from 1-3 halo groups, or $R^1$ and $R^3$ are each independently a

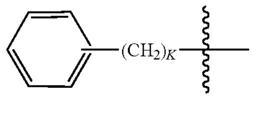

group, which is optionally substituted with up to three halo groups, $C_1$-$C_4$ alkyl groups, each of which alkyl group is optionally substituted with from one to three halo groups or one or two hydroxyl groups, or O—$C_1$-$C_4$ alkyl groups, each of which alkyl groups is optionally substituted with from one to three halo groups or one or two hydroxyl groups; and K is independently an integer of 0 to 4, or $R_1$ and $R_3$ are each independently a group according to the chemical structure:

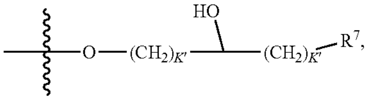
wherein $R^7$ is O—$C_1$-$C_4$ alkyl, which is optionally substituted with from 1 to 3 halo groups 1 or 2 hydroxy groups, or $R^7$ is a —$NR^{N3}R^{N4}$ group or a
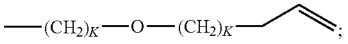
or
$R^1$ and $R_5$ are each independently a group according to the structure:
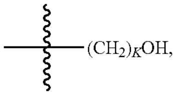
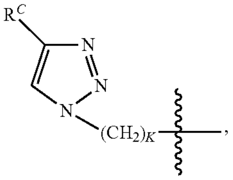
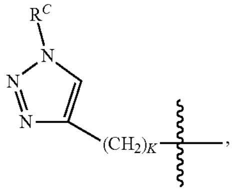
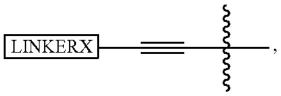
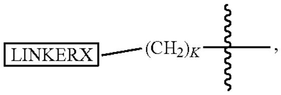
, or a
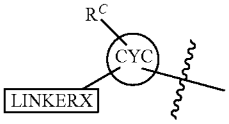
group according to the chemical structure:
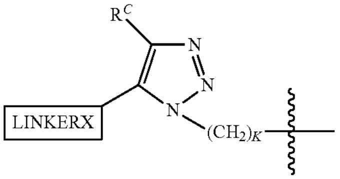
,
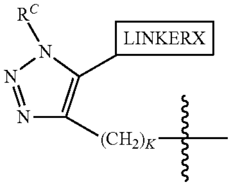
,
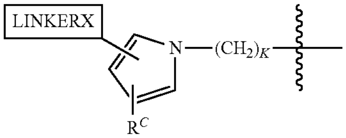
,
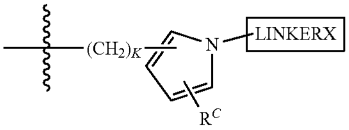
,
-continued
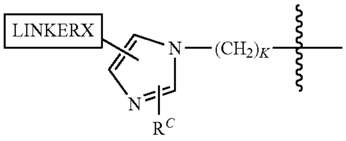
,
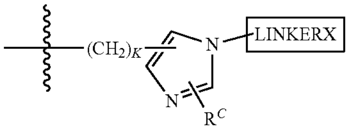
,
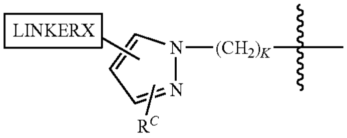
,
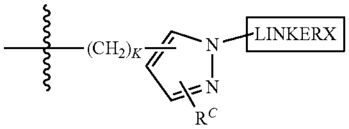
,
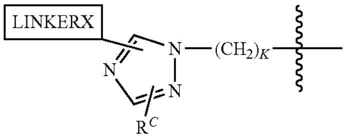
,
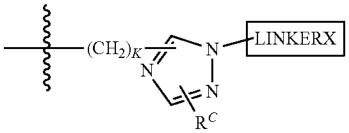
,
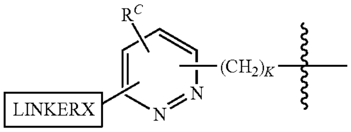
,
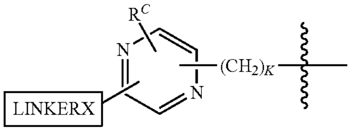
,
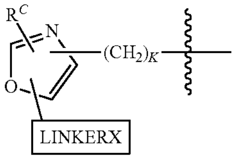
,
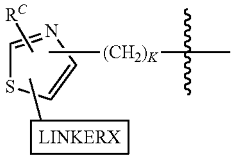
,
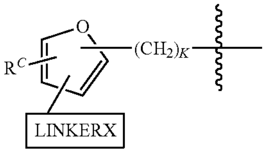
,
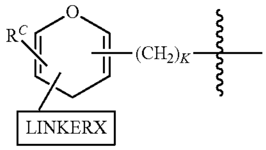
,
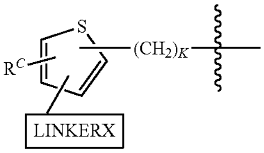
,
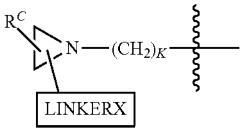
,
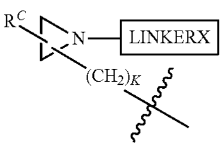
,
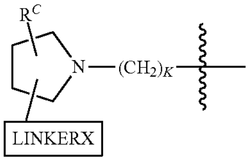
, -continued

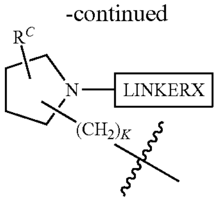,

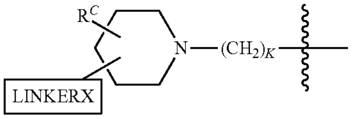,

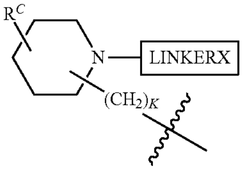, 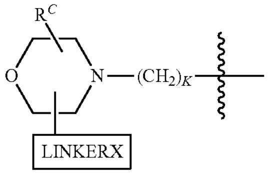,

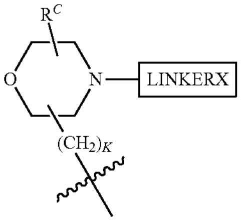, 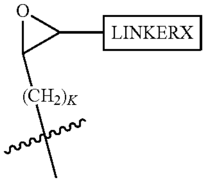,

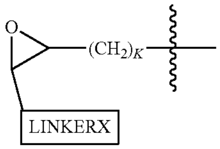, 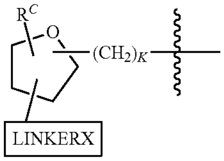,

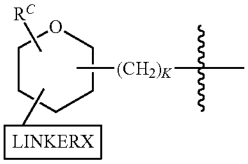, 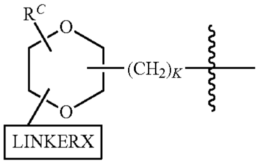,

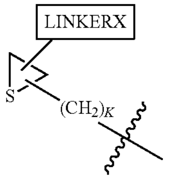, 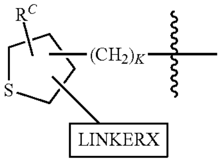, or

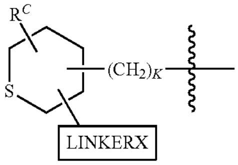, or $R_1$ and $R_3$ are each independently a

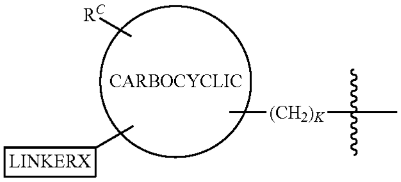

group, where

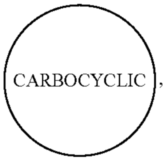, is a $C_3$-$C_8$ saturated carbocyclic group;

$R^C$ is absent, H, $C_1$-$C_4$ alkyl optionally substituted with from 1-3 halo groups or 1-2 hydroxyl groups, or a group according to the structure:

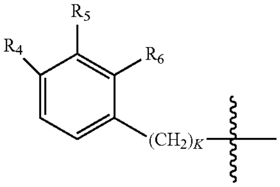

wherein $R_4$, $R_5$, and $R_5$ are each independently, H, halo (F, Cl, Br, I), CN, $NR^{N1}R^{N2}$, $-(CH_2)_KOH$, $-(CH_2)_KOC_1$-$C_4$ alkyl, which is optionally substituted with from 1-3 halo groups, $C_1$-$C_3$ alkyl, which is optionally substituted with from 1-3 halo groups, $-O-C_1$-$C_3$-alkyl, which is optionally substituted with from 1-3 halo groups, $-(CH_2)_KCOOH$, $-(CH_2)_KC(O)O-C_1$-$C_4$ alkyl optionally substituted with from 1-3 halo groups, $O-C(O)-C_1$-$C_4$ alkyl, which is optionally substituted with from 1-3 halo groups, $-C(O)-C_1$-$C_4$ alkyl, which is optionally substituted with from 1-3 halo groups, or $R^C$ is a

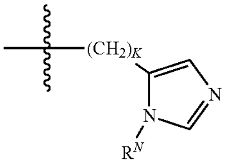

group, a

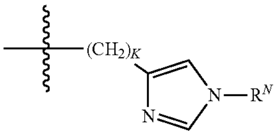

group a

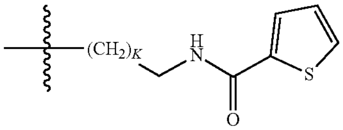

group or a

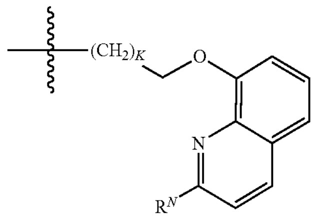

group, wherein $R^N$, $R^{N1}$, and $R^{N2}$ are each independently H or a $C_1$-$C_3$ alkyl group optionally substituted with from one to three halo groups or one or two hydroxyl groups;

K is independently an integer of 0 to 4;

K' is an integer of 1 to 4;

$R^{N3}$ is H, or a $C_1$-$C_3$ alkyl group optionally substituted with 1-3 halo groups or 1 or 2 hydroxy groups; and $R^{N4}$ is H, a $C_1$-$C_3$ alkyl group optionally substituted with 1-3 halo groups or 1 or 2 hydroxy groups, or $R^{N4}$ is a group, where K is preferably 1;

LINKERX is a linker group that comprises at least one galactose-deficient IgA1 binding moiety and links at least one galactose-deficient IgA1 binding moiety to the cellular receptor-binding moiety through the optional linker moiety or LINKERX is a linker group that has at least one or more functional groups that can be used to covalently bond the linker group to at least one galactose-deficient IgA1 binding moiety or optional linker moiety;

$R_2$ is a

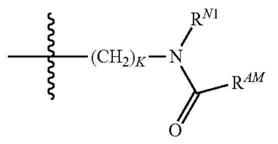

group wherein $R^{N1}$ and K are the same as above;

$R^{AM}$ is H, a $C_1$-$C_4$ alkyl group optionally substituted with up to 3 halo groups and one or two hydroxyl groups, a —$(CH_2)_K$COOH group, a —$(CH_2)_K$C(O)O—$C_1$-$C_4$ alkyl group optionally substituted with from 1-3 halo groups, an O—C(O)—$C_1$-$C_4$ alkyl group, which is optionally substituted with from 1-3 halo F groups, a —C(O)—$C_1$-$C_4$ alkyl group, which is optionally substituted with from 1-3 halo groups, a —$(CH_2)_K$—$NR^{N3}R^{N4}$ group where $R^{N3}$ is H, or a $C_1$-$C_3$ alkyl group optionally substituted with 1-3 halo groups or 1 or 2 hydroxy groups; and $R^{N4}$ is H, a $C_1$-$C_3$ alkyl group optionally substituted with 1-3 halo groups or 1 or 2 hydroxy groups, or a group, or $R_2$ is a

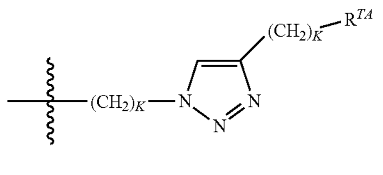

group, wherein $R^{TA}$ is H, CN, $NR^{N1}R^{N2}$, —$(CH_2)_K$OH, —$(CH_2)_K$O$C_1$-$C_4$ alkyl, which is optionally substituted with from 1-3 halo groups, $C_1$-$C_4$ alkyl, which is optionally substituted with from 1-3 halo groups, —$(CH_2)_K$COOH, —$(CH_2)_K$C(O)O—$C_1$-$C_4$ alkyl optionally substituted with from 1-3 halo groups, O—C(O)—$C_1$-$C_4$ alkyl, which is optionally substituted with from 1-3 halo groups, —C(O)—$C_1$-$C_4$ alkyl, which is optionally substituted with from 1-3 halo groups, or $R^{TA}$ is a three-membered to a ten-membered aryl or heteroaryl group containing up to 5 heteroaryl atoms, each of said aryl or heteroaryl groups being optionally substituted with up to three (preferably 1) CN, $NR^{N1}R^{N2}$, —$(CH_2)_K$OH, —$(CH_2)_K$O$C_1$-$C_4$ alkyl, which is optionally substituted with from 1-3 halo groups, $C_1$-$C_3$ alkyl, which is optionally substituted with from 1-3 halo groups or 1 or 2 hydroxy groups, —O—$C_1$-$C_3$-alkyl, which is optionally substituted with from 1-3 halo groups, —$(CH_2)_K$COOH, —$(CH_2)_K$C(O)O—$C_1$-$C_4$ alkyl optionally substituted with from 1-3 halo groups, O—C(O)—$C_1$-$C_4$ alkyl, which is optionally substituted with from 1-3 halo groups or —$(CH_2)_K$C(O)—$C_1$-$C_4$ alkyl optionally substituted with from 1-3 halo groups, or $R^{TA}$ is a

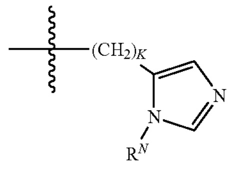

group, a

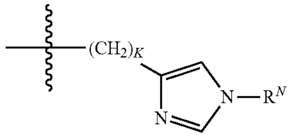

group, a

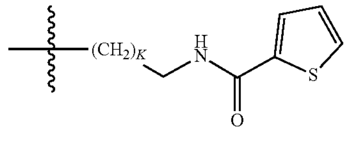

group a

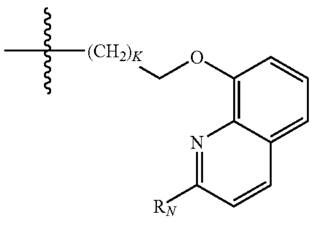

group, a

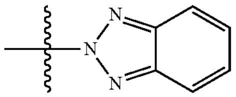 [SMILES: *n1nc2ccccc2n1]

group optionally substituted with up to three $C_1$-$C_3$ alkyl groups, optionally substituted with up to three halo groups, or $R^{TA}$ is a group, wherein $R^N$, $R^{N1}$, and $R^{N2}$ are each independently H or a $C_1$-$C_3$ alkyl group optionally substituted with from one to three halo groups or one or two hydroxyl groups, and each —$(CH_2)_K$ group is optionally substituted with 1-4, preferably 1 or 2, $C_1$-$C_3$ alkyl groups optionally substituted with from 1-3 fluoro groups or 1-2 hydroxyl groups;

and K is independently 0-4.

The cellular receptor-binding moiety may include an ASGPR binding group according to the chemical structure:

[TBT101]

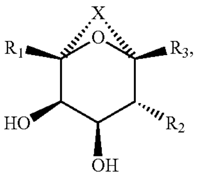

or

[TBT102]

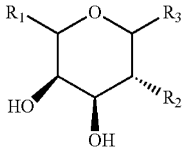

wherein X is 1-4 atoms in length and comprises O, S, $N(R^{N1})$ or $C(R^{N1})(R^{N1})$ groups such that:

when X is 1 atom in length, X is O, S, $N(R^{N1})$ or $C(R^{N1})(R^{N1})$, when X is 2 atoms in length, no more than 1 atom of X is O, S, or $N(R^{N1})$, when X is 3 or 4 atoms in length, no more than 2 atoms of X are O, S, or $N(R^{N1})$;

wherein each $R^{N1}$ is independently H or a $C_1$-$C_3$ alkyl group optionally substituted with from 1-3 halo groups, preferably F ($R^{N1}$ is preferably H or methyl, more often H);

$R_1$ and $R_3$ are each independently H, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$vinyl, O—$(CH_2)_K$vinyl, —$(CH_2)_K$alkynyl, —$(CH_2)_K$COOH, —$(CH_2)_K$C(O)O—$C_1$-$C_4$ alkyl optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R_1$ and $R_3$ are each independently a

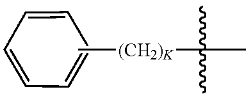

group, which is optionally substituted with up to three (preferably 1) halo groups (preferably F), $C_1$-$C_4$ alkyl groups, each of which is optionally substituted with from one to three halo groups, preferably F, or one or two hydroxyl groups, or O—$C_1$-$C_4$ alkyl groups, each of which alkyl groups is optionally substituted with from one to three halo groups, preferably F, or one or two hydroxyl groups, and K is independently 0-4 (0, 1, 2, 3 or 4), or $R^1$ and $R^3$ are each independently a group according to the chemical structure:

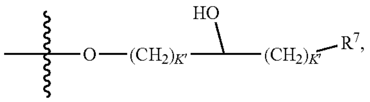

where $R^7$ is O—$C_1$-$C_4$ alkyl, which is optionally substituted with from 1 to 3 halo groups, preferably F and 1 or 2 hydroxy groups, or $R^7$ is a —$NR^{N3}R^{N4}$ group or a

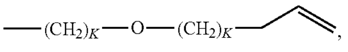

or $R_1$ and $R_3$ are each independently a group according to the structure:

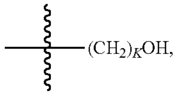

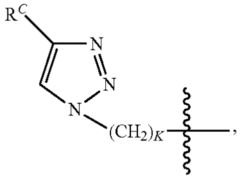

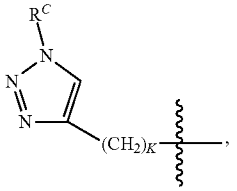

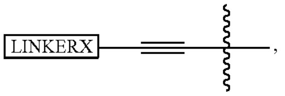

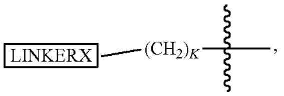

or a

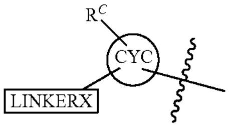

group, according to the chemical structure:
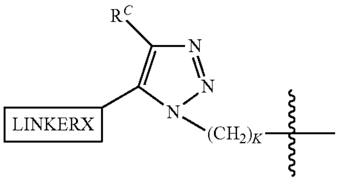,
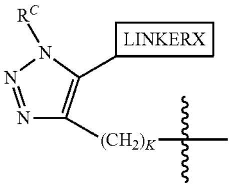,
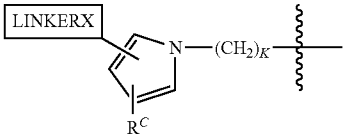,
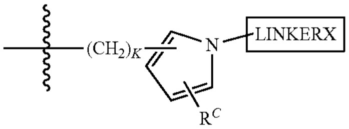,
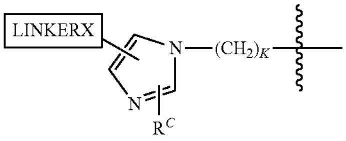,
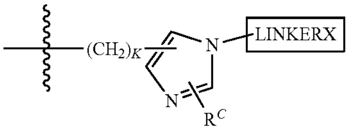,
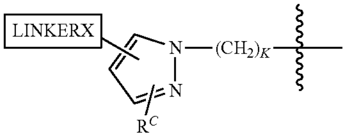,
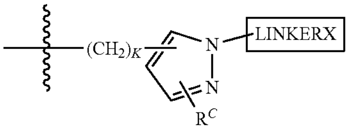,
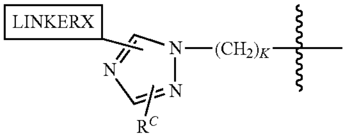,
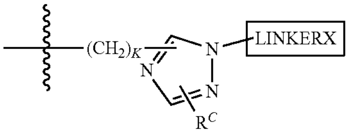,
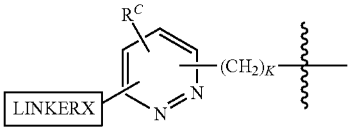,
-continued
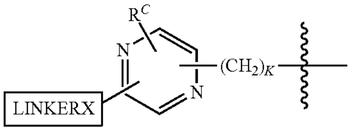,
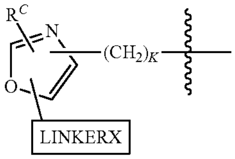, 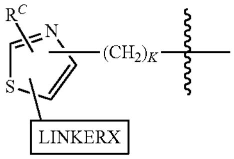,
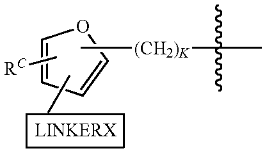, 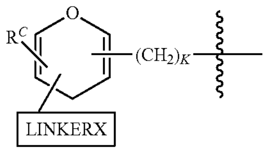,
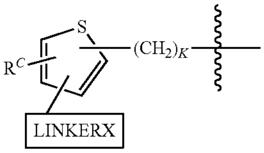, 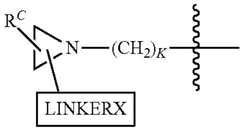,
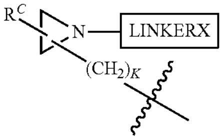, 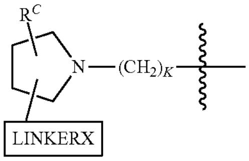,
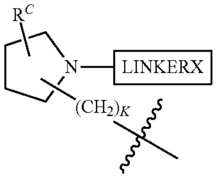,
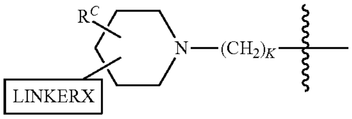,
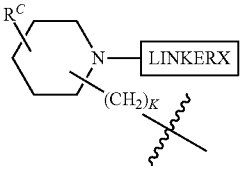, 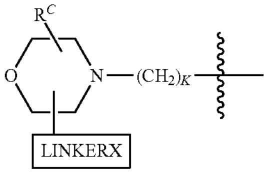,
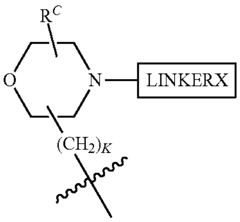, 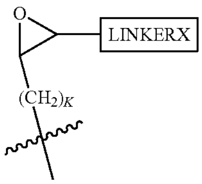,
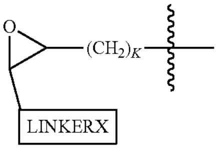, 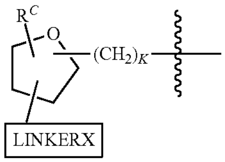, -continued

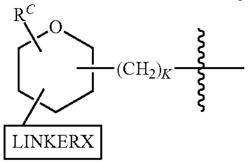

,

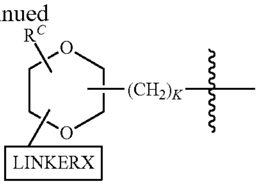

,

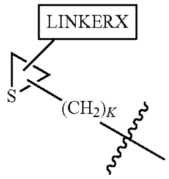

,

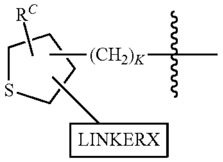

or

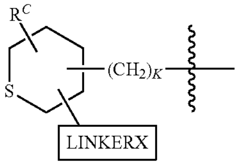

, or $R_1$ and $R_3$ are each independently a

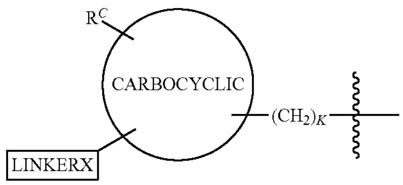

group, where

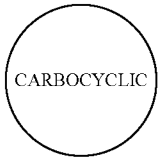

is a $C_3$-$C_8$ saturated carbocyclic group;

$R^C$ is absent, H, $C_1$-$C_4$ alkyl optionally substituted with from 1-3 halo (preferably fluoro) groups or 1-2 hydroxyl groups, or a group according to the structure:

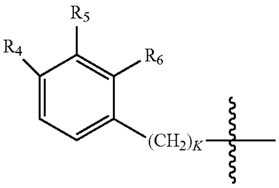

where $R^4$, $R^5$, and $R^6$ are each independently, H, halo (F, Cl, Br, I), CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups, —O—$C_1$-$C_3$-alkyl, which is optionally substituted with from 1-3 halo, preferably F groups, —$(CH_2)_K$COOH, —$(CH_2)_K$C(O)O—$C_1$-$C_4$ alkyl optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^C$ is a

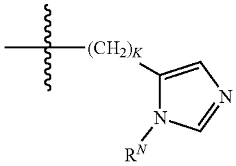

group, a

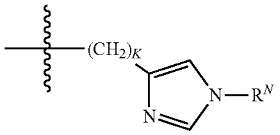

group a

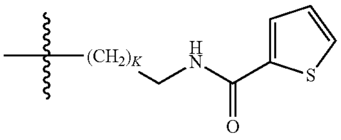

group, or a

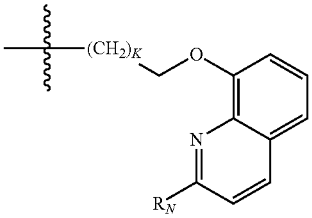

group, where $R^N$, $R^{N1}$, and $R^{N2}$ are each independently H or a $C_1$-$C_3$ alkyl group optionally substituted with from one to three halo groups, preferably F, or one or two hydroxyl groups;

K is independently 0-4 (0, 1, 2, 3, or 4), preferably 0 or 1;

K' is 1-4, preferably 1;

$R^{N3}$ is H, or a $C_1$-$C_3$ alkyl group optionally substituted with 1-3 halo groups, preferably F or 1 or 2 hydroxy groups; and $R^{N4}$ is H, a $C_1$-$C_3$ alkyl group optionally substituted with 1-3 halo groups, preferably F or 1 or 2 hydroxy groups, or $R^{N4}$ is a group, where K is preferably 1;

LINKERX is a linker group that comprises at least one galactose-deficient IgA1 binding moiety and links at least one galactose-deficient IgA1 binding moiety to the cellular receptor-binding moiety through the optional linker moiety or LINKERX is a linker group that has at least one or more functional groups that can be used to covalently bond the linker group to at least one galactose-deficient IgA1 binding moiety or optional linker moiety;

$R_2$ is a

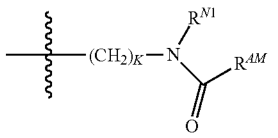

group where $R^{N1}$ and K are the same as above;

$R^{AM}$ is H, a $C_1$-$C_4$ alkyl group optionally substituted with up to 3 halo groups (preferably F) and one or two hydroxyl groups, a $—(CH_2)_K COOH$ group, a $—(CH_2)_K C(O)O—C_1$-$C_4$ alkyl group optionally substituted with from 1-3 halo, preferably F groups, O—C(O)—$C_1$-$C_4$ alkyl group, which is optionally substituted with from 1-3 halo, preferably F groups, a —C(O)—$C_1$-$C_4$ alkyl group, which is optionally substituted with from 1-3 halo, preferably F groups, a $—(CH_2)_K—NR^{N3}R^{N4}$ group where $R^{N3}$ is H, or a $C_1$-$C_3$ alkyl group optionally substituted with 1-3 halo groups, preferably F or 1 or 2 hydroxy groups, or $R_2$ is a

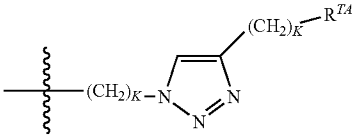

group, wherein $R^{TA}$ is H, CN, $NR^{N1}R^{N2}$, $—(CH_2)_K OH$, $—(CH_2)_K OC_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, $—(CH_2)_K COOH$, $—(CH_2)_K C(O)O—C_1$-$C_4$ alkyl optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^{TA}$ is a C3-C10 aryl or a three-membered to ten-membered heteroaryl group containing up to 5 heteroaryl atoms, each of said aryl or heteroaryl groups being optionally substituted with up to three (preferably 1) CN, $NR^{N1}R^{N2}$, $—(CH_2)_K OH$, $—(CH_2)_K OC_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups or 1 or 2 hydroxy groups, —O—$C_1$-$C_3$-alkyl, which is optionally substituted with from 1-3 halo, preferably F groups, $—(CH_2)_K COOH$, $—(CH_2)_K C(O)O—C_1$-$C_4$ alkyl optionally substituted with from 1-3 halo, preferably F groups, O—C(O)—$C_1$-$C_4$ alkyl, which is optionally substituted with from 1-3 halo, preferably F groups or $—(CH_2)_K C(O)—C_1$-$C_4$ alkyl optionally substituted with from 1-3 halo, preferably F groups, or $R^{TA}$ is a

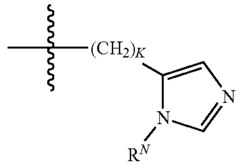

group, a

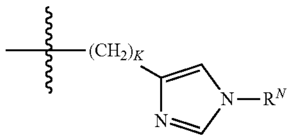

group, a

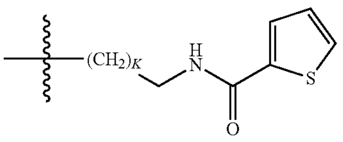

group or a

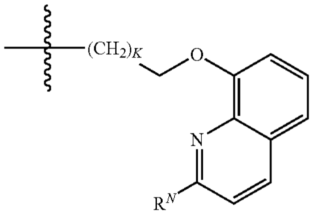

group, or $R^{TA}$ is a

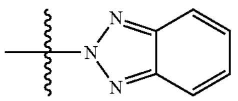 [SMILES: *n1nc2ccccc2n1]

group that is optionally substituted with up to three, preferably 1 $C_1$-$C_3$ alkyl groups optionally substituted with up to three halo (preferably F) groups or $R^{TA}$ is a

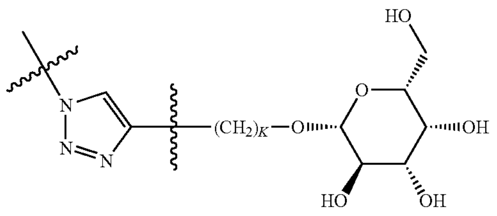

group, wherein $R^N$, $R^{N1}$, and $R^{N2}$ are each independently H or a $C_1$-$C_3$ alkyl group optionally substituted with from one to three halo groups, preferably F, or one or two hydroxyl groups and wherein each —$(CH_2)_K$ group is optionally substituted with 1-4, preferably 1 or 2, $C_1$-$C_3$ alkyl groups optionally substituted with from 1-3 fluoro groups or 1-2 hydroxyl groups;

and K is independently 0-4 (0, 1, 2, 3, or 4), preferably 0 or 1, or a pharmaceutically acceptable salt, stereoisomer, solvate, or polymorph thereof.

In an embodiment,

X is —O—C($R^{N1}$)($R^{N1}$), C($R^{N1}$)($R^{N1}$)—O—, —S—C($R^{N1}$)($R^{N1}$), C($R^{N1}$)($R^{N1}$)—S—, N($R^{N1}$)—C($R^{N1}$)($R^{N1}$), C($R^{N1}$)($R^{N1}$)—N($R^{N1}$) or C($R^{N1}$)($R^{N1}$)—C($R^{N1}$)($R^{N1}$) when X is 2 atoms in length, X is —O—C($R^{N1}$)($R^{N1}$)—C($R^{N1}$)($R^{N1}$), C($R^{N1}$)($R^{N1}$)—O—C($R^{N1}$)($R^{N1}$)—, —O—C($R^{N1}$)($R^{N1}$)—O—, —O—C($R^{N1}$)($R^{N1}$)—S—, —O—C($R^{N1}$)($R^{N1}$)—N($R^{N1}$)—, —S—C($R^{N1}$)($R^{N1}$)—C($R^{N1}$)($R^{N1}$), C($R^{N1}$)($R^{N1}$)—S—C($R^{N1}$)($R^{N1}$)—, C($R^{N1}$)($R^{N1}$)—C($R^{N1}$)($R^{N1}$)—S, —S—C($R^{N1}$)($R^{N1}$)—S—, —S—C($R^{N1}$)($R^{N1}$)—O—, —S—C($R^{N1}$)($R^{N1}$)—N($R^{N1}$)—, N($R^{N1}$)—C($R^{N1}$)($R^{N1}$)—C($R^{N1}$)($R^{N1}$), C($R^{N1}$)($R^{N1}$)—N($R^{N1}$)—C($R^{N1}$)($R^{N1}$), ($R^{N1}$)($R^{N1}$)—C($R^{N1}$)($R^{N1}$)—N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)—C($R^{N1}$)($R^{N1}$) when X is 3 atoms in length, and ($R^{N1}$)—N($R^{N1}$)—C($R^{N1}$)($R^{N1}$)—C($R^{N1}$)($R^{N1}$), C($R^{N1}$)($R^{N1}$)—C($R^{N1}$)($R^{N1}$)—N($R^{N1}$), N($R^{N1}$)—C($R^{N1}$)($R^{N1}$)—N($R^{N1}$), or C($R^{N1}$)($R^{N1}$)—C($R^{N1}$)($R^{N1}$)—C($R^{N1}$)($R^{N1}$) when X is 4 atoms in length, wherein $R^{N1}$ is the same as stated above.

In an embodiment, X is $OCH_2$ or $CH_2O$, and $R^{N1}$ is H.

The cellular receptor-binding moiety may include an ASGPR binding group according to the chemical structure:

[TBT101]

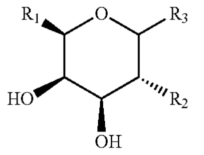

or

[TBT102]

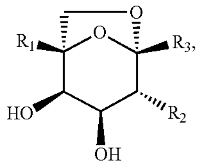

where $R_1$, $R_2$, *and R3 are the* or a pharmaceutically acceptable salt, stereoisomer, solvate, or polymorph thereof.

The cellular receptor-binding moiety may have the following structure:

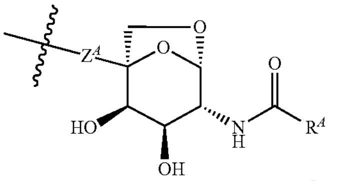

or

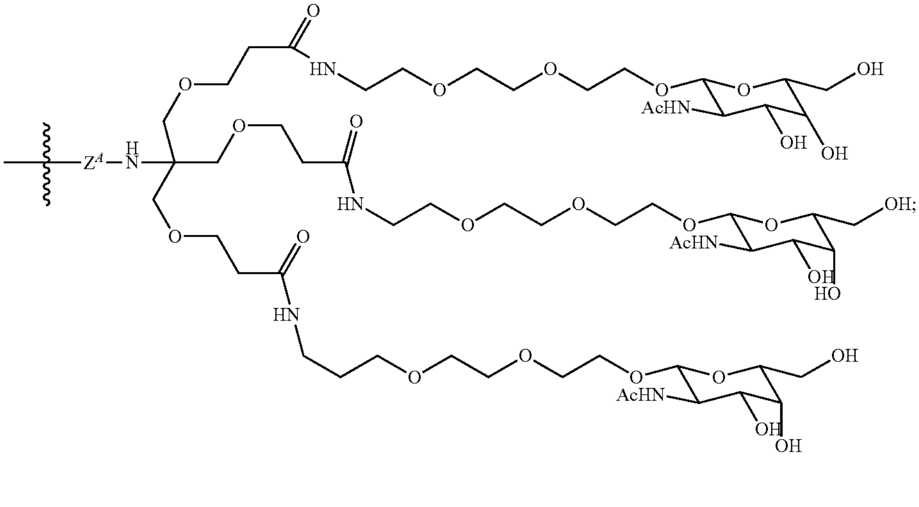

X is —O—C($R^{N1}$)($R^{N1}$)—C($R^{N1}$)($R^{N1}$)—C($R^{N1}$)($R^{N1}$), C($R^{N1}$)($R^{N1}$)—O—C($R^{N1}$)($R^{N1}$)—($R^{N1}$)($R^{N1}$)—, —O—C($R^{N1}$)($R^{N1}$). O—C($R^{N1}$)($R^{N1}$)—, —S—C($R^{N1}$)($R^{N1}$)—C($R^{N1}$)($R^{N1}$)—C($R^{N1}$)($R^{N1}$)—, C($R^{N1}$)($R^{N1}$)—S—C($R^{N1}$)($R^{N1}$)—C($R^{N1}$)($R^{N1}$)—, C($R^{N1}$)($R^{N1}$)—($R^{N1}$)($R^{N1}$)—S—C($R^{N1}$)($R^{N1}$)—, —S—C($R^{N1}$)($R^{N1}$)—S—C($R^{N1}$)($R^{N1}$)—, N($R^{N1}$)—C($R^{N1}$)($R^{N1}$)—C($R^{N1}$)($R^{N1}$)—C($R^{N1}$)($R^{N1}$)—, C($R^{N1}$)

where $R^A$ is a $C_1$-$C_3$ alkyl group optionally substituted with 1-5 halo (preferably fluoro) groups (preferably $R^A$ is a methyl or ethyl group optionally substituted with from 1-3 fluoro groups);

$Z_A$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8 preferably 1-4 ethylene glycol residues or a —$C(O)(CH_2)_{IM}N_{RM}$ group (preferably a PEG containing group comprising from 1 to 8 ethylene glycol, preferably 2-4 ethylene glycol residues) where IM and $R_M$ are the same as above; and $Z_B$ is absent, $(CH_2)_{IM}$, C(O)—$(CH_2)_{IM}$—$N_{RM}$, or C(O)—$(CH_2)_{IM}$—$NR_M$, where IM and $R_M$ are the same as above.

In an embodiment, $R^A$ may be a methyl or ethyl group optionally substituted with from 1-3 fluoro groups.

In an embodiment, $Z_A$ may be a PEG group containing from 1 to 4 ethylene glycol residues.

In an embodiment, the methyl or ethyl group may be substituted with from 1-3 fluoro groups.

In an embodiment, the ASGPR binding group may be N-acetyl-D-galactosamine.

In an embodiment, the cellular receptor-binding moiety may be a low-density lipoprotein receptor-related protein 1 (LRP1), a low-density lipoprotein receptor (LDLR), a FcγRI binding group, a FcRN binding group, a transferrin receptor-binding group, or a macrophage scavenger receptor-binding group.

Pharmaceutically Acceptable Excipients.

Formulations suitable for parenteral administration, such as by intraarticular (in the joints), intravenous, intramuscular, intratumoral, intradermal, intraperitoneal, and subcutaneous routes, include aqueous and non-aqueous, isotonic sterile injection solutions, which can have antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered by intravenous infusion, orally, topically, intraperitoneally, intravesically, or intrathecally. Parenteral, oral, and administration are preferred administration methods. The formulations of compounds can be presented in unit-dose or multi-dose sealed containers, such as ampules and vials.

Solutions or suspensions used for parenteral, intradermal, or subcutaneous application can include these components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the change in tonicity such as sodium chloride or dextrose. The pH can be adjusted with acids or bases, such as hydrochloric acid or sodium hydroxide. The parenteral preparation can be enclosed in ampoules, disposable syringes, or multiple dose vials made of glass or plastic.

EXAMPLES

The invention is further illustrated by non-limited EXAMPLES.

Example 1

Antibody-Drug Conjugates

Figure 1:
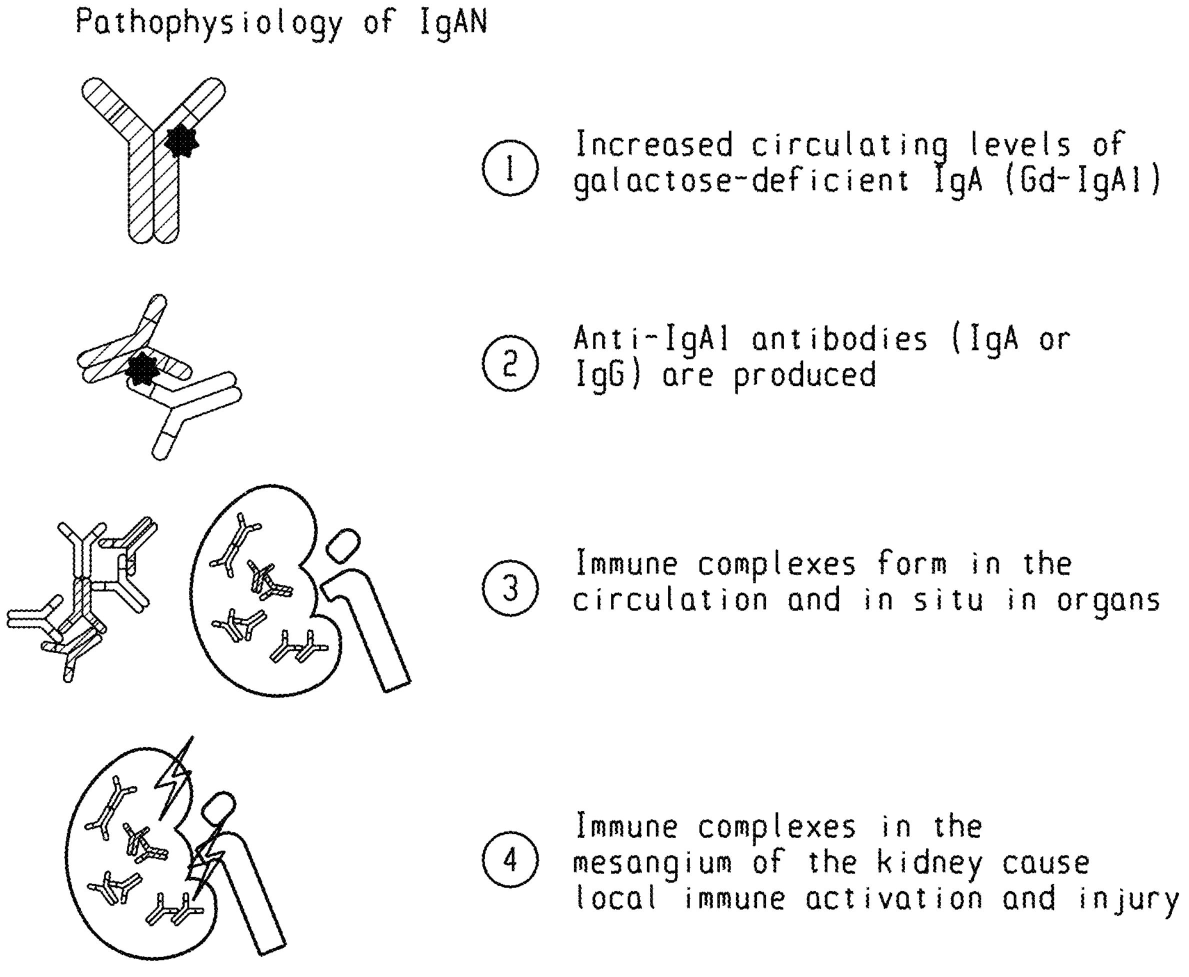
FIG. 1 is a list showing how Gd-IgA1 degradation is used to treat IgA nephropathy (IgAN).
Figure 2:
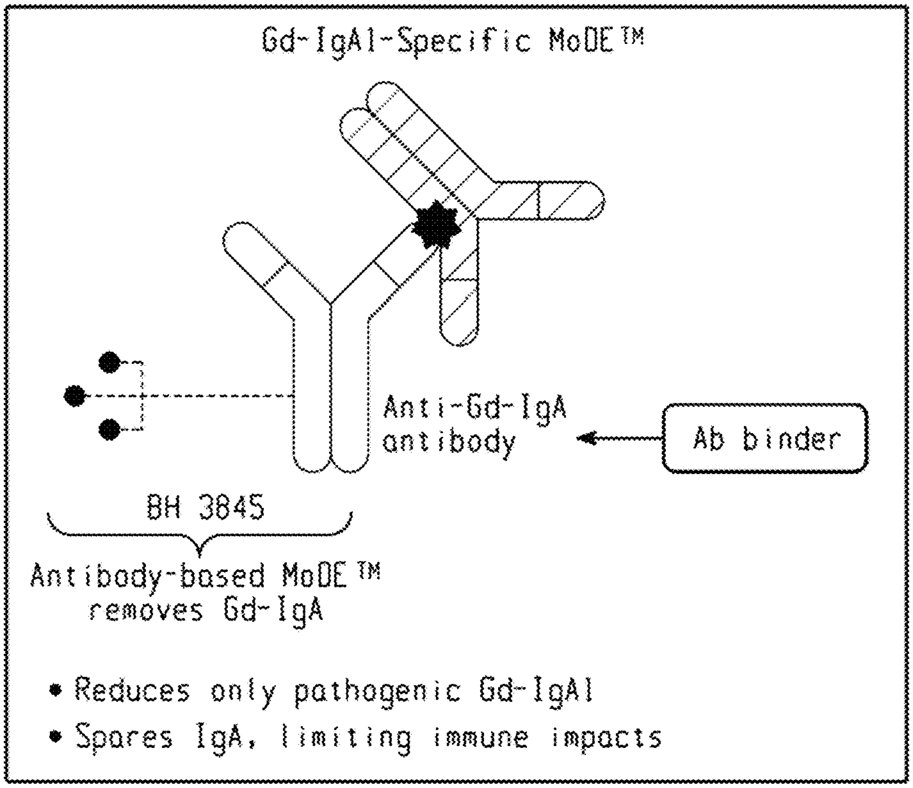
FIG. 2 is a diagram schematically illustrating removal of Gd-IgA1 by a Gd-IgA1 specific MODE™.
Figure 3:
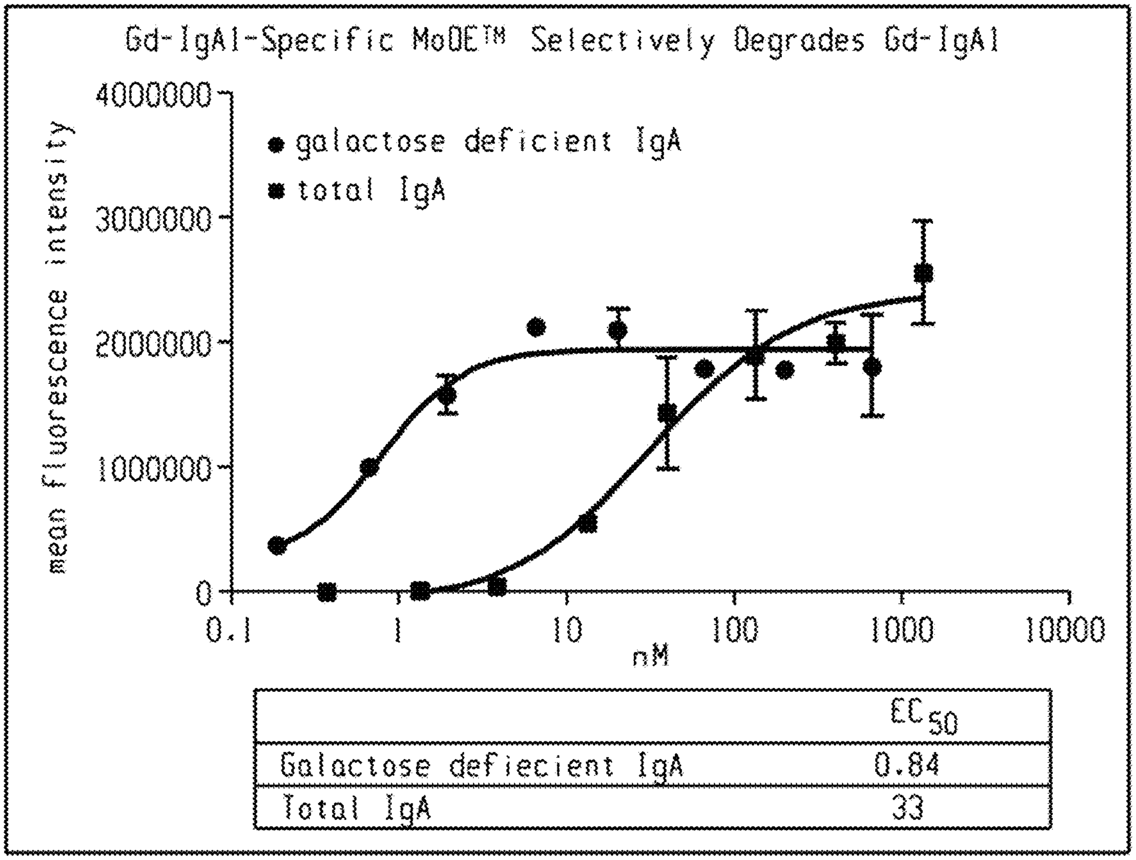
FIG. 3 is a graph of mean fluorescent intensity (arbitrary units) vs. concentration (nanomolar, nm) preclinical study results, where an embodiment of the invention (Gd-IgA-Specific MoDE™) at low concentrations selectively degrades the Gd-IgA 1 present in IgA nephropathy (IgAN) and spares total IgA, limiting the impact on the immune system.
Figure 4:
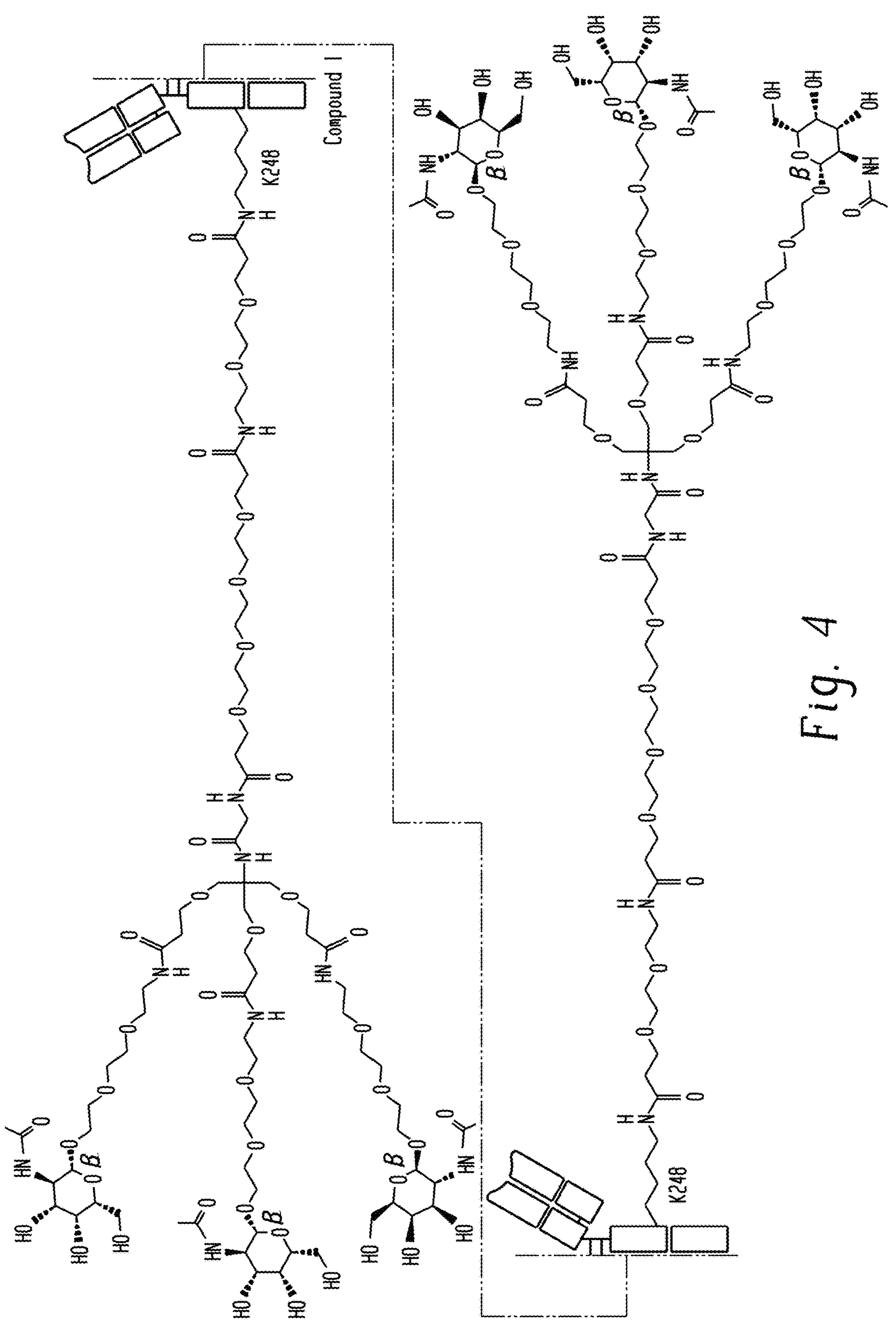
FIG. 4 illustrates a chimeric Km55 antibody according to an embodiment of the present invention.
Figure 5:
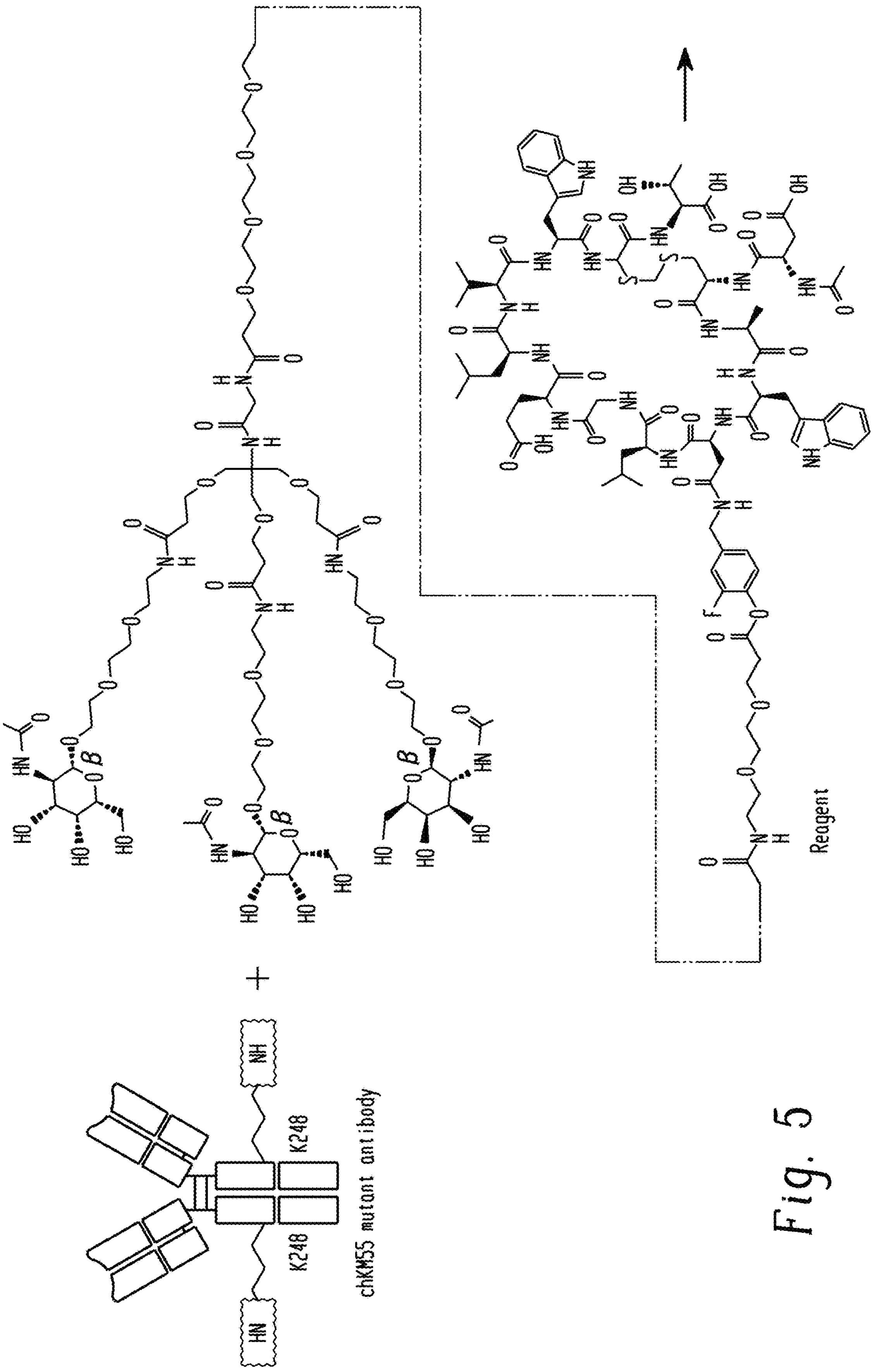
FIG. 5 and FIG. 6 reproduce a reaction scheme showing a process for preparing one embodiment of the bifunctional molecules (agents) from a chimeric Km55 antibody and a reagent having affinity for the chimeric Km55 antibody by conjugating the chimeric Km55 antibody to the reagent.
Figure 6:
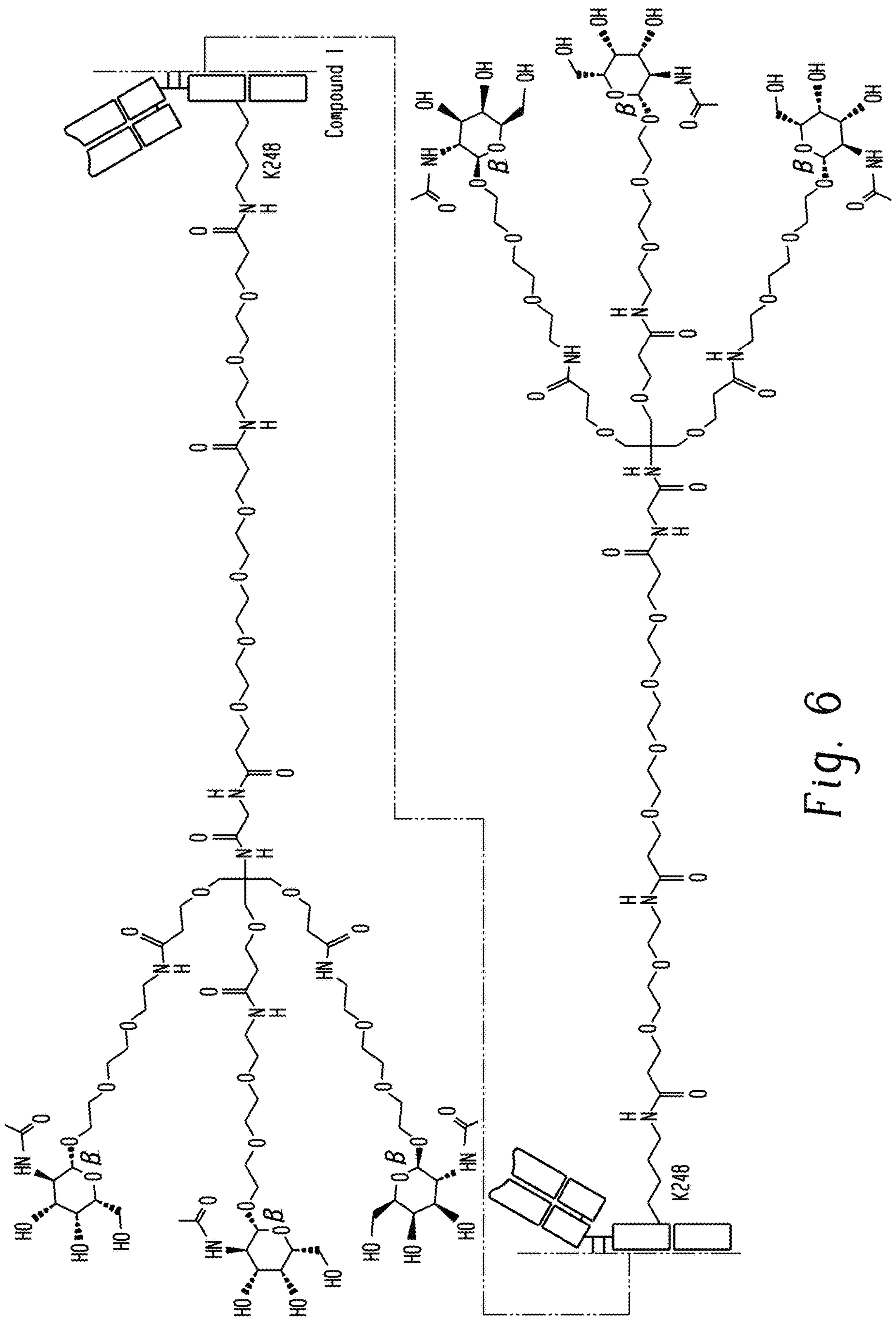

In one embodiment, the antibody-drug conjugate may have a structure represented in FIG. 4, which illustrates a process of preparation of the antibody-drug conjugate from a chimeric Km55 antibody and a reagent having affinity to the chimeric Km55 antibody by conjugating the chimeric Km55 antibody to the reagent.

In one embodiment, ABT010 is an antibody in which the galactose-deficient IgA1 binding moiety has a heavy chain polypeptide sequence of SEQ ID NO: 1 (HC010) and a light chain polypeptide sequence of SEQ ID NO: 2 (LC010).

In another embodiment, the chimeric Km55 antibody may include amino acid mutations (chimeric mutant Km55 antibody). In an example, the chimeric mutant Km55 antibody (ABT020) may include a sequence wherein the galactose-deficient IgA1 binding moiety has a heavy chain polypeptide sequence of SEQ ID NO: 3 (HC020) and light chain polypeptide sequence SEQ ID NO: 2 (LC010).

In another example, the chimeric mutant Km55 antibody (ABT030) may include a sequence wherein the galactose-deficient IgA1 binding moiety has a heavy chain polypeptide sequence of SEQ ID NO: 4 (HC030) and light chain polypeptide sequence SEQ ID NO: 2 (LC010).

In another example, the chimeric mutant Km55 antibody (ABT040) may include a sequence wherein the galactose-deficient IgA1 binding moiety has a heavy chain polypeptide sequence of SEQ ID NO: 5 (HC040) and light chain polypeptide sequence SEQ ID NO: 2 (LC010).

In another example, the chimeric mutant Km55 antibody (ABT050) may include a sequence in which the galactose-deficient IgA1 binding moiety has a heavy chain polypeptide sequence of SEQ ID NO: 6 (HC050) and a light chain polypeptide sequence of SEQ ID NO: 2 (LC010).

In another example, the chimeric mutant Km55 antibody (ABT060) may include a sequence in which the galactose-deficient IgA1 binding moiety has a heavy chain polypeptide sequence of SEQ ID NO: 7 (HC060) and a light chain polypeptide sequence of SEQ ID NO: 2 (LC010).

In another example, the chimeric mutant Km55 antibody (ABT070) may include a sequence in which the galactose-deficient IgA1 binding moiety has a heavy chain polypeptide sequence of SEQ ID NO: 8 and a light chain polypeptide sequence of SEQ ID NO: 2 (LC010).

Specific Mutation Strategies to Reduce FcγR and c1q Binding and Effector Function and Enhance FcRn Binding/Exposure of Antibodies.

Fc Mutation Strategies to Reduce FcγR and c1q Binding.

The inventors mutated Km55 to insert a LALA mutation using biomedical-art recognized methods first described by the Winter group in the 1990s. In this EXAMPLE, LALA=L234A/L235A.

The inventors mutated Km55 to insert a LALA mutation using biomedical-art recognized methods first described by the Winter group in the 1990s, then inserted P mutations, such as by the biomedical-art recognized methods introduced by the Roche team in 2016, such as the technology for adding P329G and P329G combined with LALA: In this EXAMPLE, LALA/PA=L234A/L235A/P329A. LALA/PG=L234A/L235A/P329G. See Tilman, Schlothauer and others, Protein Engineering, Design and Selection, Volume 29, Issue 10, October 2016, Pages 457-466. This paper shows that even LALA itself abolishes c1q binding. P329A alone was tested. P329A abolishes c1q binding and reduces FcgR binding. They do not test P329A/LALA but show that P329G/LALA further reduces FcgR binding beyond LALA alone.

TABLE 4

| Antibody sequences | | | |
|---|---|---|---|
| Antibody | Sequence Identity | Heavy chain | |
| ABT010 | Unmutated | HC010 | SEQ ID NO: 1 |
| ABT020 | chimeric LALA mutant | HC020 | SEQ ID NO: 3 |
| ABT030 | chimeric LALA PA mutant | HC030 | SEQ ID NO: 4 |

The inventors also mutated Km55 in other regions. N297A/Q removes the natural N-linked glycosylation site in the hinge region.

Fc Mutation Strategies to Enhance FcRn Binding to Prolong Exposure.

Figure 7:
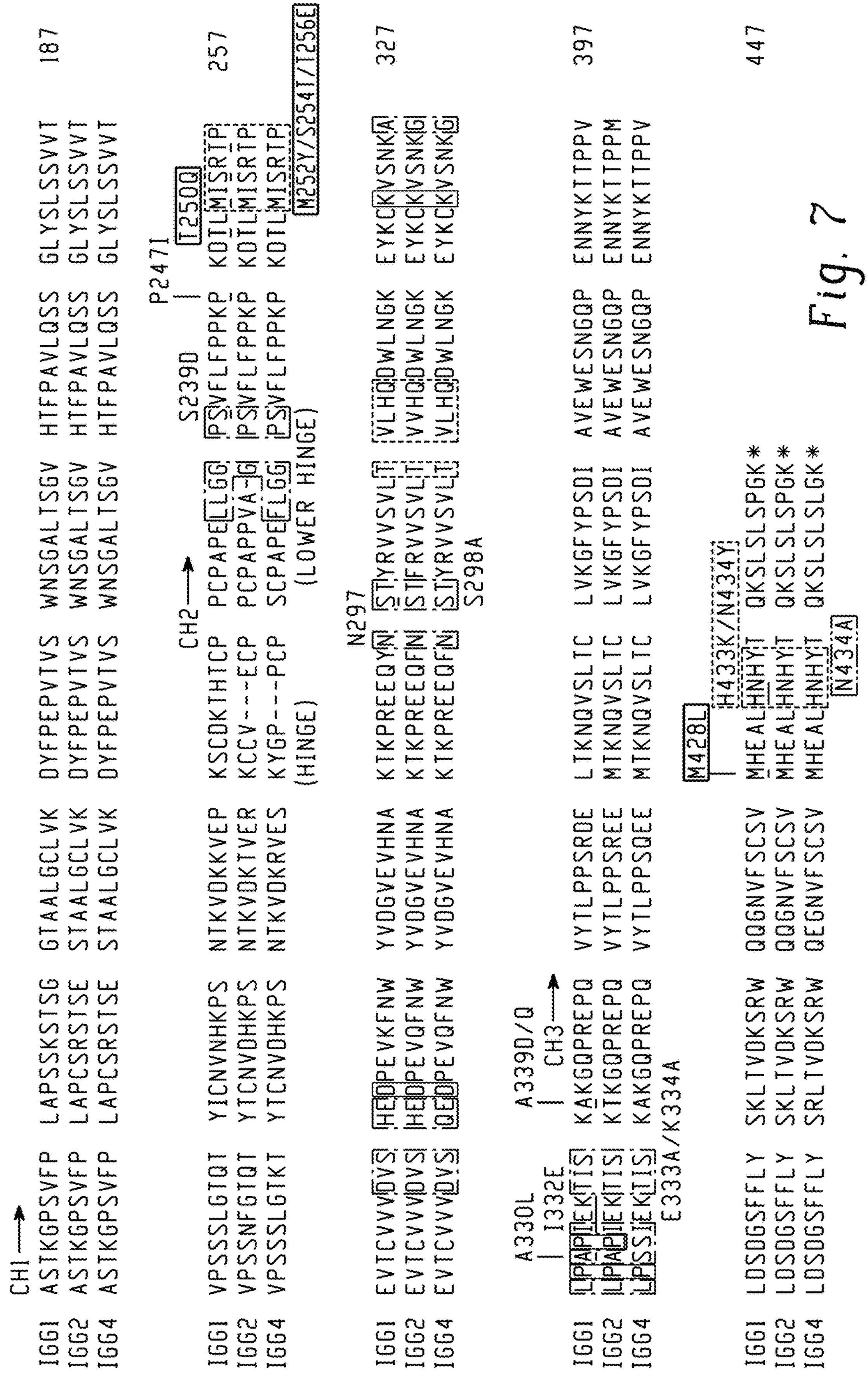
FIG. 7 is a comparison of sequences of the constant heavy chains of human IgG1 (SEQ ID NO: 16), IgG2 (SEQ ID NO: 17), and IgG4 (SEQ ID NO: 18), which form the basis of human and humanized therapeutic antibodies. Sequence differences in IgG2 and IgG4 from IgG1 are noted. The hinge and lower hinge regions, with the N-glycosylation site, N297, are noted. Numbering is according to the EU numbering scheme. Sequences important for FcgR binding, C1q, and FcRn are noted by shading. Some increased ADCC mutants are shown above or below the sequences, as noted: Xencor's S239D, A330L, I332E [red, above sequences]; Genentech's S298A, E333A, K334A [blue, below sequences]; and Eli Lilly/AME's P247I, A339D/Q [green, above sequences]. Examples of FcRn-binding mutants for prolongation of half-life are also shown, as noted: MedImmune's YTE mutant (M252Y, S254T, T256E), PDL's T250Q, M428L mutant, Sally Ward's H433K mutant, N434Y mutant, and Genentech's N434A mutant are shown in red, orange, green, and blue boxes, respectively.
Figure 8:
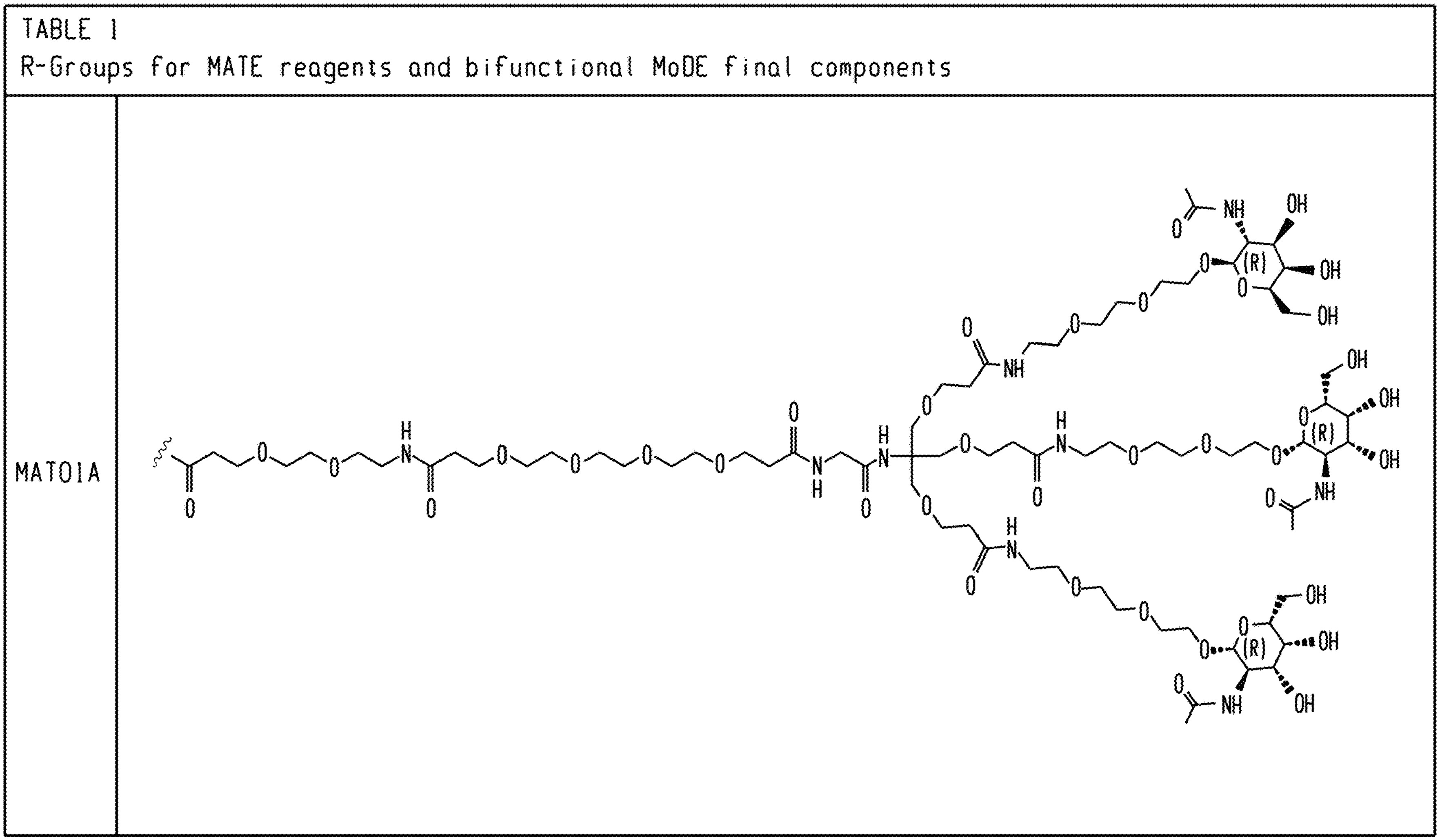
FIG. 8 to FIG. 14 illustrate a table (TABLE 1) of R-groups for MATE reagents and bifunctional MoDE final compounds.
Figure 9:
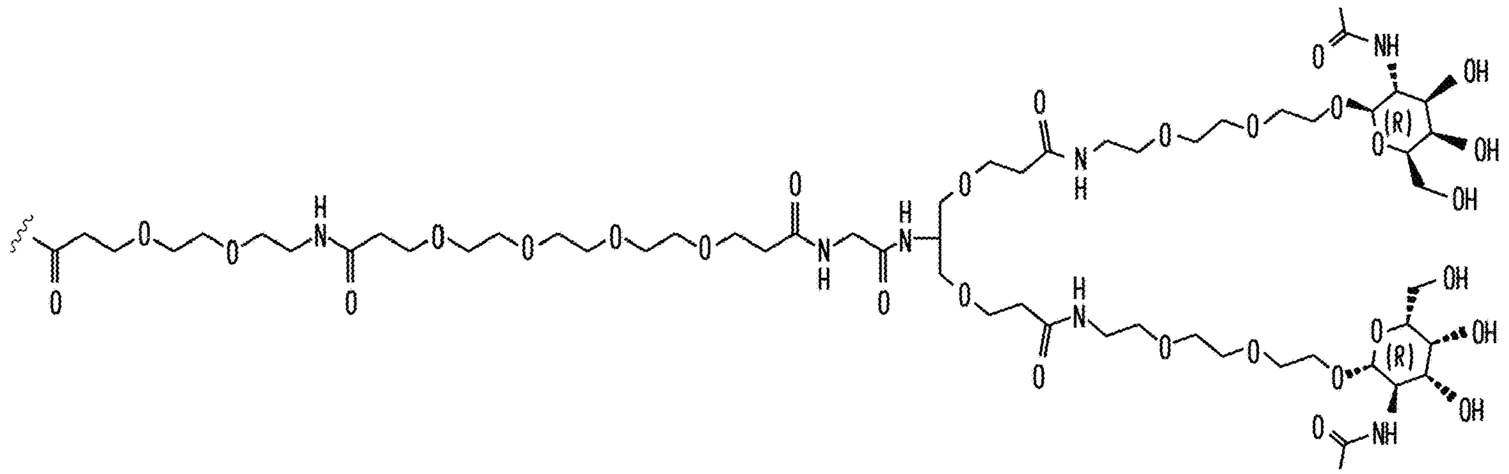
Figure 10:
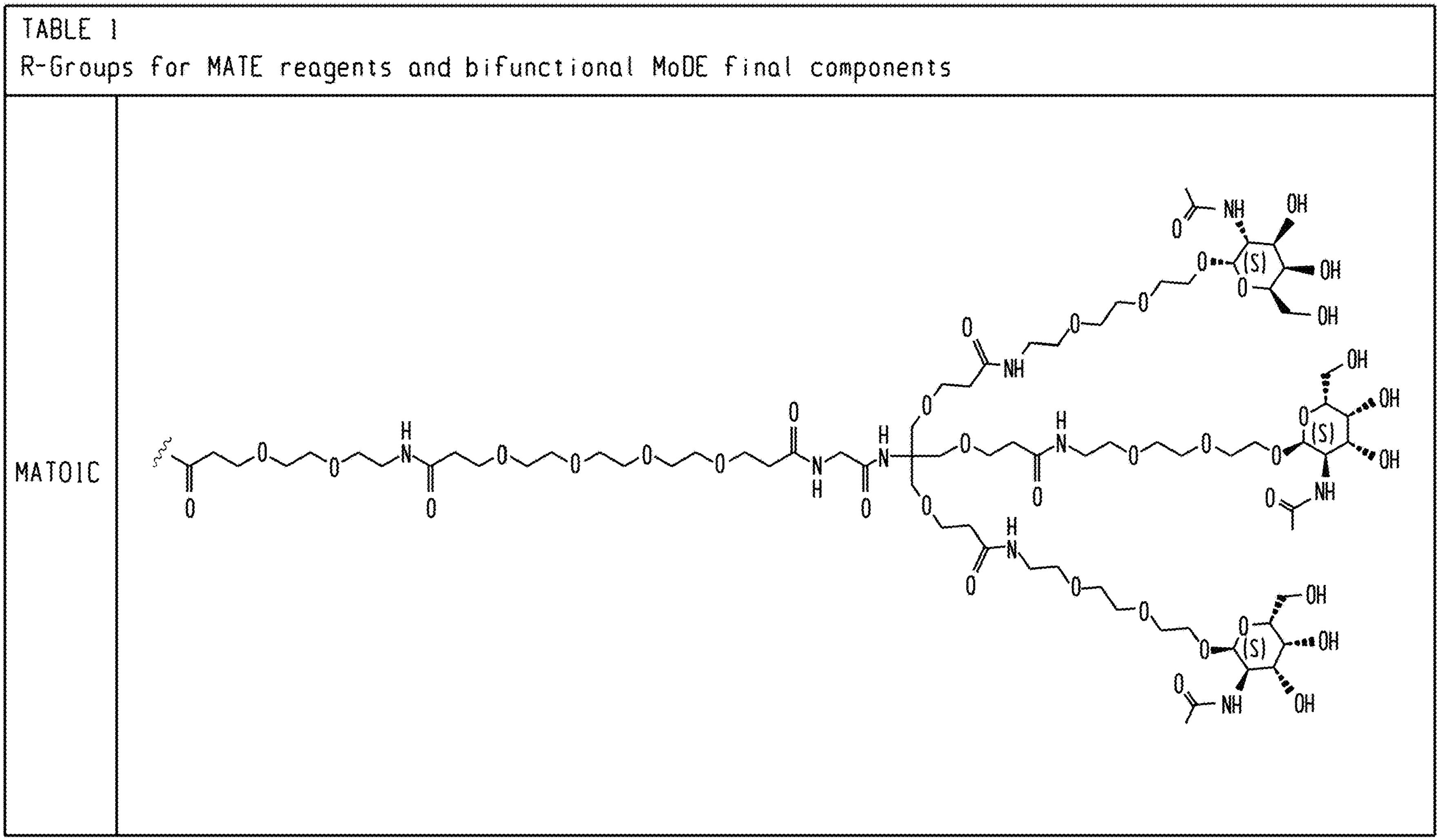
Figure 11:
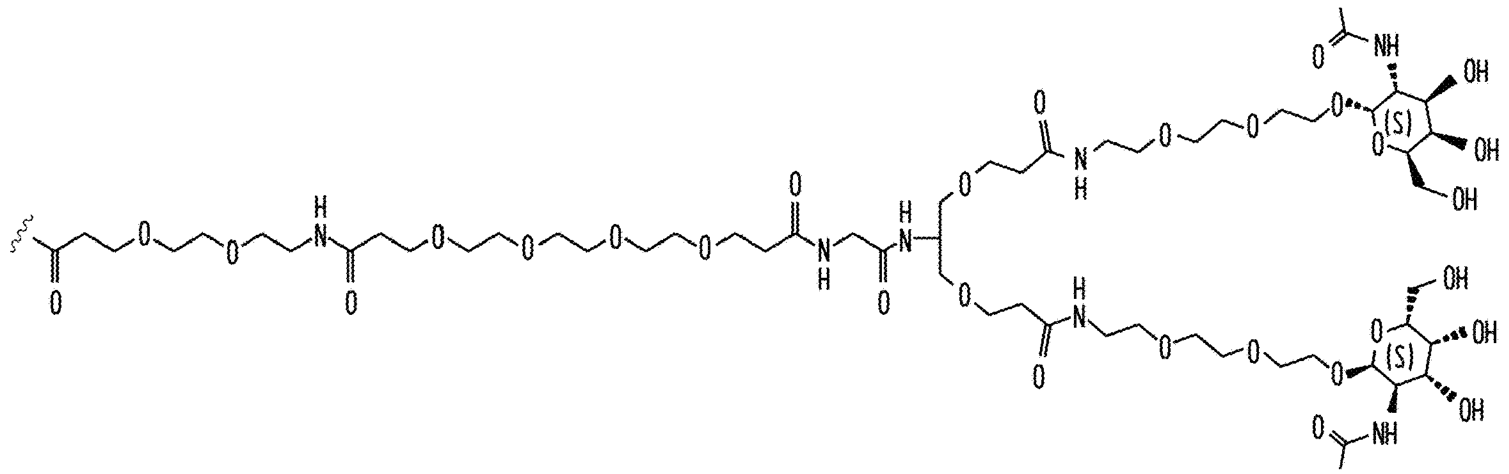
Figure 12:
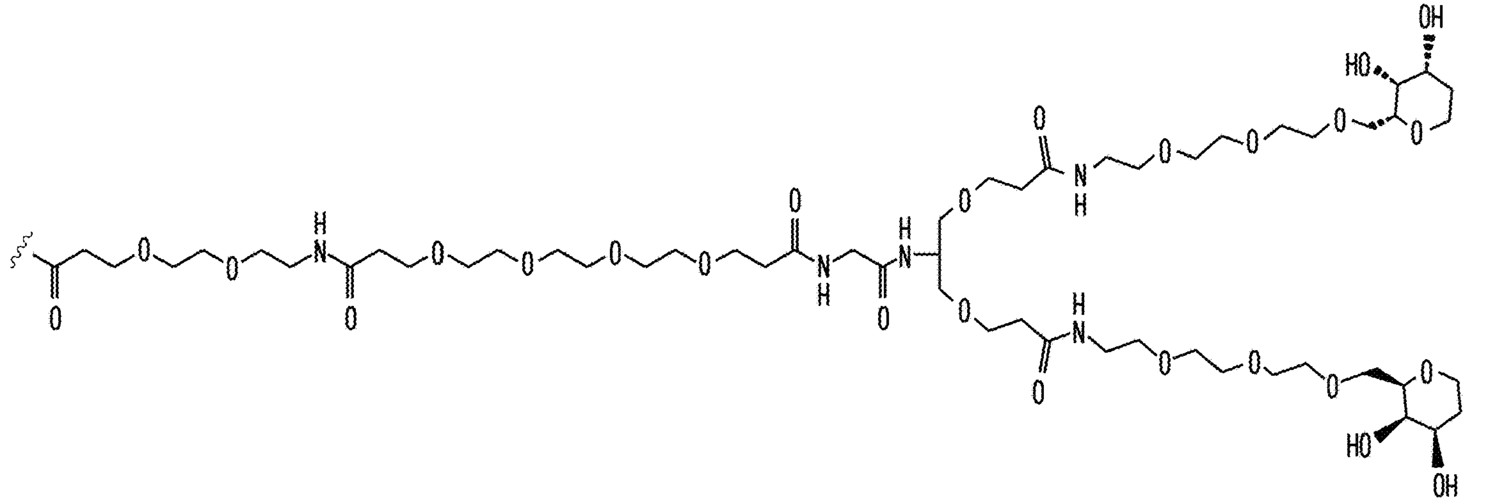
Figure 12:
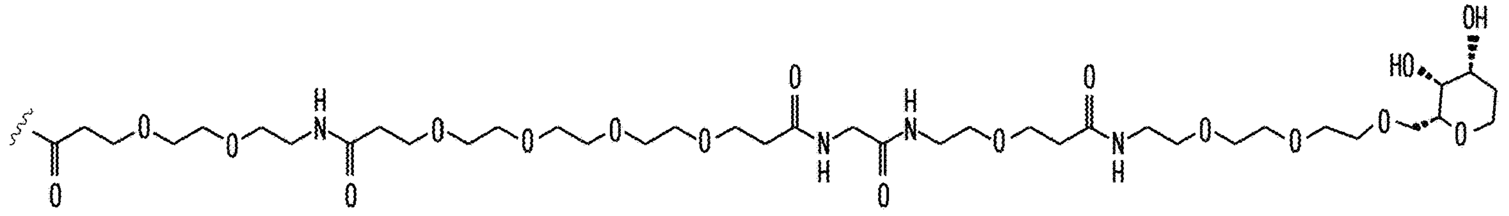
Figure 13:
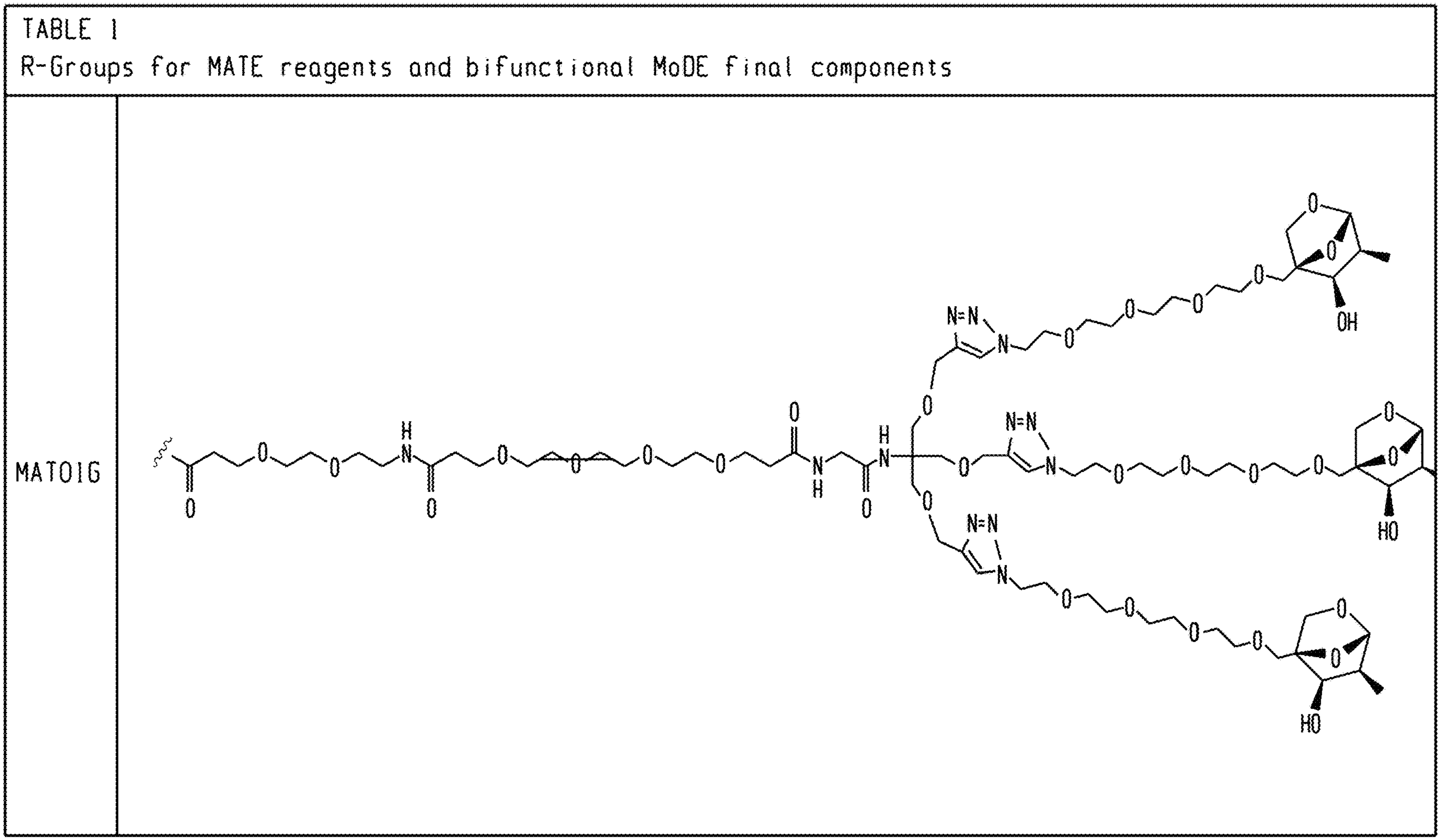
Figure 14:
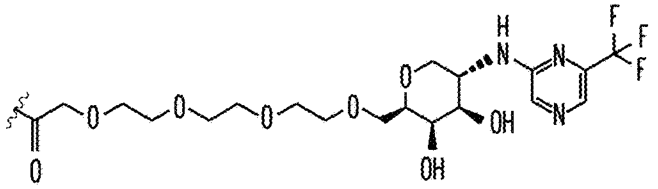
Figure 14:
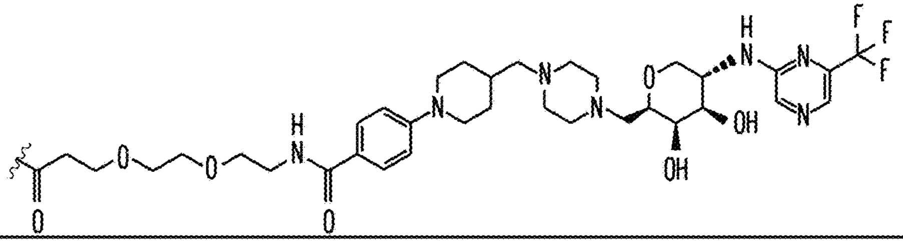
Figure 14:
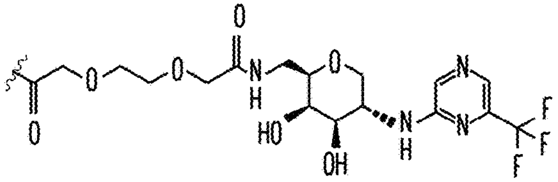
Figure 14:
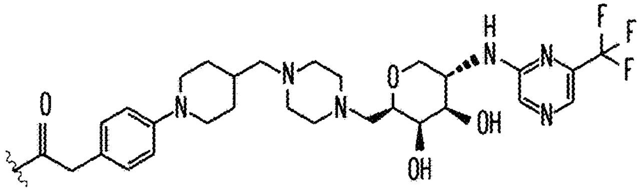

There are many publicly available approaches and mutation sets to increase the binding of an Fc to FcRn. See FIG. 7 and TABLE 5. An older summary is provided by Strohl, Current Opinion in Biotechnology, 20(6), 685-691 (2009).

TABLE 5

| Examples of Fc sequence engineering for modification of half-life | | |
|---|---|---|
| Function | Company or source | Mutations or changes |
| Increased half-life | MedImmune | IgG1-M252Y, S254T, T256E |
| Increased half-life | Protein Design Labs | IgG1-T250Q, M428L |
| Increased half-life | Genentech | IgG1-N434A |
| Increased half-life | Sally Ward | IgG1-H4J3K, N434Y |
| Increased half-life | Deny Roopenian | IgG1-T307A, E380A, N434A |
| Increased half-life | Xeocor Xtend ™ technology | |
| Lowered endogenous IgG | Sally Ward | IgG1-M252 Y, S254T, T256E, H433K, N434F, 436H |
| Decreased half-life | Deny Roopenian | IgG1-1253A |
| Decreased half-life | Ell Lilly | IgG1-P2571, N434H or Q376V, N434H |

For an example of introducing a YTE region in a protein (M252Y/S254T/T256E), see Acqua et al., The Journal of Immunology 169(9), 5171-5180 (2002). For a recent example combining LALA and YTE, see Cobb et al., bioRxiv, 2021-09 (2021). More references with details of engineering are also available.

For an example of introducing an LS region in a protein (M428L/N434S), see Zalevsky et al., Nature Biotechnology, 28(2), 157-159 (2010).

Example 2

Antibody-Drug Conjugate Production

Antibody Expression.

ExpiCHO-S cells at a density of ~6×10$^6$ cells/mL were cultured with ExpiCHO Expression Medium, and equal heavy chain and light chain vectors were transiently co-transfected into ExpiCHO-S cells by using an ExpiCHO transfection kit with the vector DNA at a final concentration of 1.0 μg/mL. Transfected cells were cultured in a shaking flask at 125 rpm in an incubator with 8% carbon dioxide at 37° C. ExpiCHO medium was added 18-22 hours after transfection.

Antibody Purification

A mixed culture of cells was collected on the 6$^{th}$ day. Harvested cell culture fluid was exchanged by Tangential Flow Filtration before dialysis against 50 mM MES, pH 6.5, and 5 mM sodium chloride. The sample was then applied to the HiTrap SP HP column (Cytiva Life Sciences), and the column was washed with 50 mM MES, pH 6.5, and 5 mM sodium chloride. Antibody was eluted over 15 C.V. gradient into 50 mM MES, pH 6.5, and 1 M sodium chloride. Eluted protein was dialyzed against 50 mM sodium phosphate, pH 7.5, and 150 mM sodium chloride. The sample was analyzed for purity by SDS-PAGE and SEC-HPLC.

Binding Affinity of Purified Antibody to Dg-IgA

In one method, 10 μg/mL deglycosylated-IgA (dg-IgA) was loaded on Protein L tips (Sartorius) in 50 mM sodium phosphate, pH 7.5, 150 mM sodium chloride, and 0.05% bovine serum albumin. Following equilibration, varying concentrations of purified antibody from 200 to 3.125 nM were analyzed for binding by 300 s Association and 600 s Dissociation. Data were fit globally and generated automatically by Octet User Software (ForteBio, Inc.). Analysis of binding kinetics was performed in Prism (GraphPad Software, Inc.). $k_{obs}$ values were extracted using a phase association equation. $k_{off}$ values were extracted using a phase decay equation. $k_{on}$ was derived using $k_{obs}=k_{on}\times[\text{Ligand}]+k_{off}$, where [Ligand] is a free ligand concentration in solution. $K_D$ was calculated as $k_{off}/k_{on}$. To correct for drift during association, the slope during the drift period was fit by linear regression, and the product of slope and time (in seconds) was subtracted from the signal.

In an alternative method, 5 μg/mL deglycosylated-IgA (dg-IgA, prepared in-house) was loaded on Protein L tips (Sartorius) in phosphate-buffered saline in the presence of 0.05% Tween-20 and 0.1% bovine serum albumin for 600 seconds. Following sixty seconds of equilibration, varying concentrations of purified antibody/ADC from 50.0 to 0.8 nM by serial two-fold dilutions were analyzed for binding by 300 s Association and 600 s Dissociation. Data were fit globally, and Kg values were generated automatically by Octet User Software (ForteBio, Inc.).

Antibody-Drug Conjugate Production

Purified antibody at 5 mg/mL concentration in 50 mM sodium phosphate, pH 7.5, and 150 mM sodium chloride was incubated with a 3-fold molar excess of tris-GalNAc conjugate in 5% DMSO for 72 hours at 25° C. Following incubation, the mixture was diluted 25-fold in 50 mM MES, pH 7.5, and 150 mM sodium chloride, then applied to the HiTrap SP HP column (Cytiva Life Sciences). The column was washed with 50 mM MES, pH 6.5, and 5 mM sodium chloride. An antibody was eluted over a 15 C.V. gradient into 50 mM MES, pH 6.5, and 1 M sodium chloride. Eluted protein was dialyzed against 50 mM sodium phosphate, pH 7.5, and 150 mM sodium chloride. The sample was analyzed for purity by SDS-PAGE and SEC-HPLC.

Example 3

Antibody-Drug Conjugate Increased Production
Development of Antibody-Based Degraders of Galactose-Deficient IgA.

A specific embodiment of the composition of matter (agent), Gd-IgA-specific MoDE AGN01A, removes Gd-IgA for ASGPR-dependent degradation. To produce this composition of matter, Gd-IgA antibody ABT010 is conjugated to ASGPR binder MAT001, yielding the MoDE AGN01A.

The purpose of this EXAMPLE is to optimize the production and subsequent conjugation of antibody ABT010 for in vivo study.

Summary of Antibody Production—First Scale.

A specific embodiment of the composition of matter (agent), ABT010, removes Gd-IgA for ASGPR-dependent degradation.

The production strategy was: (1) Expression by transient transfection in the ExpiCHO system. (2) Separating and purifying biomolecules by tangential flow (crossflow) filtration. (3) Ion-exchange chromatography using a sulphopropyl (SP HiTrap) column. (4) Dialysis against conjugation (phosphate-buffered saline) buffer. Fraction 23 was dialyzed against phosphate-buffered saline (PBS) for conjugation.

Antibody expression. ExpiCHO-S cells at a density of ~$6\times10^6$ cells/mL were cultured with ExpiCHO Expression Medium, and equal heavy chain and light chain vectors were transiently co-transfected into ExpiCHO-S cells by using an ExpiCHO transfection kit with the vector DNA at a final concentration of 1.0 μg/mL. Transfected cells were cultured in a shaking flask at 125 rpm in an incubator with 8% carbon dioxide at 37° C., and ExpiCHO medium was added 18-22 hours after transfection.

Antibody purification. A mixed culture of cells was collected on the 6th day. Harvested cell culture fluid was exchanged by Tangential Flow Filtration before dialysis against 50 mM MES, pH 6.5, and 5 mM sodium chloride. The sample was then applied to the HiTrap SP HP column (Cytiva Life Sciences), and the column was washed with 50 mM MES, pH 6.5, and 5 mM sodium chloride. Antibody was eluted over 15 C.V. gradient into 50 mM MES, pH 6.5, and 1 M sodium chloride. Eluted protein was dialyzed against 50 mM sodium phosphate, pH 7.5, and 150 mM sodium chloride. The sample was analyzed for purity by SDS-PAGE and SEC-HPLC.

The cation-exchange chromatography (SP HiTrap) step yields ~90% pure protein as estimated by SDS-PAGE analysis. The estimated yield was ~50 mg/L for an ExpiCHO expression. The binding affinity was measured to be dg-IgA KD (BLI)=23±3 nM. No aggregation was seen by SEC-HPLC.

Summary of Antibody Production—Middle Scale.

For AGN01A production, a ~100 μg reaction (5 mg/mL antibody) was generated. A 3-fold molar excess tri-GalNAc conjugate MAT001 at 25° C. for seventy-two hours.

The production of the conjugated product was seen by electrophoresis by an upward shift in species.

Biophysical characterization by Bio-Layer Interferometry (BLI), an activity assay), showed conjugate AGN01A binding affinity for dg-IgA consistent with that of unconjugated product ABT010 (Kd ~18 nM). Bio-Layer Interferometry is an optical technique for measuring macromolecular interactions by analyzing white light interference patterns reflected from a biosensor tip's surface.

The batch was ready to be tested for endotoxin removal and in mouse studies.

Conjugation Optimization.

This EXAMPLE shows that conjugating an ASGPR-binder to an antibody yields an improved 'heterobifunctional degrader.' The optimization was determined to yield enough conjugation.

The binder-antibody ratio (BAR) value measures the number of "binders," i.e., ASGPR-binders) per antibody. A BAR value of 1.8 would indicate 0.9 ASGPR-binders per heavy chain.

A BAR value ~1.5 as determined by CE-SDS was achieved for first scale AGN01A production.

Plasmid preparation: The target DNA sequence was designed, optimized, and synthesized. The complete sequence was sub-cloned into an optimized vector. Transfection-grade plasmids were maxi-prepared for TubroCHO cell expression.

Cell culture and transient transfection: TubroCHO cells were grown in serum-free expression medium. The cells were maintained in Erlenmeyer flasks at 37° C. with 8% $CO_2$ on an orbital shaker. One day before transfection, the cells were seeded at a proper density in an Erlenmeyer flask. On the day of transfection, DNA was added to the flask with cells ready for transfection. The recombinant plasmid encoding the target protein was transiently transfected into suspension TubroCHO cell cultures.

Purification and analysis: Cell culture broth was centrifuged and followed by filtration. Filtered cell culture supernatant was loaded onto an affinity purification column at a proper flow rate. After washing and elution with buffers, the eluted fractions were pooled. The buffer was exchanged for the final formulation buffer. The purified protein was analyzed by SDS-PAGE analysis to determine its molecular weight and purity. The concentration was determined by the A280 method.

A one-liter production is generated using the CHO—HP stable pool process. About 1.5 grams/L is the expected yield. $T_{onset}$=53° C., $T_{m1}$=63.25° C.

In one production, ABT010, the process produced 2.77 grams. The results were aliquoted into 10×10 ml tubes containing 276.8 mg each.

TABLE 6

| | |
|---|---|
| Name | ABT010 |
| Cell Line | CHO-HP |
| Tag/Isotype | hlgG1 hkappa |
| Purification on | MabSelect™ PrismA |
| Buffer | Phosphate-buffered saline, pH 7.2 |
| Concentration | 27.68 mg/ml |
| Purity determined by SDS-PAGE | 85% |
| Purity determined by SEC-HPLC | 95% |
| Endotoxin Level | 0.051 EU/mg |
| Total yield | 2768 mg |

A binder-antibody ratio value ~1.8 as determined by CE-SDS was achieved for large scale AGN01A production.

Antibody-Drug Conjugate Production.

Purified antibody ABT030 was exchanged to 20 mM phosphate buffer, pH 6.5, and concentrated to >12 mg/mL. The antibody was then incubated with a four-fold molar excess of MATE reagent for conjugation reaction at 10 mg/mL final antibody concentration in 2.7% DMSO for seventy-two hours at 25° C. Following incubation, TFF ultrafiltration against phosphate-buffered saline, pH 7.4, in the presence of 10% DMSO for 50 DV, was used to purify the conjugated product. Finally, the conjugated product was buffer exchanged against phosphate-buffered saline, pH 7.4, for sample formulation.

Antibody Expression and Purification.

DNA sequences for HC010 heavy chain (HC) and light chain (LC) were optimized and sub-cloned into a vector. TurboCHO cells were cultured with serum-free Expression Medium and maintained at 37° C. with 8% $CO_2$. One day before transfection, cells were seeded at density. On the day of transfection, heavy chain and light chain vectors were transiently co-transfected into TurboCHO cells. After expression, cell culture broth was centrifuged, followed by filtration. Filtered cell culture supernatant was loaded onto a MabSelect PrismA Protein A column (Cytiva Life Sciences), followed by standard wash and elution steps. Eluted protein was exchanged to phosphate-buffered saline, pH 7.2, and analyzed by SDS-PAGE, SEC-HPLC, and reduced mass spectroscopy.

A HEK293 bioluminescent cell-based assay was used to assess ASGPR-dependent uptake by cells in vitro.

General Assay Format.

Harvest HEK293 (+ASGPR) cells—phosphate-buffered saline rinse 2×.

3 ml/T182 flasks 37° C. 5-10 minutes.

Cells: $1.85\times10^6$ cells/mL, 96% live, 15.23 μm.

Set cells in 40 k/100 μl/well in DMEM+200 μg/mL G418+10% Fetal Bovine Serum grow plus 1% P/S overnight.

Dg-IgA Endocytosis Assays.

Dilute BH 3845, BH 5820, and BH 5305 to make 10× stock 150 μL (0.0938 mg/mL=0.625 μM).

Make 0.625 μM BH 3845 (7.14 mg/mL)=2 μL+148 μL optimum.

TABLE 7

Binding affinity of purified antibody to dg-IgA results

| Agent (MoDE) | ABT | HC | LC | MATE | ASGPR binder | SPR ASGPR Kd (nM) | BLI dg-IgA Kd (nM) |
|---|---|---|---|---|---|---|---|
| AGN01A | ABT010 | HC010 | LC010 | MAT001 | βGN3 | 9.16 | 0.273 |
| AGN02A | ABT020 | HC020 | LC010 | MAT001 | βGN3 | | 0.253 |
| AGN03A | ABT030 | HC030 | LC010 | MAT001 | βGN3 | | 0.234 |
| AGN01B | ABT010 | HC010 | LC010 | MAT002 | βGN2 | 1.17 | 0.296 |
| AGN02B | ABT020 | HC020 | LC010 | MAT002 | βGN2 | | 0.253 |
| AGN01C | ABT010 | HC010 | LC010 | MAT003 | αGN3 | | |
| AGN01D | ABT010 | HC010 | LC010 | MAT004 | αGN2 | | |
| AGN01E | ABT010 | HC010 | LC010 | MAT005 | desOH2 | 0.0379 | 0.329 |
| AGN01F | ABT010 | HC010 | LC010 | MAT006 | desOH1 | 8.12 | 0.331 |
| AGN01G | ABT010 | HC010 | LC010 | MAT007 | PR3 | 0.0863 | 0.298 |
| AGN01H | ABT010 | HC010 | LC010 | MAT008 | TFP1 | | 0.282 |
| AGN01I | ABT010 | HC010 | LC010 | MAT009 | TFP1 | | 0.304 |
| AGN01J | ABT010 | HC010 | LC010 | MAT010 | TFP1 | | |
| AGN01K | ABT010 | HC010 | LC010 | MAT011 | TFP1 | | |

Biophysical/Biochemical Potency Assay to Measure Target Engagement.

A biomolecule is coupled to the surface of the sensor chip as a ligand. As the analyte is flowed in solution over the immobilized ligand, binding to the sensor chip surface induces a change in refractive index (RU) proportional to the bound mass. This was done using a Biacore S200 instrument with a high sensitivity and low-medium throughput. Deglycosylated IgA was immobilized to the CM5 chip via amine coupling right before assaying. Deglycosylated-IgA-binding analyte AGN03A was dosed from 1 nM to 1 μM via six 4-fold serial dilutions, in single-cycle kinetics experiment set-up. Binding affinity (Kd) was derived by steady-state approach, wherein RU is plotted against analyte concentration. AGN03 Kd value of 19 nM±1 nM was extracted from two independent biological replicates.

ASGPR-Dependent Uptake Assay to Measure Endocytosis.

Make 0.625 μM BH 5820 (9 mg/mL)=1.6 μL+148.4 μL optimum.

Make 0.625 μM BH 5305 (5.26 mg/mL)=2.7 μL+147.3 μl optimum.

Dilute ⅓ 100 optimum+50 μl sample for six concentrations.

#7: 1/10 15 μL+135 μL optimum.

Last is a blank antibody.

Make detection antibodies to add to well's stock.

Column 1-6:1.1 ug/mL dg-IgA-594-5 ml (5.5 μL dg-IgA).

Column 7-12:1.1 ug/mL IgA-594-5 ml (2.75 μL IgA).

After the overnight growth, manually remove media.

Add 90 μl dg-IgA/IgA mAb or 0 Ab for controls.

Add 10 μl of step-diluted compounds to the first nine columns and 10 μl optimum to the remaining columns.

Incubate overnight—Incucyte read @ four hours, twelve hours, and twenty hours in red channel.

TABLE 8

Unfilled assay table

| — | dg-IgA | | | IgA | | |
|---|---|---|---|---|---|---|
| nM cmp. | AGN01G | AGN03A | ABT030 | AGN01G | AGN03A | ABT030 |
| 62.500 | | | | | | |
| 20.833 | | | | | | |
| 6.944 | | | | | | |
| 2.315 | | | | | | |
| 0.772 | | | | | | |
| 0.257 | | | | | | |

TABLE 8-continued

| Unfilled assay table | | | | | | |
|---|---|---|---|---|---|---|
| — | dg-IgA | | | IgA | | |
| nM cmp. | AGN01G | AGN03A | ABT030 | AGN01G | AGN03A | ABT030 |
| 0.026 | | | | | | |
| 0.000 | | | | | | |

TABLE 9

| 1 μg/ml dg-IgA or IgA (A594) | | | | | | |
|---|---|---|---|---|---|---|
| Assay #1 | AGN01G-dg-IgA | AGN03A-dg-IgA | ABT030-dg-IgA | AGN01G-total IgA | AGNO3A-total IgA | ABT030-total IgA |
| High MFI | 25820.4 | 6192.0 | 429.9 | 74.7 | 83.9 | 240.3 |
| $EC_{50}$ | 1.071 | 2.52 | 0.3531 | 86.32 | 55.28 | 7.149 |
| S/N | 329.6 | 72.0 | 4.3 | | | |
| Z prime | 0.84 | 0.87 | −1.43 | −0.49 | 0.50 | −3.16 |
| Assay #2 | AGN01G-dg-IgA | AGN03A-dg-IgA | ABT030-dg-IgA | AGN01G-total IgA | AGNO3A-total IgA | ABT030-total IgA |
| High MFI | 72355.5 | 22824.0 | 444.1 | 363.9 | 91.4 | 198.3 |
| $EC_{50}$ | 1.074 | 1.755 | | 7.39 | 27.35 | |
| S/N | 660.1 | 201.1 | 3.7 | 806.1 | 101.2 | |
| Z prime | 0.93 | 0.96 | −1.57 | 0.53 | 0.65 | −2.94 |
| Assay #3 | AGN01G-dg-IgA | AGN03A-dg-IgA | ABT030-dg-IgA | AGN01G-total IgA | AGNO3A-total IgA | ABT030-total IgA |
| High MFI | 83454.5 | 28485.8 | 453.6 | 2102.3 | 132.4 | 196.2 |
| $EC_{50}$ | 1.275 | 1.382 | 3.533 | 20.55 | 9.872 | |
| S/N | 911.4 | 221.9 | 7.1 | | | |
| Z prime | 0.98 | 0.95 | −1.86 | 0.39 | 0.70 | −2.98 |

Example 4

Targeted Degradation of Circulating Galactose-Deficient IgA1 Using a Lysosomal Targeting Bifunctional Conjugate AGN03A is an antibody-based, bifunctional conjugate designed to bind and degrade pathogenic circulating galactose-deficient IgA1 and IgG:Gd-IgA1 immune complexes via ASGPR-mediated hepatocyte internalization. Compelling preclinical evidence has been obtained in cellular and rodent experiments for the use of AGN03A for rapid and robust degradation of deglycosylated IgA and related protein aggregates. AGN03A recognizes pathogenic galactose-deficient IgA1 in human IgAN and kidney disease patient plasma samples. AGN03A holds therapeutic potential as a transformative non-immunosuppressive treatment for patients with IgAN.

Synthesis of agent. The MoDE platform develops bifunctional molecules that degrade extracellular protein targets via the asialoglycoprotein receptor (ASGPR)-mediated endosome/lysosome pathway. The inventors engineered an anti-human galactose-deficient IgA1 chimeric antibody with a human IgG1 Fc region. The ASGPR-binding bifunctional conjugate (AGN03A) was assembled from antibody ABT030 in one step, using proprietary FcIII-directed MATE™ technology (disclosed in TABLE 2), with four equivalents of MATE reagent in an intravenous buffer w/10% DMSO. Linker and ASGPR binder were attached via a stable amide connection. AGN03A was isolated with good yield and homogeneity (binder-to-antibody ratio (BAR)=2, at about 87%). Site-specific conjugation of dual Lys248 residues was confirmed by peptide mapping.

Synthesis of deglycosylated IgA. Deglycosylated IgA (dg-IgA) is a semi-synthetic galactose-deficient IgA1 surrogate prepared from pooled human serum IgA in three enzymatic steps. Human serum IgA was treated with PNGase, neuraminidase, and galactosidase to produce deglycosylated IgA (dg-IgA).

Figure 16:
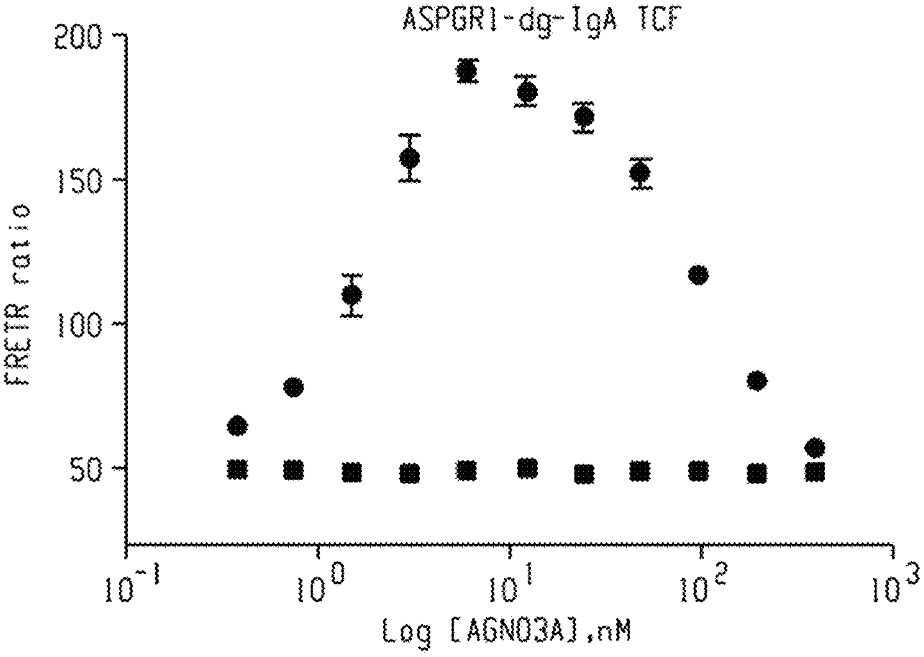
FIG. 16 is a graph showing the ASPGR1-dg-IgA TCF, depicted as FRET R ratio versus Log [AGN03A], nM. The circles show the formation of a viable ternary complex, including the agent AGN03A. The squares show the phosphate-buffered saline control results.

Demonstrated ability to engage ASGPR and protein of interest (POI) simultaneously. AGN03A demonstrated strong affinity for dg-IgA (KD=4 nM) and the carbohydrate recognition domain of ASGPR1(148-291) (KD=9 nM). A proximity-based time-resolved fluorescence resonance energy transfer assay provided evidence for forming a viable ternary complex with the hook effect. See FIG. 16.

Figure 17:
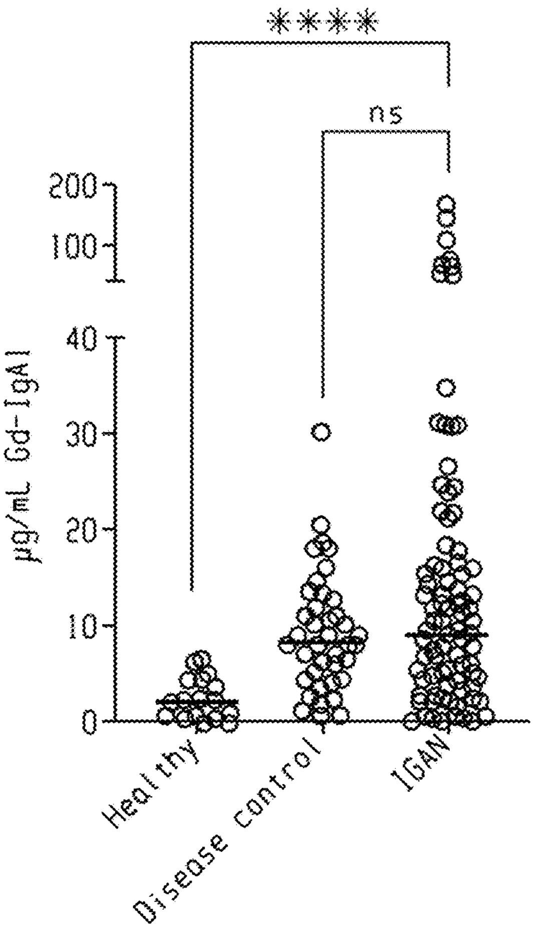
FIG. 17 is a graph showing the detection of galactose-deficient IgA1 levels in human plasma samples. Compare to FIG. 15.

Detection of galactose-deficient IgA1 levels in human plasma samples. Galactose-deficient IgA1 antibody concentrations in patient plasma samples were measured using Meso Scale Discovery with immobilized AGN03A and SULFO-TAG anti-IgA antibody. Galactose-deficient IgA1 levels in samples from patients with kidney disease and IgAN were about four-fold higher than in healthy volunteers. Results were consistent with the literature reports using a KM55 diagnostic. See FIG. 15. The results confirm that AGN03A recognizes significant levels of circulating galactose-deficient IgA1 and corresponding immune complexes. See FIG. 17.

TABLE 10

| | Healthy participants (n = 26) | Participants with kidney disease (n = 40) | Participants with IgAN (n = 95) |
|---|---|---|---|
| Gd-IgA1 (μg/mL) | 2 ± 2 | 8 ± 6 | 9 ± 30 |

Figure 18:
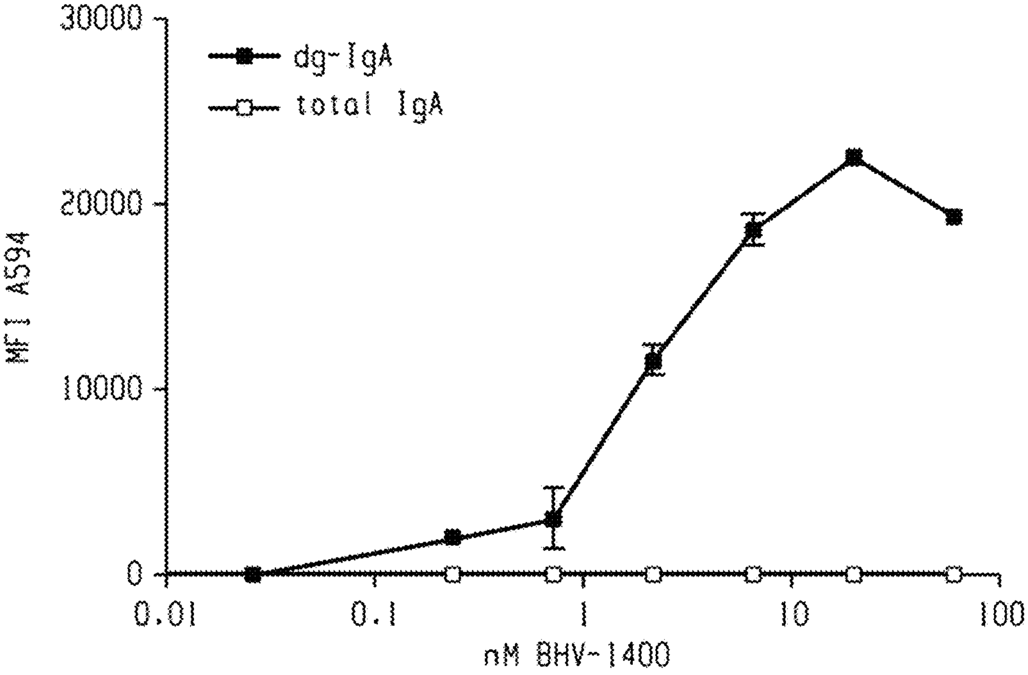
FIG. 18 is a graph showing the results of a dg-IgA cell internalization assay. HEK293 cells transfected with ASGPR1 were used to measure the endocytosis of 1 μg/mL dg-IgA and total IgA conjugated to Alexa Fluor 594. MFI=mean fluorescence intensity, S/N=signal-to-noise ratio.

In vitro cellular internalization of dg-IgA with AGN03A. Dose-dependent, selective endocytosis of dg-IgA versus IgA was observed with AGN03A in human embryonic kidney (HEK) cells transfected with human ASGPR1 (hASGPR1). Low-nanomolar half-maximal effective concentration and robust mean fluorescence were observed at twelve hours for internalization of dg-IgA conjugated to Alexa Fluor 594. AGN03A internalizes protein of interest for lysosomal degradation but spares normal IgA. See FIG. 18.

Cellular internalization of dg-IgA1 antibody complexes. Dose-dependent, selective endocytosis of dg-IgA versus IgA was observed with AGN03A in human embryonic kidney (HEK) cells transfected with human ASGPR1 (hASGPR1). Low-nanomolar half-maximal effective concentration and robust mean fluorescence were observed at twelve hours for internalization of dg-IgA conjugated to Alexa Fluor 594. AGN03A internalizes the protein of interest for lysosomal degradation but spares normal IgA.

TABLE 11

| | dg-IgA | Total IgA |
|---|---|---|
| High MFI | 22,824 | 91.4 |
| $EC_{50}$ (nM) | 1.75 | 27.5 |
| S/N | 201 | 101 |
| Z prime | 0.96 | 0.65 |

HEK293 cells transfected with ASGPR1 were used to measure endocytosis of 1 μg/mL dg-IgA and total IgA conjugated to Alexa Fluor 594. MFI=mean fluorescence intensity, S/N=signal-to-noise ratio.

Figure 19:
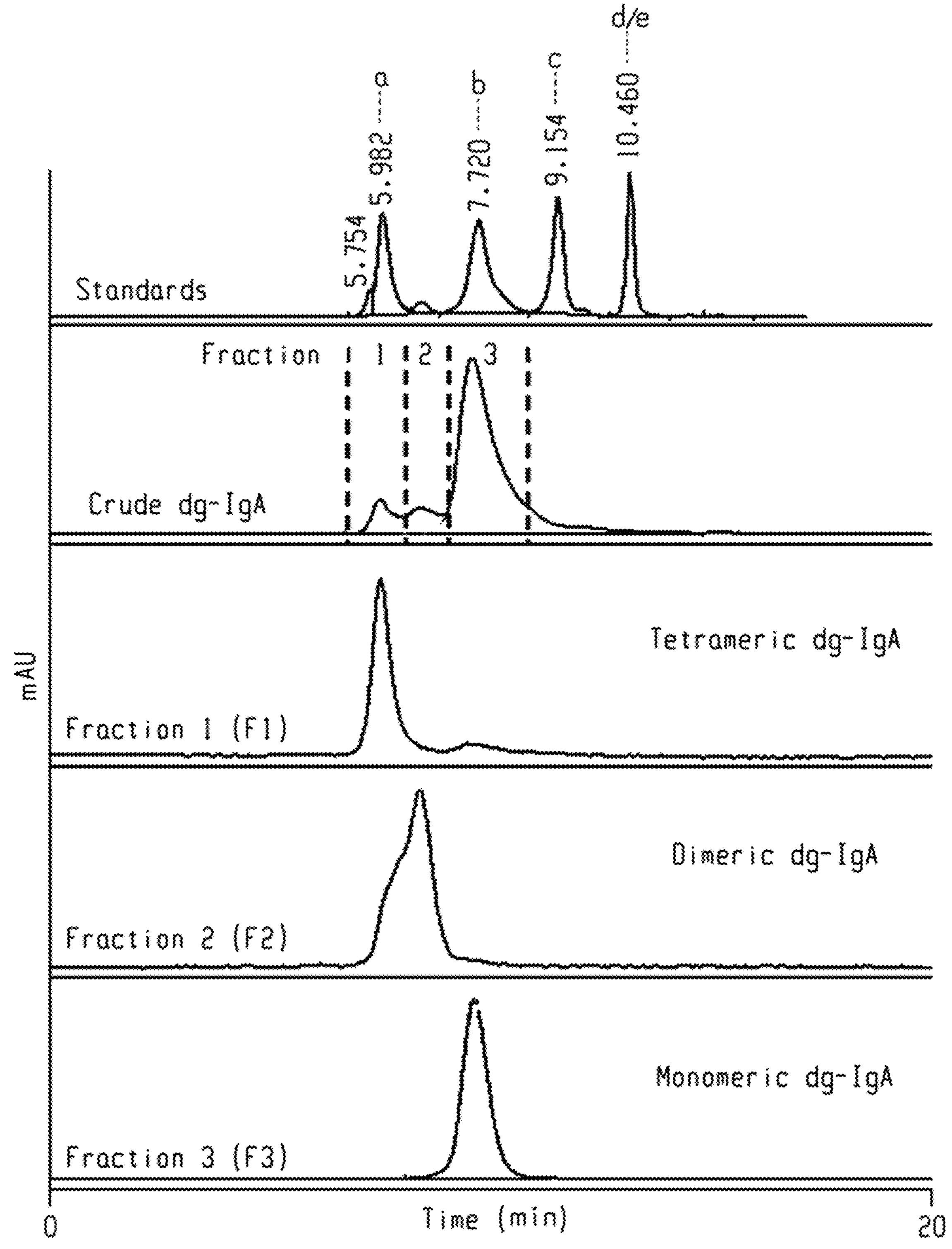
FIG. 19 is a graph showing the isolation of dg-IgA aggregates by size exclusion chromatography. See TABLE 10.

Isolation of dg-IgA aggregates by size exclusion chromatography. dg-IgA conjugated to Alexa Fluor A594 was separated into three fractions corresponding to tetrameric, dimeric, and monomeric forms. All three forms of dg-IgA were advanced into the cell internalization assay. See FIG. 19.

TABLE 12

| Peak | Analyte | MW (daltons) |
|---|---|---|
| A | Thyroglobulin | 670,000 |
| B | γ-globulin | 150,000 |
| C | Ovalbumin | 45,000 |
| D | Myoglobin | 17,000 |
| E | Angiotensin II | 1000 |

Figure 20:
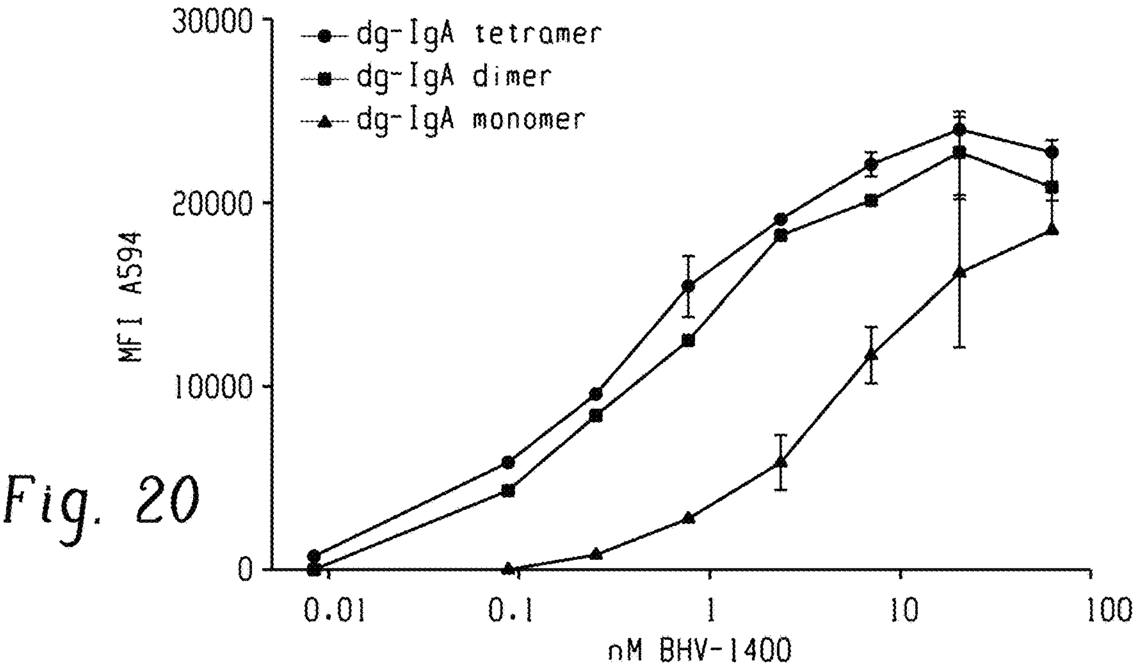
FIG. 20 is a graph showing the results of cell internalization of dg-IgA complexes. HEK293 cells transfected with ASGPR1 were used to measure endocytosis of 1 μg/mL monomeric, dimeric, and tetrameric dg-IgA conjugated to Alexa Fluor 594. See TABLE 11.

Cellular internalization of dg-IgA1 antibody complexes. AGN03A demonstrated efficient internalization of dimeric and tetrameric dg-IgA complexes in HEK (hASGPR1) cells at twelve hours, similar to the dg-IgA monomer. AGN03A can internalize and degrade large IgA antibody complexes. See FIG. 20.

TABLE 13

| | Tetrameric dg-IgA | Dimeric dg-IgA | Monomeric dg-IgA |
|---|---|---|---|
| High MFI | 120,138 | 115,102 | 94,422 |
| $EC_{50}$ (nM) | 0.37 | 0.48 | 3.93 |
| S/N | 57.9 | 139.9 | 678.9 |
| Z prime | 0.87 | 0.66 | 0.87 |

HEK293 cells transfected with ASGPR1 were used to measure endocytosis of 1 μg/mL monomeric, dimeric, and tetrameric dg-IgA conjugated to Alexa Fluor 594.

Figure 21:
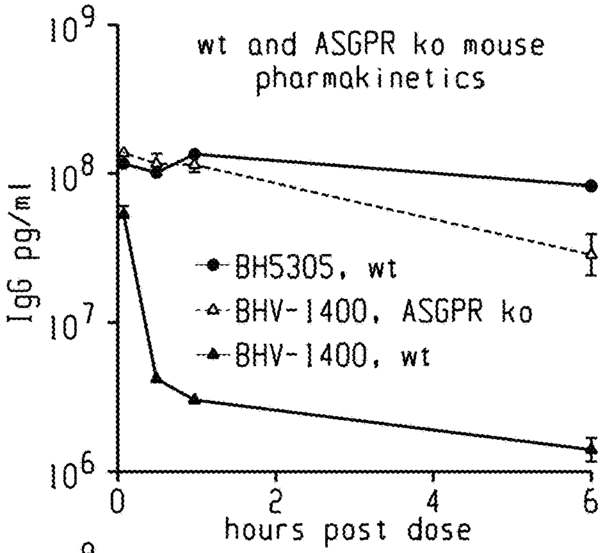
FIGS. 21 and 22 are line graphs showing the results of the administration of agent to mice. The line graph on the left shows the pharmacokinetics resulting from administering wild-type mice and ASGPR knockout (KO) mice. The line with the closed triangles shows the results of the administration of AGN03A to wild-type mice. The line with the open triangles shows the results of the administration of AGN03A to ASGPR knockout (KO) mice. The line with the closed circles shows the results of administering the antibody ABT030 to wild-type mice. The line graph on the right shows the pharmacodynamics of dg-IgA clearance in wild-type mice. The line with the triangles shows the clearance of AGN03A. The line with the squares shows the clearance of antibody ABT030. The line with the circles shows the clearance of dg-IgA. The dosage was AGN03A intravenous, 200 μg/mouse=8 mpk dg-IgA intravenous, 100 μg=4 mpk (five times higher than the patient's median galactose-deficient IgA1 level).
Figure 22:
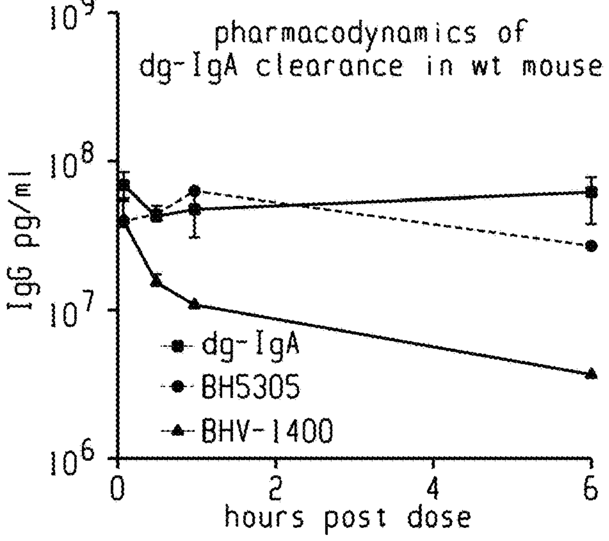

AGN03A achieves robust degradation of exogenous dg-IgA in mice. After intravenous administration, AGN03A demonstrated ASGPR-dependent clearance in wild-type mice versus ASGPR1 knockout (KO) mice. Results were consistent with the AGN03A mechanism of action. AGN03A depleted exogenous dg-IgA in wild-type mice to 58% of the area under the curve of control at a 2:1 (drug: target) ratio after sequential intravenous (IV) administration. Parent control antibody, ABT030, did not affect the degradation of exogenous dg-IgA in wild-type mice as anticipated. AGN03A rapidly and robustly degrades an enzymatically deglycosylated form of human IgA administered to mice. See FIGS. 21 and 22.

Example 5

Improved Conjugation Methods

Cysteine-based conjugation of Km55 variants does not present selective conjugation opportunities.

Site-specific conjugation of Lys248 on HCs of Fc via proprietary FcIII-directed MATE (disclosed in TABLE 2) yields global DAR value of ~2.0, >80%-target DAR (DAR2). Four equivalents of MATE reagent (in several examples, FcIII, a thirteen-membered cyclic peptide) was incubated with a Km55 variant antibody in phosphate-buffered saline with 10% DMSO at pH 7.4 for forty-eight hours. This product was then incubated in TFF buffer exchange to remove the FcIII moiety, resulting in the composition of matter (agent).

In several examples, conjugation of mAb by MATE reagent demonstrates site-specificity at Lys248. ~91-92% of the conjugation occurred at the expected site, heavy chain K248 (or heavy chain K247 in the linear numbering). ~0.3% occurred at the proximal lysine to MATE reagent-binding site, heavy chain K246 (or heavy chain in linear numbering). The second most populated site is heavy chain at ~7-9% occupancy, which is at the C-terminal end of the $CH_1$ domain, several residues before the start of the hinge region. The third most populated site is the N-terminal amine of the LC, at 0.7% occupancy. The remaining 15 sites are occupied at <=0.5%.

The inventors performed the steps of the conjugation using Km55 variants:

Clarification.

Direct product capture (DPC).

Viral inactivation.

Indeterminate depth filtration.

Indeterminate ultrafiltration/diafiltration (UF/DF).

Conjugation. Conjugation development within downstream processing. Conjugation occurs as part of the mAb manufacture process.

Cation exchange chromatography (CEX). MATE Reagent and hydrolyzed GalNac can be removed by CEX chromatography, but not the FcIII peptide.

Affinity chromatography (AC). Conjugation methods incorporated subsequent protein A-based affinity chromatography before ion-exchange steps. A protein A column removes excess MATE reagent. Capture chromatography is efficient for completely removing FcIII peptide. Capture chromatography (protein A) column is reused post conjugation.

Anion exchange chromatography (AEX).

Ultrafiltration/diafiltration (UF/DF). FcIII Peptide can be removed by UF/DF on small scale, but large scale purification is difficult. Aggregation with DMSO cosolvent has many diavolumes.

Formulation.

The inventors developed sensitive analytical methods for each (HPLC). Expected LOQ~400 ppm.

Typical bioconjugations to make antibody-drug conjugates are normally performed on fully purified and release tested mAbs in a separate facility. The use of a non-cytotoxic payload increases the opportunity for an 'Integrated' approach.

The inventors streamlined the purification and testing. Expected >2m improvement in overall cycle time.

Conjugation conditions. A set of suitable range assays assessed pH and temperatures for conjugation. The target is >80% DAR2. Higher temperature increases DAR2 at twenty-four hours. Lower pH (pH ~6.0 to 6.2) favors DAR1, and higher pH (pH ~6.2 to 6.4) favors DAR3.

TABLE 14

| | Conjugation Conditions | | | | |
|---|---|---|---|---|---|
| Reaction | Temp. (°C.) | mAb conc. (mg/ml) | LP/mAb molar ratio | pH | Conjugation time (hours) |
| RXN001 (preferred) | 33 | 20 | 2.5 | 6.2 | 24, 48 |
| RXN002 | 30 | 20 | 2.5 | 6.2 | 24, 48 |
| RXN003 | 35 | 20 | 2.5 | 6.2 | 24, 48 |
| RXN004 | 27 | 20 | 2.5 | 6.2 | 24, 48 |
| RXN005 | 33 | 20 | 2.4 | 6.2 | 24, 48 |
| RXN006 | 33 | 20 | 2.6 | 6.2 | 24, 48 |
| RXN007 | 33 | 20 | 2.5 | 6.0 | 24, 48 |
| RXN008 | 33 | 20 | 2.5 | 6.1 | 24, 48 |
| RXN009 | 33 | 20 | 2.5 | 6.3 | 24, 48 |
| RXN010 | 33 | 20 | 2.5 | 6.4 | 24, 48 |

The inventors then pursued improved methods for selectivity for bioconjugation using MATE technology. The inventors evaluated three buffers. All three gave comparable results. The 20 nM phosphate buffer selected.

The inventors tested several conditions using a Design of Experiments approach. They collected size-exclusion chromatography (SEC) data and mass spectroscopy DAR data. The results of a first round of one-factor-at-a-time (OFAT) analysis drove further optimization of conditions after the analysis showed that >80% DAR2 was achievable. After the inventors conducted a suitable range analysis, they chose final conditions to achieve 88% target-DAR2.

TABLE 15

| | |
|---|---|
| Temperature | 33° C. (30°-35° C.) |
| pH | 6.1 (6.0-6.2) |
| mAb concentration (mg/ml) | 20% (±3%) |
| LP/mAb molar ratio | 2.5 (2.4-2.6) |
| Time (hours) | 48 (±1) |

The inventors performed peptide mapping to confirm conjugation site selectivity. They also confirmed that controlling pH is important for preventing 'off-target' conjugation. pH=6.0 gives the preferred conjugation at the desired lysine only. Equivalents of LP can be reduced to 2.5 equivalents, but a preferred reaction time requires an elevated temperature of 35° C.

TABLE 16

| | Conjugation Site Occupancy (%) | |
|---|---|---|
| Conjugation Sites | Conjugation 48 hours | Conjugation AGC DS |
| Heavy chain N-terminal | 0.1% | <0.1% |
| Heavy chain K64 | 0.2% | 0.1% |
| Heavy chain K75 | 0.1% | 0.1% |
| Heavy chain K213 | 0.1% | 0.1% |
| Heavy chain K221 | 0.3% | 0.4% |
| Heavy chain K247 | 91.5% | 91.8% |
| Light chain N-terminal | 0.2% | 0.2% |
| Light chain K74 | 0.1% | <0.1% |
| Light chain K195 | 0.1% | 0.1% |

Midscale Purification.

The results were comparable to the results from small scale with the same conjugation conditions.

A 3 L production run was performed to generate Km55 variant for conjugation to make a composition of matter (agent). The 3 L MCB run had comparable cell growth and metabolism profiles with the 15 L run.

A 15 L production run was performed to generate Km55 variant for conjugation to make a composition of matter (agent). A 3 L MCB confirmation run achieved comparable cell growth and productivity with the 15 L run.

mAb: Buffer: 20 mM PB, pH6.5

Concentration: 16.40 mg/mL

UF/DF: DF buffer: 20 mM PB, pH6.2

Concentration: 23.81 mg/mL

Conjugation concentration: 20 mg/mL,

LP/mAb molar ratio: 2.5, LP batch No.: MC01432-4-P-L1

Temperature: 33° C.

pH: 6.2

Time: 48 hours

Quench: Adjusting pH to 5.1 with 1M acetic acid

After quenching and sampling, the product was stored in −70° C.

DAR1 species decreased after CEX under low load density (Load density: 32.3 g/L, lower than in PD 45-50 g/L) and DAR3 species decreased after AEX in 15 L material generation.

Larger Scale Purification (Robust Process).

A 500 L production run was performed to generate Km55 variant for conjugation to make a composition of matter (agent). The titers of 500 L and 3 L satellite runs were comparable with that of the 15 L run. An upstream production was completed successfully with 6.15 g/L titer and 511.90 L culture fluid, after fourteen days in culture. The process parameters were:

Filter: 90ZB: Load density: 93 L/$m^2$ (≤100 L/$m^2$).

Resin: MabSelect PrismA: Column I.D.: 30.0 cm, B.H.: 21.5 cm (15-25 cm), CV: 15.197 L Load density: 46.4 (Run1), 43.6 (Run2), 46.9 (Run3), 45.7 (Run4) g/L resin (20-50 g/L resin).

Low pH: pH 3.59 (3.50-3.70).

Neutralization pH: pH 5.45 (5.3-5.7).

Filter: 90ZB: Load density: 1667 g/$m^2$ (≤2000 g/$m^2$).

Filter: Pellicon 3, PES, MWCO 30 kDa, A screen: Load density: 550 g/$m^2$ (≤1000 g/$m^2$). DF/OC conc. are 25.2 and 35.2 g/L, respectively.

DF buffer: 20 mM PB, pH 6.1; UF/DF pool conc.: 25.7 (22.5-27.5) g/L.

mAb: 20 mg/mL; MATE reagent/mAb molar ratio: 2.5; Conjugation buffer: 20 mM PB, pH 6.1; 33° C., 2 days.

Post-conjugation purification. Resin: POROS XS: Column I.D.: 30.0 cm, B.H.: 22.9 cm (15-25 cm), CV: 16.187 L.

Load density: 43.0 (Run1), 41.1 (Run2) g/L resin (28-45 g/L resin).

Resin: MabSelect PrismA: Column I.D.: 30.0 cm, B.H.: 25.1 cm (15-25 cm), CV: 17.742 L.

Load density: 37.3 (Run1), 37.4 (Run2) g/L resin (20-40 g/L resin).

Resin: POROS 50HQ: Column I.D.: 20.0 cm, B.H.: 21.6 cm (15-25 cm), CV: 6.785 L.

Load density: 169.8 g/L resin (50-300 g/L resin).

Viral Filter: Planova BioEX: 1 m2.

Load density: 54 L/m2 (≤288 L/m2).

Filter: Pellicon 3, CRC, MWCO 30 kDa, C screen: Load density: 501 g/$m^2$ (≤800 g/$m^2$).

DF buffer: 20 mM His, pH 5.7; UF/DF pool conc.: 77.5 g/L.

Formulation buffer: 20 mM His, 8% (w/v) Sucrose, 0.02% (w/v) PS80, 5 mM Methionine, pH 5.7.

Target AGC concentration: 50.0 mg/mL.

Total 101.063 L mAb intermediate, in 20 mM PB, pH 6.1.

Formulation buffer: 20 mM His, 8% (w/v) Sucrose, 0.02% (w/v) PS80, 5 mM Methionine, pH 5.7.

The 500 L non-GMP production was completed successfully, no unexpected events occurred. The overall yield is 81.4%, step yield of individual operation unit is comparable to the PD data (see above). The chromatograms of affinity chromatography are comparable to the PD data.

Post-conjugation purification accumulative yield: 87% (from CEX to UF/DF). The protein concentration measured by Protein A HPLC was 4.59 g/L with 312.48 L and 4.57 g/L with 304.36 L after clarification and the clarification step yield was 89.7%. A 14.63 L UF/DF Pool (77.5 mg/mL, 1134.1 g Compound 1) was used for formulation and 22.55 L DS (1127.5*g Compound 1) was obtained for aliquot.

AGC DS Formulation: 50.0 (target) mg/mL AGC, 20 mM His, 8% (w/v) Sucrose, 0.02% (w/v) PS80, 5 mM Methionine, pH 5.7.

The mAb intermediate non-GMP 500 L production downstream process was completed successfully with the overall yield of 81.4% (from Clarification to Int. UF/DF).

The step yield of individual operation unit and chromatograms are comparable to the PD data.

The final composition of matter (agent) that was produced by this larger scale purification was about 1 kg. Accordingly, amount of composition of matter (agent) that could be produced was 1 kg or more.

Example 6

Surface Plasmon Resonance (SPR), an Activity Assay.

The inventors performed surface plasmon resonance to confirm the binding of AGN03A to dg-IgA. CM5 amine coupling shows a binding response but is not viable for batch release quantitation (KD>100 nM, low active surface). The assay provides robust and repeatable results with orientation-specific protein-L capture.

TR-FRET Assay.

To assess the formation of a ternary complex between ASGPR-1, AGN03A, and dg-IgA, a time-resolved fluorescence resonance energy transfer (TR-FRET) assay was used. AGN03A was diluted two-fold across twelve points in phosphate-buffered saline pH 7.4 and transferred to a 384-well ProxiPlate (Revvity) using an Echo 650 liquid handler (Beckman Coulter) to achieve final test concentrations: 400 nM, 200 nM, 100 nM, 50 nM, 25 nM, 12.5 nM, 6.25 nM, 3.1 nM, 1.6 nM, 0.78 nM, 0.39 nM, 0 nM. Phosphate-buffered saline solvent alone was added to the plate as a negative control for no expected induction of the protein-protein interaction.

A solution containing 25 nM biotin-ASGPR-1 (Viva Biotech) and 5.5 nM dg-IgA was prepared in 1× assay buffer (25 mM HEPES pH 7.5, 150 mM NaCl, 5 mM $CaCl_2$), 1 mM DTT, 0.01% Tween-20) and added to the assay plate containing AGN03A dilutions and phosphate-buffered saline controls. Following a sixty-minute incubation at room temperature, a solution containing 3 nM streptavidin-Europium cryptate (Revvity) and 25 nM goat anti-human IgA-AlexaFluor 647 conjugate (Jackson ImmunoResearch) was made up of 1× assay buffer and added to the plate. The reaction was incubated for an additional sixty minutes. TR-FRET was measured using an Envision multilabel reader (Revvity) with filters for excitation at 320 nm and emission at 665 nm and 615 nm. TR-FRET values were calculated as a ratio of 665 nm to 615 nm emission, normalized [(665/615)*1000], and plotted as the response at each test concentration of AGN03A. Increase in TR-FRET ratio as a function of test concentration indicates induced proximity of labeled-ASGPR and dg-IgA, which thereby demonstrates AGN03A-mediated ternary complex formation.

The TR-FRET signal is dependent on AGN03A-induced proximity of ASGPR, dg-IgA. For information about the assay, see Pettersson & Crews, Drug Discovery Today: Technologies, Vol. 31, pp. 15-27 (2019). Induced proximity between ASGPR and dg-IgA generates a specific energy transfer signal.

The inventors titrated ASGPR and dg-IgA over fixed [Compound 1] and fixed donor/acceptor fluorophores. The signal "hot spot" on the matrix confirmed that PPI is detectable and identified ideal concentrations of dg-IgA and ASGPR1.

TABLE 17

| [AlexaFluor ab], nM | S/B |
|---|---|
| 200 | 1.5 |
| 100 | 2.0 |
| 50 | 2.3 |
| 25 | 2.3 |
| 12.5 | 2.1 |
| 6.3 | 1.6 |
| 3.1 | 1.4 |
| 1.6 | 1.2 |
| 0.8 | 1.1 |

TABLE 17-continued

| [AlexaFluor ab], nM | S/B |
|---|---|
| 0.4 | 1.1 |
| 0.2 | 1.0 |
| 0 | 1.0 |

After optimization of protein and fluorophore concentrations, AGN03A was dosed from 0.4 to 400 nM. Ternary complex and hook effect specific to the presence of AGN03A. The response is specific to induced proximity between ASGPR and dg-IgA. 6-12 nM AGN03A produces peak response of ~3.5× signal/background in this system. The response is specific to galactose-deficient IgA versus native IgA.

The resulting signal emission from the acceptor is proportional to the level of interaction.

In summary, a ternary complex was observed between ASGPR1, Compound 1, and dg-IgA.

EQUIVALENTS

Persons having ordinary skill in the biomedical art will recognize or be able to determine using no more than routine experimentation many equivalents to the specific procedures described. Such equivalents are considered within the scope of this invention and are covered by these claims. Pharmaceutically acceptable salts other than those specifically revealed in the description and Examples herein can be employed. Furthermore, it is intended that specific items within lists of items, or subset groups of items within larger groups of items, can be combined with other specific items, subset groups of items, or larger groups of items whether or not a specific disclosure herein identifies this combination.

REFERENCES

Persons having ordinary skill in the biomedical art can use these patents, patent applications, and scientific references as guidance to predictable results when making and using the invention.

Patent Literature

U.S. Pat. No. 7,083,784 (Dall'Acqua et al.), Molecules with extended half-lives, compositions and uses thereof.

U.S. Pat. No. 7,658,921 (Dall'Acqua et al.), Molecules with extended half-lives, compositions and uses thereof.

U.S. Pat. No. 8,088,376 (Chamberlain et al.), Fc variants with changed binding to FcRn.

U.S. Pat. No. 8,969,526 (Baehner), Antibody Fc variants.

U.S. Pat. No. 9,562,100 (Dall'Acqua et al.), Molecules with extended half-lives, compositions and uses thereof.

U.S. Pat. Publ. 2020/0190165 (Yamada et al.), Compound having affinity substance to soluble protein, cleavable portion and reactive group, or salt thereof.

European Pat. No. EP1355919 (MedImmune LLC et al.), Molecules with extended half-lives, compositions and uses thereof.

Intl. Pat. Publ. WO 2002/060919 (MedImmune LLC et al.), Molecules with extended half-lives, compositions and uses thereof.

Intl. Pat. Publ. WO 2012/017021 (Graffinity Pharmaceuticals GmbH), Ligands for antibody and Fc-fusion protein purification by affinity chromatography.

Intl. Pat. Publ. WO 2015/064348, Monoclonal antibody that recognizes sugar-chain-deficient human IgA1 hinge region, and use therefor, published May 7, 2015.

Intl. Pat. Publ. WO 2019/023501 (Kleo Pharmaceuticals, Inc.), Universal ABT compounds and uses thereof, published Jan. 31, 2019.

Japanese Pat. Publ. JP 2010-285419, Antibody recognizing sugar chain deficient human IgA1 hinge region and use thereof, published Dec. 24, 2010.

Non-Patent Literature

Acqua et al., Increasing the affinity of a human IgG1 for the neonatal Fc receptor: biological consequences. The Journal of Immunology, 169(9), 5171-5180 (2002).

Alegre et al., A non-activating humanized anti-CD3 monoclonal antibody keeps immunosuppressive properties in vivo. Transplantation 57.11 (1994): 1537-1543.

Alves et al., Oriented surface immobilization of antibodies at the conserved nucleotide binding site for enhanced antigen detection, Langmuir, 28, 9640-9648 (2012).

Barratt et al., Randomized phase II JANUS study of atacicept in patients with IgA nephropathy and persistent proteinuria. Kidney Int. Rep., 7(8), 1831-1841 (2022).

Bolt et al., The generation of a humanized, non-mitogenic CD3 monoclonal antibody which keeps in vitro immunosuppressive properties. European Journal of Immunology 23(2), 403-411 (1993).

Caianiello et al., Bifunctional small molecules that mediate the degradation of extracellular proteins. Nature Chemical Biology, 17(9), 947-953 (2021) describes ASGPR-dependent mechanism of Molecular Degraders of Extracellular targets (MoDE)-induced degradation.

Choe, Durgannavar, & Chung, Fc-binding ligands of immunoglobulin G: An overview of high affinity proteins and peptides. Materials, 9(12) (2016).

Cobb et al., A combination of two human neutralizing antibodies prevents SARS-CoV-2 infection in rhesus macaques. bioRxiv, 2021-09 (2021). More references with details of engineering also available.

Gupta et al., Computationally designed antibody-drug conjugates self-assembled via affinity ligands. Nature Biomedical Engineering, vol. 3, 917-929 (2019).

Hui et al., LASIC: Light activated site-specific conjugation of native IgGs. Bioconjugate Chem., 26, 1456-1460 (2015).

IBL-America, Novel ELISA (using KM55) specifically detects Gd-IgA1 #27600 Gd-IgA1 (Galactose-deficient IgA1), Pamphlet 2.

Ishiko et al., Utility of glomerular Gd-IgA1 staining for indistinguishable cases of IgA nephropathy or Alport syndrome. Clin Exp Nephrol., 25(7), 779-787 (July 2021).

Knoppova et al., Pathogenesis of IgA nephropathy: Current understanding and implications for development of disease-specific treatment. J. Clin. Med., 10(19), 4501 (2021).

Kruljec & Bratkovič, Alternative affinity ligands for immunoglobulins. Bioconjugate Chem., 28(8), 2009-2030 (2017).

Kruljec et al., Development and characterization of peptide ligands of immunoglobulin G Fc region. Bioconjugate Chem., 29(8), 2763-2775 (2018).

Kuroyanagi et al., Galactose-deficient IgA1 is involved in IgA deposition in renal grafts biopsied one hour after kidney transplantation. Intern. Med. (Oct. 26, 2022).

Lai et al., IgA nephropathy. Nature Rev. Dis. Primers, 2, 16001 (2016).

Leabman et al., Effects of changed FcγR binding on antibody pharmacokinetics in cynomolgus monkeys. MAbs, Vol. 5, No. 6 (Taylor & Francis, 2013).

Lund et al., Multiple binding sites on the $CH_2$ domain of IgG for mouse FcγR11. Molecular immunology 29.1 (1992): 53-59.

Martin-Penagos et al., Measurement of galactosyl-deficient IgA1 by the monoclonal antibody Km55 contributes to predicting patients with IgA nephropathy with high risk of long-term progression. Nefrologia, 41(3), 311-320 (May-June 2021).

Moldoveanu et al. Experimental evidence of pathogenic role of IgG autoantibodies in IgG nephropathy. J. Autoimmun., 118, 102593 (2021).

Moldoveanu et al., Patients with IgA nephropathy have increased serum galactose-deficient IgA1 levels. Kidney International, 71(11), 1148-54 (2007).

Muguruma et al., Kinetics-based structural requirements of human immunoglobulin G binding peptides. ACS Omega, 4, 14390-14397 (2019).

Mustafaoglu et al., Antibody purification via affinity membrane chromatography method using nucleotide binding site targeting with a small molecule, Analyst, 141(24), 6571-6582 (Nov. 28, 2016).

Neufeld et al., Galactose-deficient IgA1 (GD-IgA1) in skin and serum from patients with skin-limited and systemic IgA Vasculitis. J. Am. Acad. Dermatol. (Mar. 19, 2019).

Nihei, Suzuki, and Suzuki, Current understanding of IgA antibodies in the pathogenesis of IgA nephropathy. Front. Immunol., 14, 1165394 (2023).

Nishioka et al. Glomerulonephritis with severe nephrotic syndrome induced by immune complexes composed of galactose-deficient IgA1 in primary Sjögren's syndrome: A case report. BMC Nephrol., 22(1), 108 (Mar. 25, 2021).

Pettersson & Crews, PROteolysis TArgeting Chimeras (PROTACs)—Past, present, and future. Drug Discovery Today: Technologies, Vol. 31, pp. 15-27 (Elsevier BV, 2019).

Rajasekaran, Julian, & Rizk, IgA nephropathy: An interesting autoimmune kidney disease. Am. J. Med. Sci., 361(2), 176-194 (2021).

Saxena & Wu, Advances in therapeutic Fc engineering-modulation of IgG-associated effector functions and serum half-life. Frontiers in immunology, 7, 580 (2016) (review).

Shields et al., High resolution mapping of the binding site on human IgG1 for FcγRI, FcγRII, FcγRIII, and FcRn and design of IgG1 variants with improved binding to the FcγR. Journal of Biological Chemistry 276(9), 6591-6604 (2001).

Strohl, Optimization of Fc-mediated effector functions of monoclonal antibodies. Current Opinion in Biotechnology, 20(6), 685-691 (2009).

Suzuki et al. Aberrantly glycosylated IgA1 in IgA nephropathy patients is recognized by IgG antibodies with restricted heterogeneity. J. Clin. Invest., 119(6), 1668-1677 (2009).

Suzuki et al., IgA nephropathy and IgA vasculitis with nephritis have a shared feature involving galactose-deficient IgA1-oriented pathogenesis. Kidney Int. 2018 March; 93(3):700-705.

Suzuki, Biomarkers for IgA nephropathy based on multi-hit pathogenesis. Clinical Exp. Nephrol., 23(1), 26-31 (January 2019).

Tamm & Schmidt, IgG binding sites on human Fcγ receptors. International reviews of immunology 16(1-2), 57-85 (1997).

Tilman et al., Novel human IgG1 and IgG4 Fc-engineered antibodies with abolished immune effector functions. Protein Engineering, Design and Selection, Volume 29, Issue 10, pages 457-466 (October 2016). This paper shows that even LALA itself abolishes c1q binding. P329A alone is tested. P329A abolishes c1q binding and reduces FcgR binding. They do not test P329A/LALA but show that P329G/LALA further reduces FcgR binding beyond LALA alone.

Yamada et al., AJICAP: Affinity peptide mediated regiodivergent functionalization of native antibodies. Angew. Chem. Int. Ed. Engl., 58(17), 5592-5597 (Apr. 16, 2019).

Yamasaki et al., Galactose-deficient IgA1-specific antibody recognizes GalNAc-changed unique epitope on hinge region of IgA1. Monoclonal Antibody Immunodiagn. Immunother., 37(6), 252-256 (December 2018).

Yasutake et al., Novel lectin-independent approach to detect galactose-deficient IgA1 in IgA nephropathy Nephrol Dial Transplant, 30, 1315-1321 (2015).

Zalevsky et al., Enhanced antibody half-life improves in vivo activity. Nature Biotechnology, 28(2), 157-159 (2010).

Zhang et al., Clinical significance of galactose-deficient IgA1 by Km55 in patients with IgA nephropathy, Kidney Blood Pressure Res., 44, 1196-1206 (2019).

Zhang et al., Km55 monoclonal antibody staining in IgA-dominant infection-related glomerulonephritis. Nephron, 145(3), 225-237 (2021).

Textbooks and Technical References

Current Protocols in Immunology (CPI), Coligan, Kruisbeek, Margulies, Shevach, and Strobe, (eds.) (John Wiley and Sons, Inc., 2003). (ISBN 0471142735, 9780471142737).

Current Protocols in Molecular Biology (CPMB), (2014). Frederick M. Ausubel (ed.), John Wiley and Sons (ISBN 047150338X, 9780471503385).

Current Protocols in Protein Science (CPPS), (2005). John E. Coligan (ed.), John Wiley and Sons, Inc.

Immunology (2006). Werner Luttmann, published by Elsevier.

Janeway's Immunobiology, (2014). Kenneth Murphy, Allan Mowat, Casey Weaver (eds.), Taylor & Francis Limited, (ISBN 0815345305, 9780815345305).

Laboratory Methods in Enzymology: DNA, (2013). Jon Lorsch (ed.) Elsevier (ISBN 0124199542).

Lewin's Genes XI, (2014). published by Jones & Bartlett Publishers (ISBN-1449659055).

Molecular Biology and Biotechnology: A Comprehensive Desk Reference, (1995). Robert A. Meyers (ed.), published by VCH Publishers, Inc. (ISBN 1-56081-569-8).

Molecular Cloning: A Laboratory Manual, 4th edition, Green & Sambrook, (2012). Cold Spring Harbor Laboratory Press, Cold Spring Harbor, N.Y., USA (ISBN 1936113414).

The Encyclopedia of Molecular Cell Biology and Molecular Medicine, Porter et al. (eds.), published by Blackwell Science Ltd., 1999-2012 (ISBN 9783527600908).

The Merck Manual of Diagnosis and Therapy, 19$^{th}$ edition (Merck Sharp & Dohme Corp., 2018).

Remington's, Pharmaceutical Sciences 23$^{rd}$ edition (Elsevier, 2020).

Smith & March, March's Advanced Organic Chemistry: Reactions, Mechanisms, and Structure, 5th edition (John Wiley & Sons, 2001).

Larock, Comprehensive Organic Transformations, 2nd edition (John Wiley & Sons, 1999).

Greene & Wuts, Protecting Groups in Organic Synthesis, 3rd edition (John Wiley & Sons, 1999).

Throughout this application, several publications are referenced by author name and date, or by patent number or patent publication number. The disclosures of these publications are incorporated in their entireties by reference into this application to describe the state of the art more fully as known to persons having ordinary skill as of the invention described and claimed herein. However, the citation of a reference herein should not be construed as an acknowledgement that this reference is prior art to the present invention.

All patents and publications cited throughout this specification are incorporated by reference to reveal and describe the materials and methods that might be used with the technologies described in this specification. The publications discussed are provided only for their disclosure before the filing date. They should not be construed as an admission that the inventors may not antedate this disclosure under past invention or for any other reason. If there is an apparent discrepancy between a past patent or publication and the description given in this specification, the specification (including any definitions) and claims shall control. All statements about the date or contents of these documents are based on the information available to the applicants. These statements are no admission to the correctness of the dates or contents of these documents. The publication dates given in this specification may differ from the actual publication dates. If there is an apparent discrepancy between a publication date in this specification and the actual publication date supplied by the publisher, the actual publication date shall control.

The invention claimed is:

1. A composition of matter having the chemical formula [AGN101]:

[AGN101]

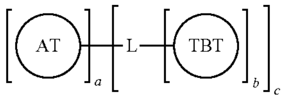

wherein,

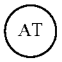

is a galactose-deficient Immunoglobulin A1 (Gd-IgA1) binding moiety comprising a heavy chain comprising the polypeptide sequences of SEQ ID NO: 9, SEQ ID NO: 10, and SEQ ID NO: 11, and a light chain comprising the polypeptide sequences of SEQ ID NO: 12, SEQ ID NO: 13, and SEQ ID NO: 14;

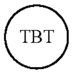

is a cellular receptor-binding moiety comprising an N-acetyl-D-galactosamine (GalNAc) group; and L is a linking group, a is 1, b is 1, 2, or 3, and c is 1 or 2.

2. The composition of matter of claim 1, wherein

comprises a heavy chain polypeptide sequence of SEQ ID NO: 1 and light chain polypeptide sequence SEQ ID NO: 2.

3. The composition of matter of claim 1, wherein

comprises a heavy chain polypeptide sequence of SEQ ID NO: 3 and light chain polypeptide sequence SEQ ID NO: 2.

4. The composition of matter of claim 1, wherein

comprises a heavy chain polypeptide sequence of SEQ ID NO: 4 and light chain polypeptide sequence SEQ ID NO: 2.

5. The composition of matter of claim 1, wherein L comprises one or more $—(O)C—[(CH_2)_nO]_m(CH_2)_nNH—$, $—[(CH_2)_nO]_mNHC(O)[(CH_2)_nO]_mNH—$, and $—[(CH_2)_nO]_m\{NHC(O)[(CH_2)_nO]_m\}_pNH—$, wherein each m and n are independently 1 to 10.

6. The composition of matter of claim 1, wherein L comprises one or more $—[(CH_2)_n—O]_m—$, wherein each m and n are independently 1 to 10.

7. The composition of matter of claim 1, wherein L comprises $—(CH_2)_n—O—(CH_2CH_2O)_n—(CH_2)_n—$, wherein each n is independently 1-10.

8. The composition of matter of claim 1, wherein

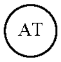

comprises an IgG1 heavy chain that is connected to L at an amino acid residue selected from K246 and K248 of the IgG1 heavy chain according to the EU numbering scheme.

9. The composition of matter of claim 8, wherein

is connected to L at the amino acid residue K248 of the IgG1 heavy chain.

10. The composition of matter of claim 1, wherein b is 3, and each

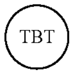

comprises an N-acetyl-D-galactosamine (GalNAc) group.

11. The composition of matter of claim 1, wherein b is 3, and

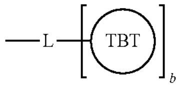

comprises the chemical formula:
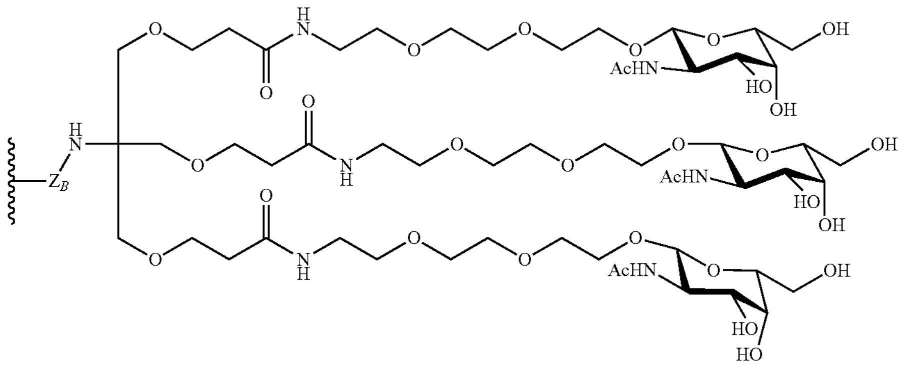
wherein,
$Z_B$ is absent, $—(CH_2)_{IM}—$, $—C(=O)—(CH_2)_{IM}—$, or $—C(=O)—(CH_2)_{IM}—NR_M—$;
$R_M$ is H or $C_1$-$C_3$ alkyl; and
each occurrence of IM is independently 1, 2, or 3.
12. The composition of matter of claim 1, wherein b is 2 or 3, ar
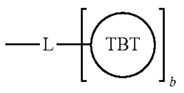
has the chemical formula [MAT01A], [MAT01B], [MAT01C], or [MAT01D]:

[MAT01A]
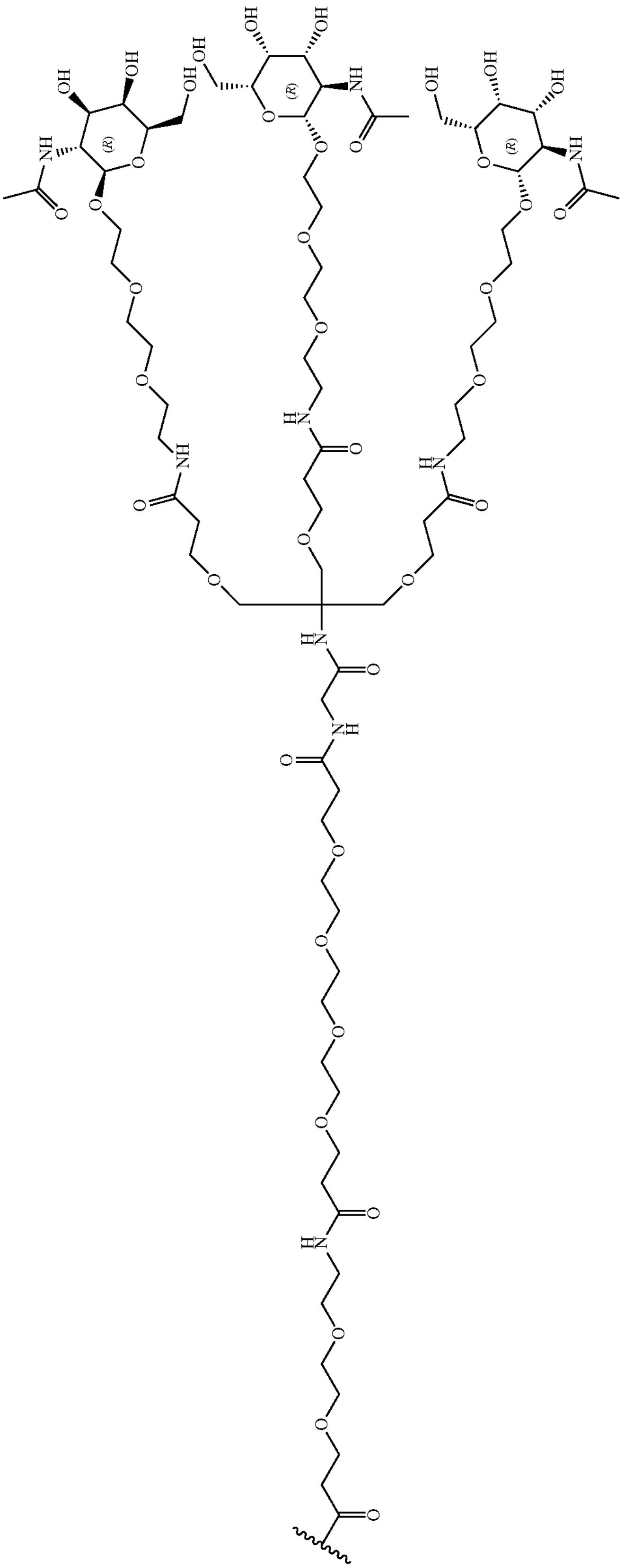

-continued
[MAT01B]
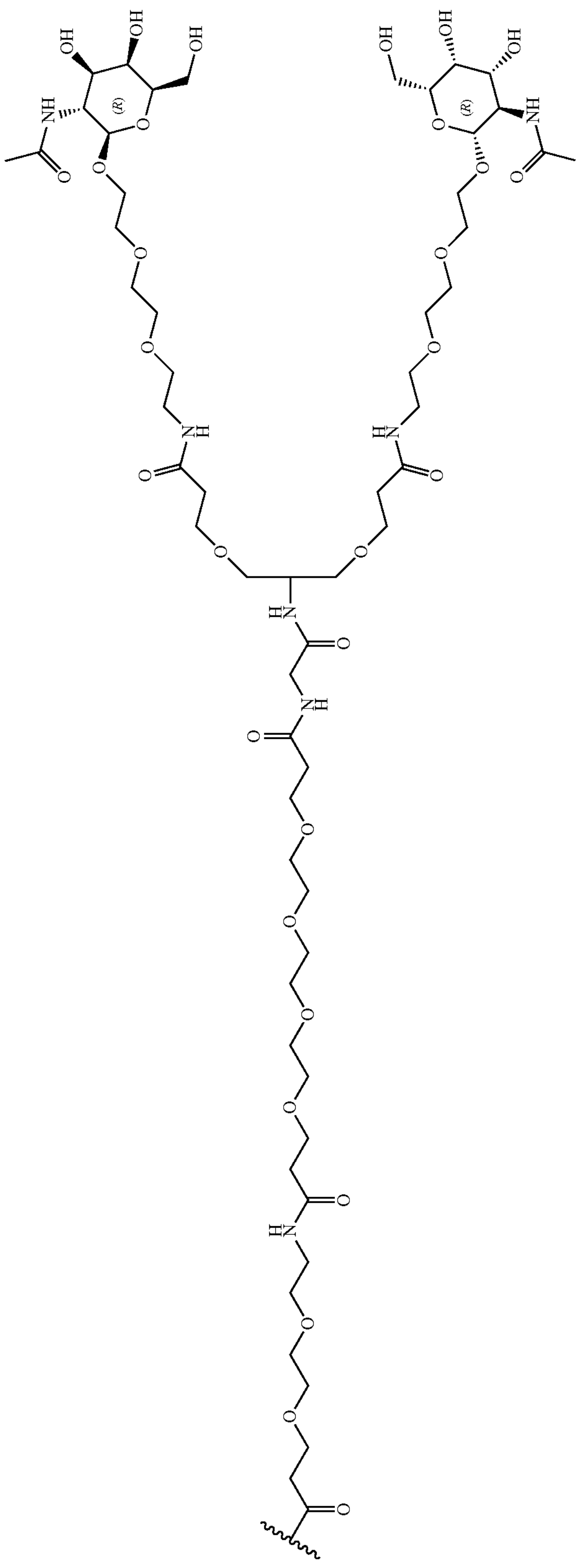

-continued
[MAT01C]
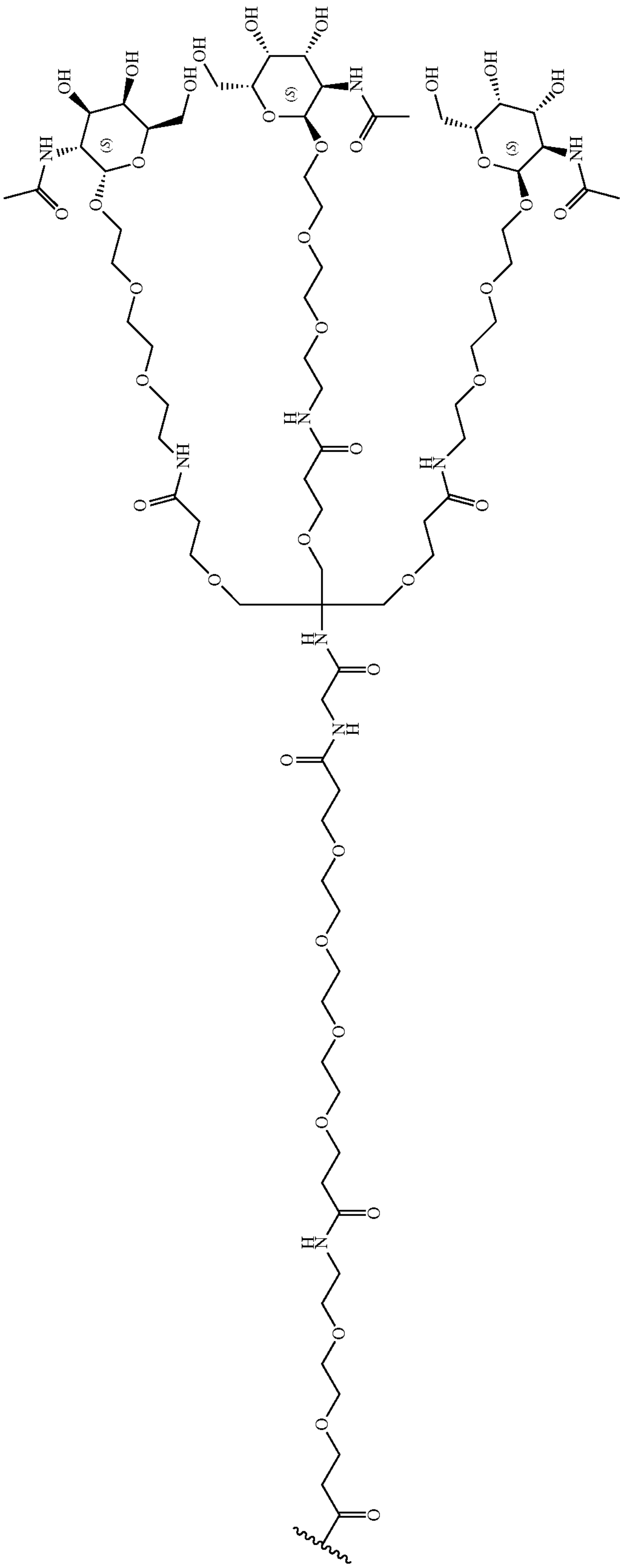

-continued
[MAT01D]
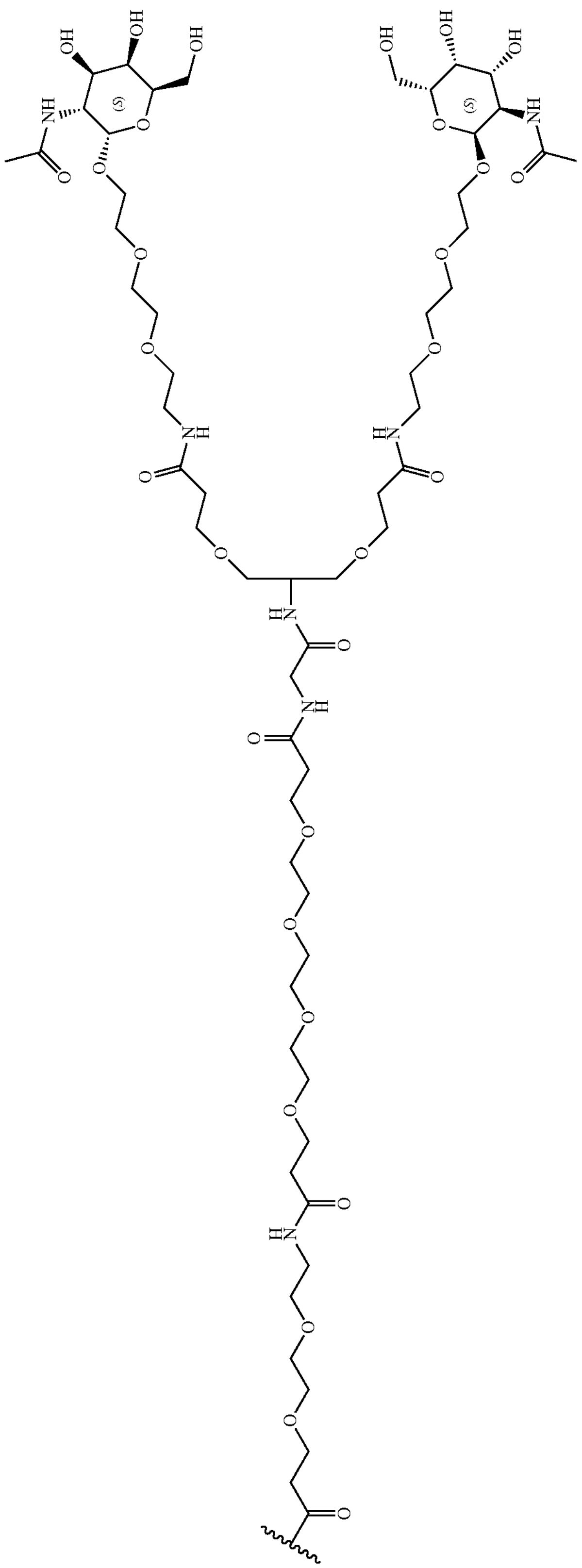

13. The composition of matter of claim 1, wherein c is 2.
14. The composition of matter of claim 1, wherein a is 1, b is 3, c is 2, each
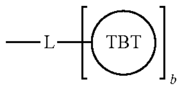
has the chemical formula [MAT01A]:
[MAT01A]
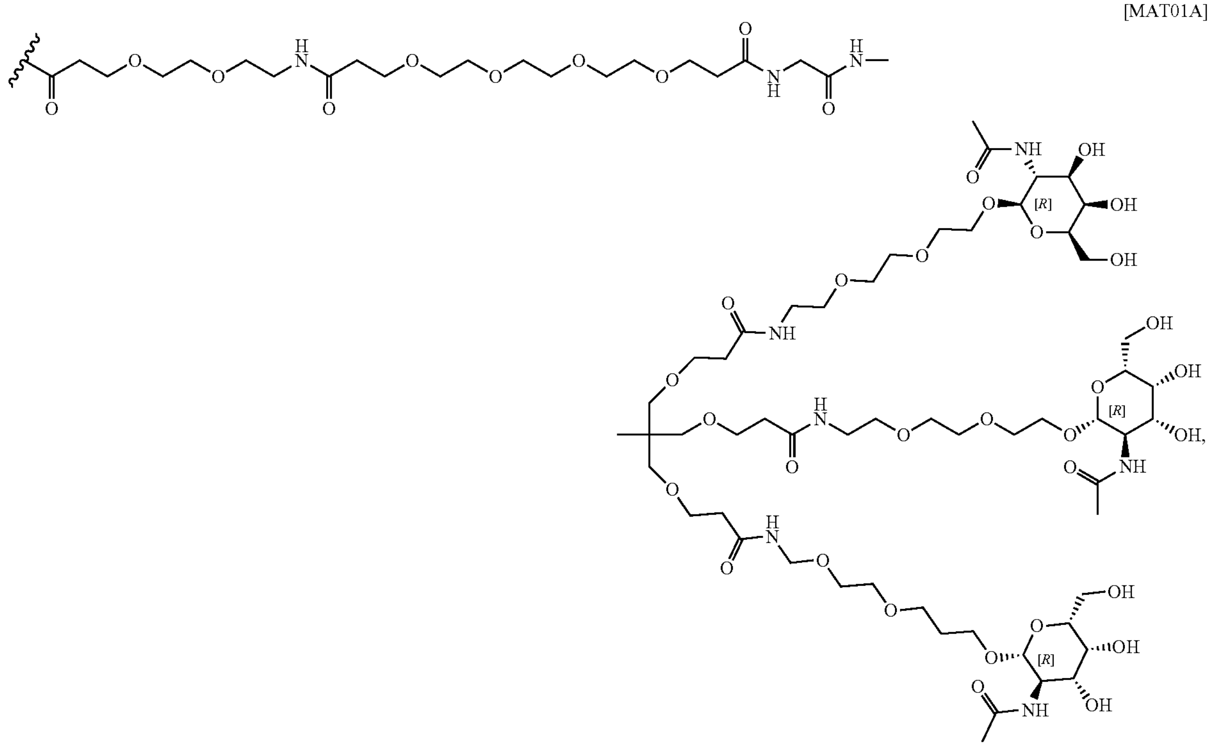
and
wherein
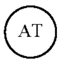
comprises an IgG1 heavy chain that is connected to respective L at an amino acid residue selected from K246 and K248 of the IgG1 heavy chain according to the EU numbering scheme.
* * * * *